(12) United States Patent
Steiner et al.

(10) Patent No.: US 6,835,812 B1
(45) Date of Patent: Dec. 28, 2004

(54) HUMAN P-HYDE PROTEINS

(75) Inventors: Mitchell S. Steiner, Germantown, TN (US); Chiang Wang, Memphis, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/562,930

(22) Filed: May 2, 2000

Related U.S. Application Data

(63) Continuation-in-part of application No. 09/449,817, filed on Nov. 26, 1999, which is a continuation-in-part of application No. 09/302,457, filed on Apr. 29, 1999, now abandoned.

(51) Int. Cl.$^7$ .............................................. C07K 14/00
(52) U.S. Cl. ...................................................... 530/350
(58) Field of Search ........................................ 530/350

(56) References Cited

FOREIGN PATENT DOCUMENTS

| | | | |
|---|---|---|---|
| EP | 1074617 A2 | * | 2/2001 |
| WO | WO 97/22695 A2 | | 6/1997 |
| WO | WO 00/71564 A2 | * | 11/2000 |
| WO | WO 01/53454 A2 | * | 7/2001 |
| WO | WO 01/59127 A2 | * | 8/2001 |
| WO | WO 01/72962 A2 | * | 10/2001 |
| WO | WO 02/52274 A2 | * | 7/2002 |

OTHER PUBLICATIONS

Passer et al. The p53–inducible TSAP6 gene product regulated apoptosis and the cell cycle and interacts with Nix and the Myt1 kinase. PNAS (2003) 100(5): 2284–2289.*

IPorkka et al. Human pHyde is not a Classical Tumor Suppressor Gene in Prostate Cancer. Int. J. Caner (2003) 106: 72–735.*

GenBank Accession No. AAL78206, tumor suppressor pHyde [*Homo sapiens*], published Feb. 15, 2002.*

Rinaldy et al. Role of pHyde Novel Gene Product as an Intrinsic Factor for Apoptotic Pathway in Prostate Cancer. Gan To Kagaku Ryoho (May, 2000) 27 Suppl 2: 215–222.*

Steiner et al. Growth Inhibition of Prostate Cancer by an Adenovirus Expression a Novel Tumor Suppressor Gene, pHyde. Cancer Research (Aug. 2000) 60: 4419–4425.*

Zhang et al. Apoptosis induction in prostate cancer cells by a novel gene product, pHyde, involves caspase–3. Oncogene (2001) 20: 5982–5990.*

* cited by examiner

*Primary Examiner*—Kathleen Kerr
(74) *Attorney, Agent, or Firm*—Eitan, Pearl, Latzer & Cohen Zedek, LLP; Mark S. Cohen

(57) ABSTRACT

This invention provides isolated nucleic acids of the rat and human p-Hyde gene, analogs, fragments, mutants and variants thereof of the p-Hyde family. The invention provides polypeptides, fusion proteins, chimerics, fusion proteins, antisense molecules, antibodies, and uses thereof. Also, this invention is directed to a method of inducing susceptibility to apoptosis with p-Hyde, a method of suppressing tumor growth with p-Hyde, and a method of treating a subject with cancer with p-Hyde alone or in combination with radiation, chemotherapy, or UV mimetic drugs. The invention also relates to the therapy of human cancers, which have a mutation in the p-Hyde gene, including gene therapy, protein replacement therapy and protein mimetics. The invention further relates tot the screening of drugs for cancer therapy. Finally the invention relates to the screening o the p-Hyde gene for mutations, which are useful for diagnosing the predisposition to cancer.

4 Claims, 48 Drawing Sheets

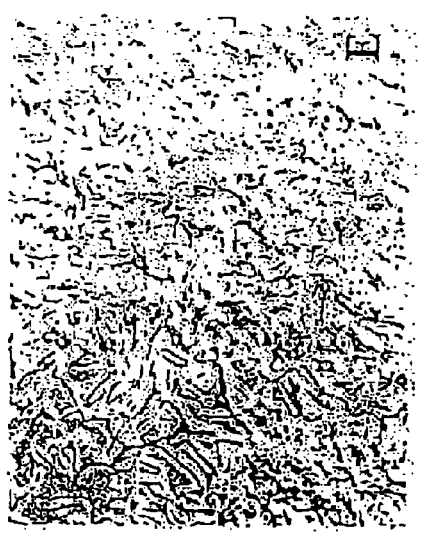
FIG. 5

SECUENCE OF REGION A OF AdRSVpHyde:

GCGGCCGCCATCATCAATAATATACCTTATTTTGGATTGAAG
CCAATATGATAATGAGGGGGTGGAGTTTGTGACGTGGC
GCGGGGCGTGGGAACGGGGCGGGTGACGTAGTAGTGTGGC
GGAAGTGTGATGTTGCAAGTGTGGCGGAACACATGTAAGC
GACGGATGTGGCAAAAGTGACGTTTTTGGTGTGCGCCGGTG
TACACAGGAAGTGACAATTTTCGCGCGGTTTTAGGCGGA
TGTTGTAGTAAATTTGGGCGTAACCGAGTAAGATTTGGCCAT
TTTCGCGGGAAAACTGAATAAGAGGAAGTGAAATCTGA
ATAATTTTGTGTTACTCATAGCGCGTAATATTTGTCTAGGGCC
GCGGGGACTTTGACCGTTTACGTGGAGACTCGCCCAG
GGCGCGCCCCGATGTACGGGCCAGATATACGCGTATCTGAG
GGGACTAGGGTGTGTTTAGGCGAAAAGCGGGGCTTCGGT
TGTACGCGGTTAGGAGTCCCCTCAGGATATAGTAGTTTCGCT
TTTGCATAGGGAGGGGGAAATGTAGTCTTATGCAATAC
TCTTGTAGTCTTGCAACATGGTAACGATGAGTTAGCAACATG
CCTTACAAGGAGAGAAAAAGCACCGTGCATGCCGATTG
GTGGAAGTAAGGTGGTACGATCGTGCCTTATTAGGAAGGCTA
ACAGACGGGTCTGACATGGATTGGACGAACCACTGAATT
CCGCATTGCAGAGATATTGTATTTAAGTGCCTAGCTCGATAC
AATAAACGCCATTTGACCATTCACCACATTGGTGTGCA
CCTCCGGCCCTGGCCACTCTCTTCCGCATCGCTGTCTGCGGG
GGCCAGCTGTTGGGCTCGCGGTTGAGGACAAACTCTTC
GCGGTCTTTCCAGTACTCTTGGATCGGAAACCCGTCGGCCCTC
CGAACGGTACTCCGCCGCCGAGGGACCTGAGCGAGTCC
GCATCGACCGGATCGGAAAACCTCTCGAGAAAGGCGTGTAA
CCAGTCACAGTCGCTCTAGAACTAGTGGATCCCCCGGGC
TGCAGGAATTCGATAATTCGGCACGAGGCTGCCGAGGCACT
GTGATGTCCGGGGAGATGGACAAACCGCTCATCAGTCGC
CGCTTGGTGGACAGTGATGGCAGTCTGGCTGAGGTCCCCAA
GGAGGCTCCCAAAGTGGGCATCCTGGGCAGCGGGGATTT
TGCCCGGTCCCTGGCCACACGCCTGGTGGGCTCTGGCTTCT
TTGTGGTGGTGGGAAGCCGTAACCCCAAACGCACTGCCG
GCCTCTTCCCCTCCTTAGCCCAAGTGACTTTCCAGGAGGAGG
CCGTGAGCTCTCCAGAGGTCATCTTTGTGGCCGTGTTC
CGGGAGCACTACTCCTCACTGTGCAGTCTTGCTGACCAGTTG
GCTGGCAAGATCCTAGTGGATGTAAGCAACCCCACGGA
GAAGGAGCGTCTTCAGCACCGCCAGTCGAACGCCGAGTACC
TGGCCTCCCTCTTCCCTGCCTGCACTGTGGTCAAGGCCT
TCAACGTCATCTCTGCATGGGCCCTACAGGCTGGCCCAAGG
GATGGGAACAGGCAGGTGCTCATCTGCGGTGACCAGCTG
GAAGCCAAGCACACCGTCTCAGAGATGGCGCGCGCCATGG
GTTTCACCCCACTGGACATGGGATCCCTGGCCTCAGCGAG
GGAGGTAGAGGCCATACCCCTGCGCCTCCTTCCATCCTGGA
AGGTGCCCACCCTCCTGGCCCTGGGGCTAAGCACACAAA

FIG.10A

```
GCTATGCCTACAACTTCATCCGGGACGTTCTACAGCCGTACA
TCCGGAAAGATGAGAACAAGTTCTACAAGATGCCCCTG
TCTGTGGTCAACACCACGaTACCCTGTGTGGCTTACGTGCTG
CTGTCCCTGGTTTACCTGCCTGGTGTGCTGGCAGCTGC
CCTTCAGCTGAGGAGGGGGACCAAGTACCAGCGCTTCCCAG
ACTGGCTGGACCATTGGCTGCAGCACCGCAAGCAGATCG
GGCTACTCAGCTTTTTTTTCGCCATGCTGCACGCTCTCTACAG
CTTCTGCCTGCCGCTGCGCCGCTCCCACCGCTATGAT
CTGGTCAACCTGGCTGTGAAGCAGGTCCTGGCCAACAAGAG
CCGCCTCTGGGTTGAGGAAGAAGTCTGGCGGATGGAGAT
ATACCTGTCCCTGGGTGTGCTGGCTCTGGGCATGCTGTCACT
GCTGGCGGTTACCTCGATCCCTTCCATTGCAAACTCAC
TCAACTGGAAGGAGTTCAGCTTTGTGCAGTCCACGCTGGGC
TTCGTGGCCCTGATGCTGAGCACAATGCACACCCTCACC
TACGCGCTGGACCCGTGCTTTTGAGGAAAACCACTACAAGTTC
TACCTGCCACCCACATTCACGCTCACGCTGCTCCTGCC
CTGTGTCATCATCCTGGCCAAGGGCCTCTTCCTCCTGCCCTG
CCTCAGCCACAGACTCACCAAGATCCGCAGGGGCTGGG
AGAGGGATGGTGCCGTCAAGTTCATGCTGCCCGCTGGCCAC
ACACAGGGGGAGAAAACAAGCCACGTGTGAGGCCCTGGA
AATGGAGACAGGCACAGCTTGTGGGGGCCCTGGGCTGGGT
TCGGGTCTCTTTTCTGGGATGGTATATGCGTGGGTGGCCG
AGGTCTGAATTTCTGGGATGCAGGTGTATGCCGAGATACTCA
GAATGGCGTACCACACATGCGATAAGAGCTCACATATA
TTTCATATATAATAGGATTTTCTATTATTCTTAGTTAAAAAAAA
ATAGTGGGTCCTTATATTTCAACTTATGCAGGGTCC
CTATATTTCAACTTGAGCATTTCAGAGCAAATGCCACACATTA
AACAGCAGATCCCACCCTTGTGGTAGCTGCAGAGACA
GACAGAAACTTCTGGTtATGAGAGAGACTGTATTTTGTTGGAT
TCTACCTTTAATCCCCGTTCTCTACGTTcCCCTGTTA
GCCACATCTTAACGTTGGTGCAGAGCTGGGACAAGAGCTGG
CTCTGGTGCAGCCTCCCCATCCCAGGGCTAGGAAACAA
GCCTCTGATGAACAGAGGGACCAGGTCTGGACCCTCCTGCT
CCCGCTTCCCTGGGCTCGAGTGGGGAGGCTCAGCGGGAT
CCCCCGCAATCTGTGCAGGAGTTTTCACAGGTCTGTCCTTTC
TTCCGGGAGCGGTCTGAAGCGGCCCCATCTGATCCTAG
CTGAGCCGAGATTGTTCCCCACTCCCTGAAAGTCCAGAGTCA
CCGTGGAGCCTGCAAATTGCTCCTTCTGCGAAGGTGT
AAGTCACCGTCTCACCAGAGCCATTAACGAACCTGATCTTCA
GAAGAAGCATAATTGTTTCCCCTCCATTAAGTTGGTGG
TGACCCTCTTTAAACCACTGTGCCTTCTCGCCTTTCCCATCAC
TAATTTGGGCATCTCCATGGAGTGGACTCTTGTCGGG
GCAGTTCAGGGGGGAGGGAAGCATTAGAGATTGCGGAGAA
TAACCATCGAAGCCTCCCTTGGATGTTCCCAGGCGTGCCT
```

FIG.10B

TCATTAAATTGGTCCCTAATGAGAATGACAGGGGACCCCTGT
TGCCTGTaTGCAGAGAACCAGCCTTCTGAGCACCCAGG
AAACACAGTGGCCCCACGCCCTTCAGGGGGTCCCACGTCC
CCTTTCCCATGCTTTTGCCTCCCTCCCTCCCGGTTACAA
TCAACCATAAAAGTCTGCAAATATTGTTTTTTGAATTATCAAG
CTTATCGATACCGTCGAAACTTGTTTATTGCAGCTTA
TAATGGTTACAAATAAAGCAATAGCATCACAAATTTCACAAAT
AAAGCATTTTTTCACTGCATTCTAGTTGTGGTTTGT
CCAAACTCATCAATGTATCTTATCATGTCTGGATCCGACCTCG
G

SECUENCE OF REGION B OF AdRSVpHyde:

ATCTGGAAGGTGCTGAGGTACGATGAGACCCGCACCAGGTG
CAGACCCTGCGAGTGTGGCGGTAAACATATTAGGAACCA
GCCTGTGATGCTGGATGTGACCGAGGAGCTGAGGCCCGATC
ACTTGGTGCTGGCCTGCACCCGCGCTGAGTTTGGCTCTA
GCGATGAAGATACAGATTGAGGTACTGAAATGTGTGGGCGT
GGCTTAAGGGTGGGAAAGAATATATAAGGTGGGGGTCTT
ATGTAGTTTTGTATCTGTTTTGCAGCAGCCGCCGCCGCCATG
AGCACCAACTCGTTTGATGGAAGCATTGTGAGCTCATA
TTTGACAACGCGCATGCCCCCATGGGCCGGGGTGCGTCAGA
ATGTGATGGGCTCCAGCATTGATGGTCGCCCCGTCCTGC
CCGCAAACTCTACTACCTTGACCTACGAGACCGTGTCTGGAA
CGCCGTTGGAGACTGCAGCCTCCGCCGCCGCTTCAGCC
GCTGCAGCCACCGCCCGCGGGATTGTGACTGACTTTGCTTTC
CTGACCCGCTTGCAAGCAGTGCAGCTTCCCGTTCATC
CGCCCGCGATGACAAGTTGACGGCTCTTTTGGCACAATTGG
ATTCTTTGACCCGGGAACTTAATGTCGTTTCTCAGCAGC
TGTTGGATCTGCGCCAGCAGGTTTCTGCCCTGAAGGCTTCCT
CCCCTCCCAATGCGGTTTAAAACATAAATAAAAAACCA
GACTCTGTTTGGATTTGGATCAAGCAAGTGTCTTGCTGTCTTT
ATTTAGTGGGTTTTGCGCGCGCGGTAGGCCCGGGACCA
GCGGTCTCGGTCGTTGAGGGTCCTGTGTATTTTTTCCAGGAC
GTGGTAAAGGTGACTCTGGATGTTCAGATACATGGGCA
TAAGCCCGTCTCTGGGGTGGAGGTAGCACCACTGCAGAGCT
TCATGCTGCGGGTGGTGTTGTAGATGATCCAGTCGTAG
CAGGAGCGCTGGGCGTGGTGCCTAAAAATGTCTTTCAGTAG
CAAGCTTATTGCCAGGGGCAGGCCCTTGGTGTAAGTGTT
TACAAAGCGGTTAAGCTGGGATGGGGGCATACGTGGGGATA
TGAGATGCATCTTGGACTGTATTTTTAGGTTGGCTATGT
TCCCAGCCATATCCCTCCGGGGATTCATGTTGTGCAGAACCA
CCAGCACAGTGTATCCGGTGCACTTGGGAAATTTGTCA
TGTAGCTTAGAAGGAAATGCGTGGAAGAACTTGGAGACGCC
CTTGTGACCTCCAAGATTTTCCATGCATTCGTCCATAAT
GATGGCAATGGGCCCACGGGCGGCGGCCTGGGCGAAGATA
TTTCTGGGATCACTAACGGCATAGTTGTGTTCCAGGATGA

FIG.10C

```
GATCGTCATAGGCCATTTTTACAAAGCGCGGGCGGAGGGTG
CCAGACTGCGGTATAATGGTTCCATCCGGCCCAGGGGCG
TAGTTACCCTCACAGATTTGCATTTCCCACGCTTTGAGTTCAG
ATGGGGGGATCATGTCTACCTGCGGGGCGATGAAGAA
AACGGTTTCCGGGGTAGGGGAGATCAGCTGGGAAGAAAGC
AGGTTCCTGAGCAGCTGCGACTTACCGCAGCCGGTGGGCC
GCTAAATCACACCTATTACCGGGTGCAACTGGTAGTTAAGAG
AGCTGCAGCTGCCGTCATCCCTGAGCAGGGGGCCACT
TCGTTAAGCATGTCCCTGACTCGCATGTTTTCCCTGACCAAAT
CCGCCAGAAGGCGCTCGCCGCCCAGCGATAGCAGTTC
TTGCAAGGAAGCAAAGTTTTTCAACGGTTTGAGACCGTCCGC
CGTAGGCATGCTTTTGAGCGTTTGACCAAGCAGTTCCA
GGCGGTCCCACAGCTCGGTCACCTGCTCTACGGCATCTCGA
TCCAGCATATCTCCTCGTTTCGCGGGTTGGGGCGGCTTT
CGCTGTACGGCAGTAGTCGGTGCTCGTCCAGACGGGCCAGG
GTCATGTCTTTCCACGGGCGCAGGGTCCTCGTCAGCGTA
GTCTGGGTCACGGTGAAGGGGTGCGCTCCGGGCTGCGCGC
TGGCCAGGGTGCGCTTGAGGCTGGTCCTGCTGGTGCTGAA
GCGCTGCCGGTCTTCGCCCTGCGCGTCGGCCAGGTAGCATT
TGACCATGGTGTCATAGTCCAGCCCCTCCGCGGCGTGGC
CCTTGGCGCGCAGCTTGCCCTTGGAGGAGGCGCCGCACGA
GGGGCAGTGCAGACTTTTGAGGGCGTAGAGCTTGGGCGCG
AGAAATACCGATTCCGGGGAGTAGGCATCCGCGCCGACGGC
CCCGCAGACGGTCTCGCATTCCACGAGCCAGGTGAGCTC
TGGCCGTTCGGGGTCAAAAACCAGGTTTCCCCCATGCTTTTT
GATGCGTTTCTTACCTCTGGTTTCCATGAGCCGGTGTC
CACGCTCGGTGACGAAAAGGCTGTCCGTGTCCCCGTATACA
GACTTGAGAGGCCTGTCCTAGAGCGGTGTTCCGCGGTCC
TCCTCGTATAGAAACTCGGACCACTCTGAGACAAAGGCTCGC
GTCCAGGCCAGCACGAAGGAGGCTAAGTGGGAGGGGTA
GCGGTCGTTGTCCACTAGGGGGTCCACTCGCTCCAGGGTGT
GAAGACACATGTCGCCCTCTTCGGCATCAAGGAAGGTGA
TTGGTTTGTAGGTGTAGGCCACGTGACCGGGTGTTCCTGAA
GGGGGGCTATAAAAGGGGGTGGGGGCGCGTTCGTCCTAC
CTCTCTTCCGCATCGCTGTCTGCGAGGGCCAGCTGTTGGGG
TGAGTACTCCCTCTGAAAAGCGGGCATGACTTCTGCGCT
AAGATTGTCAGTTTCCAAAAACGAGGAGGATTTGATATTCAC
CTGGCCCGCGTTGATGCCTTTGAGGGTGGCCGCATCCA
TCTGGTCAGAAAAGACAATCTTTTTGTTGTCAAGCTTGGTGG
CAAACGACCCGTAGAGGGCGTTGGACAGCAACTTGGCG
ATGGAGCGCAGGGTTTGGTTTTTGTCGCGATCGGCGCGCTC
CTTGGCCGCGATGTTTAGCTGCACGTATTCGCGCGCAAC
GCACCGCCATTCGGGAAAGACGGTGGTGCGCTCGTCGGGC
ACCAGGTGCACGCGCCAACCGCGGTTGTGCAGGGTGACAA
GGTCAACGCTGGTGGCTACCTCTCGCGCTAGGCGCTCGTTG
GTCCAGCAGAGGCGGCCGCCCTTGCGCGAGCAGAATGGC
```

FIG.10D

```
GGTAGGGGGTCTAGCTGCGTCTCGTCCGGGGGTCTGCGTC
CACGGTAAAGACCCCGGGCAGCAGGCGCGCGTCGAAGTA
GTCTATCTTGCATCCTTGCAAGTCTAGCGCCTGCTGCCATGC
GCGGGCGGCAAGCGCGCGCTCGTATGGGTTGAGTGGGG
GACCCCATGGCATGGGGTGGGTGAGCGCGGAGGCGTACAT
GCCGCAAATGTCGTAAACGTAGAGGGGCTCTCTGAGTATT
CCAAGATATGTAGGGTAGCATCTTCCACCGCGGATGCTGGC
GCGCACGTAATCGTATAGTTCGTGCGAGGGAGCGAGGAG
GTCGGGACCGAGGTTGCTACGGGCGGGCTGCTCTGCTCGG
AAGACTATCTGCCTGAAGATGGCATGTGAGTTAAATGATA
TGGTTGGACGCTGGAAGACGTTGAAGCTGGCGTCTGTGAGA
CCTACCGCGTCACGCACGAAGGAGGCGTAGGAGTCGCGC
AGCTTCTTGACCAGCTCGGCGGTGACCTGCACGTCTAGGGC
GCAGTAGTCCAGGGTTTCCTTGATGATGTCATACTTATC
CTGTCCCTTTTTTTTCCACAGCTCGCGGTTGAGGACAAACTCT
TCGCGGTCTTTCCAGTACTCTTGGATCGGAAACCCGT
CGGCCTCCGAACGGTAAGAGCCTAGCATGTAGAACTGGTTG
AGGGCCTGGTAGGCGCAGCATCCCTTTTCTACGGGTAGC
GCGTATGCCTGCGCGGCCTTCCGGAGCGAGGTGTGGGTGA
GCGCAAAGGTGTCCCTGACCATGACTTTGAGGTACTGGTA
TTTGAAGTCAGTGTCGTCGCATCCGCCCTGCTCCCAGAGCAA
AAAGTCCGTGCGCTTTTTGGAACGCGGATTTGGCAGGG
CGAAGGTGACATCGTTGAAGAGTATCTTTCCCGCGCGAGGC
ATAAAGTTGCGTGTGATGCGGAAGGGTCCCGGCACCTCG
GAACGGTTGTTAATTACCTGGGCGGCGAGCACGATCTCGTT
AAAGCCGTTGATGTTGTGGCCCACAATGTAAAGTTCCAA
GAAGCGCGGGATGCCCTTGATGGAAGGCAATTTTTTAAGTTC
CTCGTAGGTGAGCTCTTCAGGGGAGCTGAGCCCGTGCT
CTGAAAGGGCCCAGTCTGCAAGATGAGGTGTGGAAGCGAC
GAATGAGCTCCACAGGTCACGGGCCATTAGCATTTGCAGG
TGGTCGCGAAAGGTCCTAAACTGGCGACCTATGGCCATTTTT
TCTGGGGTGATGCAGTAGAAGGTAAGCGGGTCTTGTTC
CCAGCGGTCCCATCCAAGGTTCGCGGCTAGGTCTCGCGCGG
CAGTCACTAGAGGCTCATCTCCGCCGAACTTCATGACCA
GCATGAAGGGCACGAGCTGCTTCCCAAAGGCCCCCATCCAA
GTATAGGTCTCTACATCGTAGGTGACAAAGAGACGCTCG
GTGCGAGGATGCGAGCCGATCGGGAAGAACTGGATCTCCC
GCCACCAATTGGAGGAGTGGCTATTGATGTGGTGAAAGTA
GAAGTCCCTGCGACGGGCCGAACACTCGTGCTGGCTTTTGT
AAAAACGTGCGCAGTACTGGCAGCGGTGCACGGGCTGTA
CATCCTGCACGAGGTTGACCTGACGACCGCGCACAAGGAAG
CAGAGTGGGAATTTGAGCCCCTCGCCTGGCGGGTTTGGC
TGGTGGTCTTCTACTTCGGCTGCTTGACCTTGACCGTCTGGC
TGCTCGAGGGGAGTTACGGTGGATCGGACCACCACGCC
GCGCGAGCCCAAAGTCCAGATGTCCGCGCGCGGCGGTCGG
AGCTTGATGACAACATCGCGCAGATGGGAGCTGTCCATGG
```

FIG.10E

```
TCTGGAGCTCCCGCGGCGTCAGGTCAGGCGGGAGCTCCTGC
AGGTTTACCTCGCATAGACGGGTCAGGGCGCGGGCTAGA
TCCAGGTGATACCTAATTTCCAGGGGCTGGTTGGTGGCGGC
GTCGATGGCTTGCAAGAGGCCGCATCCCCGCGGCGCGAC
TACGGTACCGCGCGGCGGGCGGTGGGCCGCGGGGGTGTCC
TTGGATGATGCATCTAAAAGCGGTGACGCGGGCGAGCCCC
CGGAGGTAGGGGGGGCTCCGGACCCGCCGGGAGAGGGGG
CAGGGGCACGTCGGCGCCGCGCGGGCAGGAGCTGGTGC
T
GCGCGCGTAGGTTGCTGGCGAACGCGACGACGCGGCGGTT
GATCTCCTGAATCTGGCGCCTCTGCGTGAAGACGACGGGC
CCGGTGAGCTTGAGCCTGAAAGAGAGTTCGACAGAATCAAT
TTCGGTGTCGTTGACGGCGGCCTGGCGCAAAATCTCCTG
CACGTCTCCTGAGTTGTCTTGATAGGCGATCTCGGCCATGAA
CTGCTCGATCTCTTCCTCCTGGAGATCTCCGCGTCCGG
CTCGCTCCACGGTGGCGGCGAGGTCGTTGGAAATGCGGGC
CATGAGCTGCGAGAAGGCGTTGAGGCCTCCCTCGTTCCAG
ACGCGGCTGTAGACCACGCCCCTTCGGCATCGCGGGCGCG
CATGACCACCTGCGCGAGATTGAGCTCCACGTGCCGGGC
GAAGACGGCGTAGTTTCGCAGGCGCTGAAAGAGGTAGTTGA
GGGTGGTTGGCGGTGTGTTCTGCCACGAAGAAGTACATAA
CCCAGCGTCGCAACGTGGATTCGTTGATATCCCCCAAGGCCT
CAAGGCGCTCCATGGCCTCGAGGAAGTCCAAGGCGAAG
TTGAAAAACTGGGAGTTGCGCGCCGACACGGTTAACTCCTC
CTCCAGAAGACGGATGAGCTCGGCGACAGTGTCGCGCAC
CTCGCGCTCAAAGGCTACAGGGGCCTCTTCTTCTTCTTCAAT
CTCCTCTTCCATAAGGGCCTCCCCTTCTTCTTCTTCTG
GCGGCGGTGGGGGAGGGGGGACACGGCGGCGACGACGGC
GCACCGGGAGGCGGTCGACAAAGCGCTTCGATCATCTCCCCG
CGGCGACGGCGCATGGTCTCGGTGACGGCGCGGCCGTTCT
CGCGGGGGCGCAGTTGGAAGACGCCGCCCGTCATGTCCCG
GTTATGGGTTGGCGGGGGCTGCCATGCGGCAGGGATACG
GCGCTAACGATGCATCTCAACAATTGTTGTGTAGGTACTC
CGCCGCCGAGGGACCTGAGCGAGTCCGCATCGACCGGATC
GGAAAACCTCTCGAGAAAGGCGTCTAACCAGTCACAGTCG
CAAGGTAGGCTGAGCACCGTGGCGGGCGGCAGCGGGCGGC
GGTCGGGGTTGTTTCTGGCGGAGGTGCTGCTGATGATGTA
ATTAAAGTAGGCGGTCTTGAGACGGCGGATGGTCGACAGAA
GCACCATGTCCTTGGGTCCGGCCTGCTGAATGCGCAGGC
GGTCGGCCATGCCCCAGGCTTCGTTTTGACATCGGCGCAGG
TCTTTGTAGTAGTCTTGCATGAGCCTTTCTACCGGCACT
TCTTCTTCTCCTTCCTCTTGTCCTGCATCTCTTGCATCTATCGC
TGCGGCGGCGGCGGAGTTTGGCCGTAGGTGGCGCCC
TCTTCCTCCCATGCGTGTGACCCCGAAGCCCCTCATCGGCTG
AAGCAGGGCTAGGCTGGCGACAACGCGCTCGGCTAATA
TGGCCTGCTGCACCTGCGTGAGGGTAGACTGGAAGTCATCC
```

FIG.10F

```
ATGTCCACAAAGCGGTGGTATGCGCCCGTGTTGATGGTG
TAAGTGCAGTTGGCCATAACGGACCAGTTAACGGTCTGGTG
ACCCGGCTGCGAGAGCTCGGTGTACCTGAGACGCGAGTA
AGCCCTCGAGTCAAATACGTAGTCGTTGCAAGTCCGCACCA
GGTACTGGTATCCCACCAAAAAGTGCGGCGGCGGCTGGC
GGTAGAGGGGCCAGCGTAGGGTGGCCGGGGCTCCGGGGG
CGAGATCTTCCAACATAAGGCGATGATAATCCGTAGATGTAC
CTGGACATCCAGGTGATGCCCGGCGGCGGTGGTGGAGGCGC
GCGGAAAGTCGCGGACGCGGTTCCAGATGTTGCGCAGCGG
CAAAAAGTGCTCCATGGTCGGGACGCTCTGGCCGGTCAGGC
GCGCGCAATCGTTGACGCTCTACCGTGCAAAAGGAGAGC
CTGTAAGCGGGCACTCTTCCGTGGTCTGGTGGATAAATTCGC
AAGGGTATCATGGCGGACGACCGGGGTTCGAGCCCCGT
ATCCGGCCGTCCGCCGTGATCCATGCGGTTACCGCCCGCGT
GTCGAACCCAGGTGTGCGACGTCAGACAACGGGGGAGTG
CTCCTTTTGGCTTCCTTCCAGGCGCGGCGGCTGCTGCGCTAG
CTTTTTTGGCCACTGGCCGCGCGCAGCGTAAGCGGTTA
GGCTGGAAAGCGAAAGCATTCCGTGGCTCGCTCCCTGTAGC
CGGAGGGTTATTTTCCAAGGGTTGAGTCGCGGGACCCCC
GGTTCGAGTCTCGGACCGGCCGGACTGCGGCGAACGGGGG
TTTGCCTCCCCGTCATGCAAGACCCCGCTTGCAAATTCCT
CCGGAAACAGGGACGAGCCCCTTTTTTGCTTTTCCCAGATGC
ATCCGGTGCTGCGGCAGATGCGCCCCCCTCCTCAGCAG
CGGCAAGAGCAAGAGCAGCGGCAGACATGCAGGGCACCCT
CCCCTCCTCCTACCGCGTCAGGAGGGGCGACATCCGCGGT
TGACGCGGCAGCAGATGGTGATTACGAACCCCGCGGCGCC
GGGCCCGGCACTACCTGGACTTGGAGGAGGGCGAGGGCC
TGGCGCGGCTAGGAGCGCCCTCTCCTGAGCGGTACCCAAGG
GTGCAGCTGAAGCGTGATACGCGTGAGGCGTACGTGCCG
AGGCAGAACCTGTTTCGCGACCGCGAGGGAGAGGAGCCCG
AGGAGATGCGGGATCGAAAGTTCCACGCAGGGCGCGAGCT
GCGGCATGGCCTGAATCGCGAGCGGTTGCTGCGCGAGGAT
GACTTTGAGCCCGACGCGCGAACCGGGATTAGTCCCGCGC
GCGCACACGTGGCGGCCGCCGACCTGGTAACCGCATACGA
GCAGACGGTGAACCAGGAGATTAACTTTCAAAAAAGCTTT
AACAACCACGTGCGTACGCTTGTGGCGCGCGAGGAGGTGG
CTATAGGACTGATGCATCTGTGGGACTTTGATTGCGCGCT
GGAGCAAAACCCAAATAGCAAGCCGCTCATGGCGCAGCTGT
TCCTTATAGTGCAGCACAGCAGGGACAACGAGGCATTCA
GGGATGCGCTGCTAAACATAGTAGAGCCCGAGGGCCGCTG
GCTGCTCGATTTGATAAACATCCTGCAGAGCATAGTGGTG
CAGGAGCGCAGCTTGAGCCTGGCTGACAAGGTGGCCGCCAT
CAACTATTCCATGCTTAGCCTGGGCAAGTTTTACGCCCG
CAAGATATACCATACCCCTTACGTTCCCATAGACAAGGAGGT
AAAGATCGAGGGGTTCTACATGCGCATGGCGCTGAAGG
TGCTTACCTTGAGCGACGACCTGGGCGTTTATCGCAACGAG
```

FIG.10G

```
CGCATCCACAAGGCCGTGAGCGTGAGCCGGCGGCGCGAG
CTCAGCGACCGCGAGCTGATGCACAGCCTGCAAAGGCCCT
GGCTGGCACGGGCAGCGGCGATAGAGAGGCCGAGTCCTA
CTTTGACGCGGCGCTGACCTGCGCTGGGCCCCAAGCCGAC
GCGCCTGGAGGCAGCTGGGGCCGGACCTGGGCTGGCGG
TGGCACCCGCGCGCGCTGGCAACGTCGGCGGCGTGGAGGA
ATATGACGAGGACGATGAGTACGAGCCAGAGGACGGCGAG
TACTAAGCGGTGATGTTTCTGATCAGATGATGCAAGACGCAA
CGGACCCGGCGGTGCGGGCGGCGCTGCAGAGCCAGCCG
TCCGGCCTTAACTCCACGGACGACTGGCGCCAGGTCATGGA
CCGCATCATGTCGCTGACTGCGCGCAATCCTGACGCGTT
CCGGCAGCAGCCGCAGGCCAACCGGCTCTCCGCAATTCTGG
AAGCGGTGGTCCCGGCGCGCGCAAACCCCACGCACGAGA
AGGTGCTGGCGATCGTAAACGCGCTGGCCGAAAACAGGGC
CATCCGGCCCGACGAGGCCGGCCTGGTCTACGACGCGCTG
CTTCAGCGCGTGGCTCGTTACAACAGCGGCAACGTGCAGAC
CAACCTGGACCGGGCTGGTGGGGGATGTGCGCGAGGCCGT
GGCGCAGCGTGAGCGCGCGCAGCAGCAGGGCAACCTGGGC
TCCATGGTTGCACTAAACGCCTTCCTGAGTACACAGCCCG
CCAACGTGCCGCGGGGACAGGAGGACTACACCAACTTTGTG
AGCGCACTGCGGCTAATGGTGACTGAGACACCGCAAAGT
GAGGTGTACCAGTCTGGGCCAGACTATTTTTTCCAGACCAGT
AGACAAGGCCTGCAGACCGTAAACCTGAGCCAGGCTTT
CAAAAACTTGCAGGGGCTGTGGGGGGTGCGGGCTCCCACA
GGCGACCGCGCGACCGTGTCTAGCTTGCTGACGCCCAACT
CGCGCCTGTTGCTGCTGCTAATAGCGCCCTTCACGGACAGT
GGCAGCGTGTCCCGGGACACATACCTAGGTCACTTGCTG
ACACTGTACCGCGAGGCCATAGGTCAGGCGCATGTGGACGA
GCATACTTTCCAGGCGCTTACAAGTGTCAGCCGCGCGCT
GGGGCAGGAGGACACGGGCAGCCTGGAGGCAACCCTAAAC
TACCTGCTGACCAACCGGCGGCAGAAGATCCCCTCGTTGC
ACAGTTTAAACAGCGAGGAGGAGCGCATTTTGCGCTACGTG
CAGCAGAGCGTGAGCCTTAACCTGATGCGCGACGGGGTA
ACGCCCAGCGTGGCGCTGGACATGACCGCGCGCAACATGG
AACCGGGCATGTATGCCTCAAACCGGCCGTTTATCAACCG
CCTAATGGACTACTTGCATCGCGCGGCCGCCGTGAACCCCG
AGTATTTCACCAATGCCATCTTGAACCCGCACTGGCTAC
CGCCCCTGGTTTCTACACCGGGGATTCGAGGTGCCCGAG
GGTAACGATGGATTCCTCTGGGACGACATAGACGACAGC
GTGTTTTCCCCGCAACCGCAGACCCTGCTAGAGTTGCAACAG
CGCGAGCAGGCAGAGGCGGCGCTGCGAAAGGAAAGCTT
CCGCAGGCCAAGCAGCTTGTCCGATCTAGGCGCTGCGGCCC
CGCGGTCAGATGCTAGTAGCCCATTTCCAAGCTTGATAG
GGTCTCTTACCAGCACTCGCACCACCCGCCCGCGCCTGCTG
GGCGAGGAGGAGTACCTAAACAACTCGCTGCTGCAGCCG
CAGCGCGAAAAAAACCTGCCTCCGGCATTTCCCAACAACGG
```

FIG.10H

```
GATAGAGAGCCTAGTGGACAAGATGAGTAGATGGAAGAC
GTACGCGCAGGAGCACAGGGACGTGCCAGGCCCGCGCCCG
CCCACCCGTCGTCAAAGGCACGACCGTCAGCGGGGTCTGG
TGTGGGAGGACGATGACTCGGCAGACGACAGCAGCGTCCT
GGATTTGGGAGGGAGTGGCAACCCGTTTGCGCACCTTCGC
CCCAGGCTGGGGAGAATGTTTTAAAAAAAAAAAAGCATGAT
GCAAATAAAAAACTCACCAAGGCCATGGCACCGAGCGT
TGGTTTTCTTGTATTCCCCTTAGTATGCGGCGCGCGGCGATG
TATGAGGAAGGTCCTCCTCCCTCCTACGAGAGTGTGGT
GAGCGCGGCGCCAGTGGCGGCGGCGCTGGGTTCTCCCTTC
GATGCTCCCCTGGACCCGCCGTTTGTGCCTCCGCGGTACC
TGCGGCCTACCGGGGGAGAAACAGCATCCGTTACTCTGAG
TTGGCACCCTATTCGACACCACCCGTGTGTACCTGGTG
GACAACAAGTCAACGGATGTGGCATCCCTGAACTACCAGAA
CGACCACAGCAACTTTCTGACCACGGTCATTCAAAACAA
TGACTACAGCCCGGGGGAGGCAAGCACACAGACCATCAATC
TTGACGACCGGTCGCACTGGGGCGGCGACCTGAAAACCA
TCCTGCATACCAACATGCCAAATGTGAACGAGTTCATGTTTA
CCAATAAGTTTAAGGCGCGGGTGATGGTGTCGCGCTTG
CCTACTAAGGACAATCAGGTGGAGCTGAAATACGAGTGGGT
GGAGTTCACGCTGCCCGAGGGCAACTACTCCGAGACCAT
GACCATAGACCTTATGAACAACGCGATCGTGGAGCACTACTT
GAAAGTGGGCAGACAGAACGGGGTTCTGGAAAGCGACA
TCGGGGTAAAGTTTGACACCCGCAACTTCAGACTGGGGTTT
GACCCCGTCACTGGTCTTGTCATGCCTGGGGTATATACA
AACGAAGCCTTCCATCCAGACATCATTTTGCTGCCAGGATGC
GGGGTGGACTTCACCCACAGCCGCCTGAGCAACTTGTT
GGGCATCCGCAAGCGGCAACCCTTCCAGGAGGGCTTTAGGA
TCACCTACGATGATCTGGAGGGTGGTAACATTCCCGCAC
TGTTGGATGTGGACGCCTACCAGGCGAGCTTGAAAGATGAC
ACCGAACAGGGCGGGGGTGGCGCAGGCGGCAGCAACAGC
AGTGGCAGCGGCGCGGAAGAGAACTCCAACGCGGCAGCCG
CGGCAATGCAGCCGGTGGAGGACATGAACGATCATGCCAT
TCGCGGCGACACCTTTGCCACACGGGCTGAGGAGAAGCGC
GCTGAGGCCGAAGCAGCGGCCGAAGCTGCCGCCCCCGCTG
CGCAACCCGAGGTCGAGAAGCCTCAGAAGAAACCGGTGATC
AAACCCCTGACAGAGGACAGCAAGAAACGCAGTTACAAC
CTAATAAGCAATGACAGCACCTTCACCCAGTACCGCAGCTGG
TACCTTGCATACAACTACGGCGACCCTCAGACCGGAAT
CCGCTCATGGACCCTGCTTTGCACTCCTGACGTAACCTGCGG
CTCGGAGCAGGTCTACTGGTCGTTGCCAGACATGATGC
AAGACCCCGTGACCTTCCGCTCCACGCGCCAGATCAGCAAC
TTTCCGGTGGTGGGCGCCGAGCTGTTGCCCGTGCACTCC
AAGAGCTTCTACAACGACCAGGCCGTCTACTCCCAACTCATC
CGCCAGTTTACCTCTCTGACCCACGTGTTCAATCGCTT
TCCCGAGAACCAGATTTTGGCGCGCCCGCCAGCCCCCACCA
```

FIG.10I

```
TCACCACCGTCAGTGAAAACGTTCCTGCTCTCACAGATC
ACGGGACGCTACCGCTGCGCAACAGCATCGGAGGAGTCCA
GCGAGTGACCATTACTGACGCCAGACGCCGCACCTGCCCC
TACGTTTACAAGGCCCTGGGCATAGTCTCGCCGCGCGTCCTA
TCGAGCCGCACTTTTTGAGCAAGCATGTCCATCCTTAT
ATCGCCCAGCAATAACACAGGCTGGGGCCTGCGCTTCCCAA
GCAAGATGTTTGGCGGGGCCAAGAAGCGCTCCGACCAAC
ACCCAGTGCGCGTGCGCGGGCACTACCGCGCGCCCTGGGG
CGCGCACAAACGCGGCCGCACTGGGCGCACCACCGTCGAT
GACGCCATCGACGCGGTGGTGGAGGAGGCGCGCAACTACA
CGCCCACGCCGCCACCAGTGTCCACAGTGGACGCGGCCAT
TCAGACCGTGGTGCGCGGAGCCCGGCGCTATGCTAAAATGA
AGAGACGGCGGAGGCGCGTAGCACGTCGCCACCGCCGCC
GACCCGGCACTGCCGCCCAACGCGCGGCGGCGGCCCTGCT
TAACCGCGCACGTCGCACCGGCCGACGGGCGGCCATGCGG
GCCGCTGCAAGGCTGGCCGCGGGTATTGTCACTGTGCCCCC
CAGGTCCAGGCGACGAGCGGCCGCCGCAGCAGCCGCGGC
CATTAGTGCTATGACTCAGGGTCGCAGGGGCAACGTGTATT
GGGTGCGCGACTCGGTTAGCGGCCTGCGCGTGCCCGTGC
GCACCCGCCCCCGCGCAACTAGATTGCAAGAAAAACTAC
TTAGACTCGTACTGTTGTATGTATCCAGCGGCGGCGGCG
CGCAACGAAGCTATGTCCAAGCGCAAAATCAAAGAAGAGAT
GCTCCAGGTCATCGCGCCGGAGATCTATGGCCCCCCGAA
GAAGGAAGAGCAGGATTACAAGCCCCGAAAGCTAAAGCGG
GTCAAAAAGAAAAAGAAAGATGATGATGATGAACTTGACG
ACGAGGTGGAACTGCTGCACGCTACCGCGCCCAGGCGACG
GGTACAGTGGAAAGGTCGACGCGTAAAACGTGTTTTGCGA
CCCGGCACCACCGTAGTCTTTACGCCCGGTGAGCGCTCCAC
CCGCACCTACAAGCGCGTGTATGATGAGGTGTACGGCGA
CGAGGACCTGCTTGAGCAGGCCAACGAGCGCCTCGGGGAG
TTTGCCTACGGAAAGCGGCATAAGGACATGCTGGCGTTGC
CGCTGGACGAGGGCAACCCAACACCTAGCCTAAAGCCCGTA
ACACTGCAGCAGGTGCTGCCCGCGCTTGCACCGTCCGAA
GAAAAGCGCGGCCTAAAGCGCGAGTCTGTTGACTTGGCACC
CACCGTGCAGCTGATGGTACCCAAGCGCCAGCGACTGGA
AGATGTCTTGGAAAAAATGACCGTGGAACCTGGGCTGGAGC
CCGAGGTCCGCGTGCGGCCAATCAAGCAGGTGGCGCCGG
GACTGGGCGTGCAGACCGTGGACGTTCAGATACCCACTACC
AGTAGCACCAGTATTGCCACCGCCACAGAGGGCATGGAG
ACACAAACGTCCCCGGTTGCCTCAGCGGTGGCGGATGCCGC
GGTGCAGGCGGTCGCTCCGGCCGCGTCCAAGACCTCTAC
GGAGGTGCAAACGGACCCGTGGATGTTTCGCGTTTCAGCCC
CCCGGCGCCCGCGCGGTTCGAGGAAGTACGGCGCCGCCA
GCGCGCTACTGCCCGAATATGCCCTACATCCTTCCATTGCGC
CTACCCCGGCTATCGTGGCTACACCTACCGCCCCAGA
AGACGAGCAACTACCCGACGCCGAACCACCACTGGAACCCG
```

FIG.10J

```
CCGCCGCCGTCGCCGTCGCCAGCCCGTGCTGGCCCCGAT
TTCCGTGCGCAGGGTGGCTCGCGAAGGAGGCAGGACCCTG
GTGCTGCCAACAGCGCGCTACCACCCCAGCATCGTTTAAA
AGCCGGTCTTTGTGGTTCTTGCAGATATGGCCCTCACCTGCC
GCCTCCGTTTCCCGGTGCCGGGATTCCGAGGAAGAATG
CACCGTAGGAGGGGCATGGCCGGCCACGGCCTGACGGGCG
GCATGCGTCGTGCGCACCACCGGCGGCGGCGCGCGTCGCA
CCGTCGCATGCGCGGCGGTATCCTGCCCCTCCTTATTCCACT
GATCGCCGCGGCGATTGGCGCCGTGCCCGGAATTGCAT
CCGTGGCCTTGCAGGCGCAGAGACACTGATTAAAAACAAGT
TGCATGTGGGAAAAATCAAAATAAAAAGTCTGGACTCTCA
CGCTCGCTTGGTCCTGTAACTATTTTGTAGAATGGAAGACAT
CAACTTTGCGTCTCTGGCCCCGCGACACGGCTCGCGCC
CGTTCATGGGAAACTGGCAAGATATCGGCACCAGCAATATG
AGCGGTGGCGCCTTCAGCTGGGCTCGCTGTGGAGCGGC
ATTAAAAATTTCGGTTCCACCGTTAAGAACTATGGCAGCAAG
GCCTGGAACAGCAGCACAGGCCAGATGCTGAGGGATAA
GTTGAAAGAGCAAAATTTCCAACAAAAGGTGGTAGATGGCC
TGGCCTCTGGCATTAGCGGGGTGGTGGACCTGGCCAACC
AGGCAGTGCAAAATAAGATTAACAGTAAGCTTGATCCCCGCC
CTCCCGTAGAGGAGCCTCCACCGGCCGTGGAGACAGTG
TCTCCAGCGGGGCGTGGCGAAAAGCGTCCGCGCCCCGACA
GGGAAGAAACTCTGGTGACGCAAATAGACGAGCCTCCCTC
GTACGAGGAGGCACTAAAGCAAGGCCTGCCCACCACCCGTC
CCATCGCGCCCATGGCTACCGGAGTGCTGGGCCAGCACA
CACCCGTAACGCTGGACCTGCCTCCCCCGCCGACACCCAG
CAGAAACCTGTGCTGCCAGGCCCGACCGCCGTTGTTGTA
ACCCGTCCTAGCCGCGCGTCCCTGCGCCGCGCCGCCAGCGG
TCCGCGATCGTTGCGGCCCGTAGCCAGTGGCAACTGGCA
AAGCACACTGAACAGCATCGTGGGTCTGGGGGTGCAATCCC
TGAAGCGCCGACGATGCTTCTGAATAGCTAACGTGTCGT
ATGTGTGTCATGTATGCGTCCATGTCGCCGCCAGAGGAGCT
GCTGAGCCGCCGCGCGCCCGCTTTCCAAGATGGCTACCC
CTTCGATGATGCCGCAGTGGTCTTACATGCACATCTCGGGCC
AGGACGCCTCGGAGTACCTGAGCCCCGGCTGGTGCAG
TTTGCCCGCGCCACCGAGACGTACTTCAGCCTGAATAACAAG
TTTAGAAACCCCACGGTGGCGCCTACGCACGACGTGAC
CACAGACCGGTCCCAGCGTTTGACGCTGCGGTTCATCCCTGT
GGACCGTGAGGATACTGCGTACTCGTACAAGGCGCGGT
TCACCCTAGCTGTGGGTGATAACCGTGTGCTGGACATGGCTT
CCACGTACTTTGACATCCGCGGCGTGCTGGACAGGGC
CCTACTTTTAAGCCCTACTCTGGCACTGCCTACAACGCCCTG
GCTCCCAAGGGTGCCCCAAATCCTTGCGAATGGGATGA
AGCTGCTACTGCTCTTGAAATAAACCTAGAAGAAGAGGACG
ATGACAACGAAGACGAAGTAGACGAGCAAGCTGAGCAGC
AAAAAACTCACGTATTTGGGCAGGCGCCTTATTCTGGTATAA
```

FIG.10K

ATATTACAAAGGAGGGTATTCAAATAGGTGTCGAAGGT
CAAACACCTAAATATGCCGATAAACATTTCAACCTGAACCT
CAAATAGGAGAATCTCAGTGGTACGAAACTGAAATTAA
TCATGCAGCTGGGAGAGTCCTTAAAAAGACTACCCCAATGAA
ACCATGTTACGGTTCATATGCAAAACCCACAAATGAAA
ATGGAGGGCAAGGCATTCTTGTAAAGCAACAAAATGGAAAG
CTAGCCCGTCAAGTGGAAATGCAATTTTTCTCAACTACT
GAGGCGACCGCAGGCAATGGTGATAACTTGACTCCTAAAGT
GGTATTGTACAGTGAAGATGTAGATATAGAAACCCCAGA
CACTCATATTTCTTACATGCCCACTATTAAGGAAGGTAACTCA
CGAGAACTAATGGGCCAACAATCTATGCCCAACAGGC
CTAATTACATTGCTTTTAGGGACAATTTTATTGGTCTAATGTA
TTACAACAGCACGGGTAATATGGGTGTTCTGGCGGGC
CAAGCATCGCAGTTGAATGCTGTTGTAGATTTGCAAGACAGA
AACACAGAGCTTTCATACCAGCTTTTGCTTGATTCCAT
TGGTGATAGAACCAGGTACTTTTCTATGTGGAATCAGGCTGT
TGACAGCTATGATCCAGATGTTAGAATTATTGAAAATC
ATGGAACTGAAGATGAACTTCCAAATTACTGCTTTCCACTGG
GAGGTGTATTAATACAGAGACTCTTACCAAGGTAAAA
CCTAAAACAGGTCAGGAAAATGGATGGGAAAAGATGCTAC
AGAATTTTCAGATAAAAATGAAATAAGAGTTGGAAATAA
TTTTGCCATGGAAATCAATCTAAATGCCAACCTGTGGAGAAA
TTTCCTGTACTCCAACATACGCGTGTATTTGCCCGACA
AGCTAAAGTACAGTCCTTCCAACGTAAAAATTTCTGATAACC
CAAACACCTACGACTACATGAACAAGCGAGTGGTGGCT
CCCGGGTTAGTGGACTGCTACATTAACCTTGGAGCACGCTG
GTCCCTTGACTATATGGACAACGTCAACCCATTTAACCA
CCACCGCAATGCTGGCCTGCGCTACCGCTCAATGTTGCTGG
GCAATGGTCGCTATGTGCCCTTCCACATCCAGGTGCCTC
AGAAGTTCTTTGCCATTAAAAACCTCCTTCTCCTGCCGGGCT
CATACACCTACGAGTGGAACTTCAGGAAGGATGTTAAC
ATGGTTCTGCAGAGCTCCCTAGGAAATGACCTAAGGGTTGA
CGGAGCCAGCATTAAGTTTGATAGCATTTGCCTTTACGC
CACCTTCTTCCCCATGGCCCACAACACCGCCTCCACGCTTGA
GGCCATGCTTAGAAACGACACCAACGACCAGTCCTTTA
ACGACTATCTCTCCGCCGCCAACATGCTCTACCCTATACCCG
CCAACGCTACCAACGTGCCCATATCCATCCCCTCCCGC
AACTGGGCGGCTTTCGCGGCTGGGCCTTCACGCGCCTTAA
GACTAAGGAAACCCCATCACTGGGCTCGGGCTACGACCC
TTATTACACCTACTCTGGCTCTATACCCTACCTAGATGGAACC
TTTTACCTCAACCACACCTTTAAGAAGGTGGCCATTA
CCTTTGACTCTTCTGTCAGCTGGCCTGGCAATGACCGCCTGC
TTACCCCCAACGAGTTTGAAATTAAGCGCTCAGTTGAC
GGGGAGGGTTACAACGTTGCCCAGTGTAACATGACCAAAGA
CTGGTTCCTGGTACAAATGCTAGCTAACTACAACATTGG
CTACCAGGGCTTCTATATCCCAGAGAGCTACAAGGACCGCAT

FIG.10L

```
GTACTCCTTCTTTAGAAACTTCCAGCCCATGAGCCGTC
AGGTGGTGGATGATACTAAATACAAGGGACTACCAACAGGTG
GGCATCCTACACCAACACAACAACTCTGGATTTGTTGGC
TACCTTGCCCCCACCATGCGCGAAGGACAGGCCTACCCTGC
TAACTTCCCCTATCCGCTTATAGGCAAGACCGCAGTTGA
CAGCATTACCCAGAAAAGTTTCTTTGCGATCGCACCCTTTG
GCGCATCCCATTCTCCAGTAACTTTATGTCCATGGGCG
CACTCACAGACCTGGGCCAAAACCTTCTCTACGCCAACTCCG
CCCACGCGCTAGACATGACTTTTGAGGTGGATCCCATG
GACGAGCCCACCCTTCTTTATGTTTTGTTTGAAGTCTTTGACG
TGGTCCGTGTGCACCGGCCGCACCGCGGCGTCATCGA
AACCGTGTACCTGCGCACGCCCTTCTCGGCCGGCAACTCCA
CAACATAAAGAAGCAAGCAACATCAACAACAGCTGCCGC
CATGGGCTCCAGTGAGCAGGAACTGAAAGCCATTGTCAAAG
ATCTTGGTTGTGGGCCATATTTTTTGGGCACCTATGACA
AGCGCTTTCCAGGCTTTGTTTCTCCACACAAGCTCGCCTGCG
CCATAGTCAATACGGCCGGTCGCGAGACTGGGGGCGTA
CACTGGATGGCCTTTGCCTGGAACCCGCACTCAAAAACATGC
TACCTCTTTGAGCCCTTGGCTTTTCTGACCAGCGACT
CAAGCAGGTTTACCAGTTTGAGTACGAGTCACTCCTGCGCCG
TAGCGCCATTGCTTCTTCCCCCGACCGCTGTATAACGC
TGGAAAAGTCCACCCAAAGCGTACAGGGGCCCAACTCGGCC
GCCTGTGGACTATCTGCTGCATGTTTCTCCACGCCTTT
GCCAACTGGCCCCAAACTCCCATGGATCACAACCCCACCATG
AACCTTATTACCGGGGTACCCAACTCCATGCTCAACAG
TCCCCAGGTACAGCCCACCCTGCGTCGCAACCAGGAACAGC
TCTACAGCTTCCTGGAGCGCCACTCGCCCTACTTCGCA
GCCACAGTGCGCAGATTAGGAGCGCCACTTCTTTTTGTCACT
TGAAAAACATGTAAAAATAATGTACTAGAGACACTTTC
AATAAAGGCAAATGCTTTTATTTGTACACTCTCGGGTGATTAT
TTACCCCCACCCTTGCCGTCTGCGCCGTTTAAAAATC
AAAGGGGTTCTGCCGCGCATCGCTATGCGCCACTGGCAGGG
ACACGTTGCGATACTGGTGTTTAGTGCTCCACTTAAACT
CAGGCACAACCATCCGCGGCAGCTCGGTGAAGTTTTCACTC
CACAGGCTGCGCACCATCACCAACGCGTTTAGCAGGTCG
GGCGCCGATATCTTGAAGTCGCAGTTGGGGCCTCCGCCCTG
CGCGCGCGAGTTGCGATACACAGGGTTGCAGCACTGGAA
CACTATCAGCGCCGGGTGGTGCACGCTGGCCAGCACGCTCT
TGTCGGAGATCAGATCCGCGTCCAGGTCCTCCGCGTTGC
TCAGGGCGAACGGAGTCAACTTTGGTAGCTGCCTTCCCAAA
AAGGGCGCGTGCCCAGGCTTTGAGTTGCACTCGCACCGT
AGTGGCATCAAAAGGTGACCGTGCCCGGTCTGGGCGTTAGG
ATACAGCGCCTGCATAAAAGCCTTGATCTGCTTAAAAGC
CACCTGAGCCTTTGCGCCTTCAGAGAAGAACATGCCGCAAG
ACTTGCCGGAAAACTGATTGGCCGGACAGGCCGCGTCGT
GCACGCAGCACCTTGCGTCGGTGTTGGAGATCTGCACCACA
```

FIG.10M

```
TTTCGGCCCCACCGGTTCTTCACGATCTTGGCCTTGCTA
GACTGCTCCTTCAGCGCGCGCTGCCCGTTTTCGCTCGTCACA
TCCATTTCAATCACGTGCTCCTTATTTATCATAATGCT
TCCGTGTAGACACTTAAGCTCGCCTTCGATCTCAGCGCAGCG
CTGCAGCCACAACGCGCAGCCCGTGGGCTCGTGATGCT
TGTAGGTCACCTCTGCAAACGACTGCAGGTACGCCTGCAGG
AATCGCCCATCATCGTCACAAAGGTCTTGTTGCTGGTG
AAGGTCAGCTGCAACCCGCGGTGCTCCTCGTTCAGCCAGGT
CTTGCATACGGCCGCCAGAGCTTCCACTTGGTCAGGCAG
TAGTTTGAAGTTCGCCTTTAGATCGTTATCCACGTGGTACTTG
TCCATCAGCGCGCGCAGCCTCCATGCCCTTCTCCC
ACGCAGACACGATCGGCACACTCAGCGGGTTCATCACCGTA
ATTTCACTTTCCGCTTCGCTGGGCTCTTCCTCTTCCTCT
TGCGTCCGCATACCACGCGCCACTGGGTCGTCTTCATTCAGC
CGCCGCACTGTGCGCTTACCTCCTTTGCCATGCTTGAT
TAGCACCGGTGGGTTGCTGAAACCCACCATTTGTAGCGCCA
CATCTTCTCTTTCTTCCTCGCTGTCCACGATTACCTCTG
GTGATGGCGGGCGCTCGGGCTTGGGAGAAGGGCGCTTCTTT
TTCTTCTTGGGCGCAATGGCCAAATCCGCCGCCGAGGTC
GATGGCCGCGGGCTGGGTGTGCGCGGCACCAGCGCGTCTT
GTGATGAGTCTTCCTCGTCCTCGGACTCGATACGCCGCCT
CATCCGCTTTTTTGGGGGCGCCCGGGGAGGCGGCGGCGAC
GGGGACGGGGACGACACGTCCTCCATGGTTGGGGACGTC
GCGCCGCACCGCGTCCGCGCTCGGGGGTGGTTTCGCGCTG
CTCCTCTTCCCGACTGGCCATTTCCTTCTCCTATAGGCAG
AAAAAGATCATGGAGTCAGTCGAGAAGAAGGACAGCCTAAC
CGCCCCCTCTGAGTTCGCCACCACCGCCTCCACCGATGC
CGCCAACGCGCCTACCACCTTCCCCGTCGAGGCACCCCCGC
TTGAGGAGGAGGAAGTGATTATCGAGCAGGACCCAGGTT
TTGTTAAGCGAAGACGACGAGGACCGCTCAGTACCAACAGAG
GATAAAAAGCAAGACCAGGACAACGCAGAGGCAAACGAG
GAACAAGTCGGGCGGGGGACGAAAGGCATGGCGACTACC
TAGATGTGGGAGACGACGTGCTGTTGAAGCATCTGCAGCG
CCAGTGCGCCATTATCTGCGACGCGTTGCAAGAGCGCAGCG
ATGCTGCCCCTCGCCATAGCGGATGTCAGCCTTGCCCTACG
AACGCCACCTATTCTCACCGCGCGTACCCCCAAACGCCAAG
AAACGGCACATGCGAGCCCAACCCGCCCTCAACTTC
TACCCGTATTTGCCGTGCCAGCGGTGCTTGCCACCTATCAC
ATCTTTTTCCAAAACTGCAAGATACCCCTATCCTGCCG
TGCCAACCGCAGCCGAGAGACAAGCAGCTGGCCTTGCGG
CAGGGCGCTGTCATACCTGATATCGCCTCGCTCAACGAAG
TGCCAAAAATCTTTGAGGGTCTTGGACGCGACGAGAAGCGC
GCGGCAAACGCTCTGCAACAGGAAAACAGCGAAAATGAA
AGTCACTGGAGTGTTGGTGGAACTCGAGGGTGACAACGC
GCGCCTAGCCGTACTAAAACGCAGCATCGAGGTCACCCA
CTTTGCCTACCCGGCACTTAACCTACCCCCCAAGGTCATGAG
```

FIG.10N

```
CACAGTCATGAGTGAGCTGATCGTGCGCCGTGCGCAGC
CCCTGGAGAGGGATGCAAATTTGCAAGAACAAACAGAGGAG
GGCCTACCCGCAGTTGGCGACGAGCAGCTAGCGCGCTGG
CTTCAAACGCGCGAGCCTGCCGACTTGGAGGAGCGACGACGCAA
ACTAATGATGGCCGCAGTGCTCGTTACCGTGGAGCTTGA
GTGCTGCAGCGGTTCTTTGCTGACCCGGAGATGCAGCGCA
AGCTAGAGGAAACATTGCACTACACCTTTCGACAGGGCT
ACGTACGCCAGGCCTGCAAGATCTCCAACGTGGAGCTCTGC
AACCTGGTCTCCTACCTTGGAATTTTGCACGAAAACCGC
CTTGGGCAAAACGTGCTTCATTCCACGCTCAAGGGCGAGGC
GCGCCGCGACTACGTCCGCGACTGCGTTTACTTATTTCT
ATGCTACACCTGGCAGACGGCCATGGGCGTTTGGCAGT
GCTTGGAGGAGTGCAACCTTCAAGGAGCTGCAGAAACTGC
TAAAGCAAAACTTGAAGGACCTATGGACGGCCTTCAACGAG
CGCTCCGTGGCCGCGCACCTGGCGGACATCATTTTCCCC
GAACGCCTGCTTAAAACCCTGCAACAGGGTCTGCCAGACTTC
ACCAGTCAAAGCATGTTGCAGAACTTTAGGAACTTTAT
CCTAGAGCGCTCAGGAATCTTGCCCGCCACCTGCTGTGCACT
TCCTAGCGACTTTGTGCCCATTAAGTACCGCGAATGCC
CTCCGCCGCTTTGGGGCCACTGCTACCTTCTGCAGCTAGCCA
ACTACCTTGCCTACCACTCTGACATAATGGAAGACGTG
AGCGGTGACGGTCTACTGGAGTGTCACTGTCGCTGCAACCT
ATGVAVVVVGVAVVGVTVVVTGGTTTGVAATTVGVAGVT
GCTTAACGAAAGTCAAATTATCGGTACCTTTGAGCTGCAGGG
TCCCTCGCCTGACGAAAAGTCCGCGGCTCCGGGGTTCA
AACTCACTCCGGGGCTGTGGACGTCGGCTTACCTTCGCAAAT
TTGTACCTGAGGACTACCACGCCCACGAGATTAGGTTC
TACGAAGACCAATCCCGCCCGCCAAATGCGGAGCTTACCGC
CTGCGTCATTACCCAGGGCCACATTCTTGGCCAATTGCA
AGCCATCAACAAAGCCCGCCAAGAGTTTCTGCTACGAAAGG
GACGGGGGGTTTACTTGGACCCCAGTCCGGCGAGGAGC
TCAACCCAATCCCCCCGCCGCCGCAGCCCTATCAGCAGCAG
CCGCGGGCCCTTGCTTCCAGGATGGCACCCAAAAAGAA
GCTGCAGCTGCCGCCGCCACCCACGGACGAGGAGGAATACT
GGGACAGTCAGGCAGAGGAGGTTTTGGACGAGGAGGAGG
AGGACATGATGGAAGACTGGGAGAGCCTAGACGAGGAAGC
TTCCGAGGTCGAAGAGGTGTCAGACGAAACACCGTCACCC
TCGGTCGCATTCCCCTCGCCGGCGCCCCAGAAATCGGCAAC
CGGTTCCAGCATGGCTACAACCTCCGCTCCTCAGGCGCC
GCCGGCACTGCCCGTTCGCCGACCCAACCGTAGATGGGACA
CCACTGGAACCAGGGCCGGTAAGTCCAAGCAGCCGCCGC
CGTTAGCCCAAGAGCAACAACAGCGCCAAGCTACCGCTCA
TGGCGCGGGCACAAGAACGCCATAGTTGCTTGCCTTGCAA
GACTGTGGGGCAACATCTCCTTCGCCCGCCGCTTTCTTCTC
TACCATCACGGCGTGGCCTTCCCCCGTAACATCCTGCA
TTACTACCGTCATCTCTACAGCCCATACTGCACCGGCGGCAG
```

FIG.100

CGGCAGCGGCAGCAACAGCAGCGGCCACACAGAAGCAA
AGGCGACCGGATAGCAAGACTCTGACAAAGCCCAAGAAATC
CACAGCGGCGGCAGCAGCAGGAGGAGGAGCGCTGCGTCT
GGCGCCCAACGAACCCGTATCGACCCGCGAGCTTAGAAACA
GGATTTTTCCCACTCTGTATGCTATATTTCAACAGAGCA
GGGGCCAAGAACAAGAGCTGAAAATAAAAAACAGGTCTCTG
CGATCCCTCACCCGCAGCTGCCTGTATCACAAAGCGAA
GATCAGCTTCGGCGCACGCTGGAAGACGCGGAGGCTCTCTT
CAGTAAATACTGCGCGCTGACTCTTAAGGACTAGTTTCG
CGCCCTTTCTCAAATTTAAGCGCGAAAACTACGTCATCTCCA
GCGGCCACACCCGGCGCCAGCACCTGTCGTCAGCGCCA
TTATGAGCAAGGAAATTCCCACGCCCTACATGTGGAGTTACC
AGCCACAAATGGGACTTGCGGCTGGAGCTGCCCAAGAC
TACTCAACCCGAATAAACTACATGAGCGCGGGACCCCACAT
GATATCCCGGGTCAACGGAATCCGCGCCCACCGAAACCG
AATTCTCTTGGAACAGGCGGCTATTACCACCACACCTCGTAA
TAACCTTAATCCCCGTAGTTGGCCCGCTGCCCTGGTGT
ACCAGGAAAGTCCCGCTCCCACCACTGTGGTACTTCCCAGA
GACGCCCAGGCCGAAGTTCAGATGACTAACTCAGGGGCG
CAGCTTGCGGGCGGCTTTCGTCACAGGGTGCGGTCGCCCGG
GCAGGGTATAACTCACCTGACAATCAGAGGGCGAGGTAT
TCAGCTCAACGACGAGTCGGTGAGCTCCTCGCTTGGTCTCC
GTCCGGACGGGACATTTCAGATCGGCGGCGCCGGCCGTC
GTTCATTCACGCCTCGTCAGGCAATCCTAACTCTGCAGACCT
CGTCCTCTGAGCCGCGCTCTGGAGGCATTGGAACTCTG
CATTTATTGAGGAGTTTGTGCATCGGTCTACTTTAACCCCT
TCTCGGGACCTCCCGGCCACTATCCGGATCAATTTAT
TCCTAACTTTGACGCGGTAAAGGACTCGGCGGACGGCTACG
ACTGAATGTTAAGTGGAGAGGCAGAGCAACTGCGCCTGA
AACACCTGGTCCACTGTCGCCGCCACAAGTGCTTTGCCCGC
GACTCCGGTGAGTTTTGCTACTTTGAATTGCCCGAGGAT
CATATCGAGGGCCCGGCGCACGGCGTCCGGCTTACCGCCCA
GGGAGAGCTTGCCCGTAGCCTGATTCGGGAGTTTACCCA
GCGCCCCTGCTAGTTGAGCGGGACAGGGGACCCTGTGTTC
TCACTGTGATTTGCAACTGTCCTAACCTTGGATTACATC
AAGATCTTTGTTGCCATCTCTGTGCTGAGTATAATAAATACAG
AAATTAAAATATACTGGGGCTCCTATCGCCATCCTGT
AAACGCCACCGTCTTCACCCGCCCAAGCAAACCAAGGCGAA
CCTTACCTGGTACTTTTAACATCTCTCCTCTGTGATTT
ACAACAGTTTCAACCCAGACGGAGTGAGTCTACGAGAGAAC
CTCTCCGAGCTCAGCTACTCCATCAGAAAAAACACCACC
CTCTCCGAGCTCAGCTACTCCATCAGAAAAAACACCACC
CTCCTTACCTGCCGGGAACGTACGAGTGCGTCACCGGCCGC
TGCACCACACCTACCGCCTGACCGTAAACCAGACTTTTT
CCGGACAGACCTCAATAACTCTGTTTACCAGAACAGGAGGT
GAGCTTAGAAAACCCTTAGGGTATTAGGCCAAAGGCGCA

FIG.10P

```
GCTACTGTGGGGTTTATGAACAATTCAAGCAACTCTACGGGC
TATTCTAATTCAGGTTTCTCTAATCGGGGTTGGGGTTA
TTCTCTGTCTTGTGATTCTCTTTATTCTTATACTAACGCTTCTC
TGCCTAAGGCTCGCCGCCTGCTGTGTGCACATTTGC
ATTTATTGTCAGCTTTTTAAACGCTGGGGTCGCCACCCAAGA
TGATTAGGTACATAATCCTAGGTTTACTCACCCTTGCG
TCAGCCCACGGTACCACCCAAAAGGTGGATTTTAAGGAGCC
AGCCTGTAATGTTACATTCGCAGCTGAAGCTATGAGTG
CACCACTCTTATAAAATGCACCACAGAACATGAAAAGCTGCT
TATTCGCCACAAAAACAAAATTGGCAAGTATGCTGTTT
ATGCTATTTGGCAGCCAGGTGACACTACAGAGTATAATGTTA
CAGTTTTCCAGGGTAAAAGTCATAAAACTTTTATGTAT
ACTTTTCCATTTTATGAAATGTGCTACATTACCATGTACATGA
GCAAACAGTATAAGTTGTGGCCCCACAAAATTGTGT
GGAAAACACTGGCACTTTCTGCTGCACTGCTATGCTAATTAC
AGTGCTCGCTTTGGTCTGTACCCTACTCTATATTAAAT
ACAAAAGCAGGACGCAGCTTTATTGAGGAAAGAAAATGCCTT
AATTTACTAAGTTACAAAGCTAATGTCACCACTAACTG
CTTTACTCGCTGCTTGCAAAACAAATTCAAAAAGTTAGCATTA
TAATTAGAATAGGATTTAAACCCCCGGTCATTTCCT
GCTCAATACCATTCCCTGAACAATTGACTCTATGTGGGATA
TGCTCCAGCGCTACAACCTTGAAGTCAGGCTTCCTGGA
TGTCAGCATCTGACTTTGGCCAGCACCTGTCCCGCGGATTTG
TTCCAGTCCAACTACAGCGACCCACCCTAACAGAGATG
ACCAACACAACCAACGCGGCCGCCGCTACCGGACTTACATC
TACCACAAATACACCCCAAGTTTCTGCCCTTTGTCAATAA
CTGGGATAACTTGGGCATGTGGTGGTTCTCCATAGCGCTTAT
GTTTGTATGCCTTATTATGTGGCTCATCTGCTGCC
TAAAGCGCAAACGCGCCCGACCACCCATCTATCGTCCCATCA
TTGTGCTACACCCAAACAATGATGGAATCCATAGATTG
GACGGACTGAAACACATGTTCTTTTCTCTTACAGTATGATTAA
ATGAGACATGATTCCTCGAGTTTTTATATTACTGACC
CTTGTTGCGCTTTTTTGTGCGTGCTCCACATTGGCTGCGGTTT
CTCACATCGAAGTAGACTGCATTCCAGCCTTCACAGT
CTATTTGCTTTACGGATTTGTCACCCTCACGCTCATCTGCAGC
CTCATCACTGTGGTCATCGCCTTTATCCAGTGCATTG
ACTGGGTCTGTGTGCGCTTTGCATATCTCAGACACCATCCCC
AGTACAGGGACAGGACTATAGCTGAGCTTCTTAGCCCT
GGACGGAATTATTACAGAGCAGCGCCTGCTAGAAAGACGCA
GGGCAGCGGCCGAGCAACAGCGCATGAATCAAGAGCTCC
AAGACATGGTTAACTTGCACCAGTGCAAAAGGGGTATCTTTT
GTCTGGTAAAGCAGGCCAAAGTCACCTACGACAGTAAT
ACCACCGGACACCGCCTTAGCTACAAGTTGCCAACCAAGCG
TCAGAAATTGGTGGTCATGGTGGGAGAAAAGCCCATTAC
CATAACTCAGCACTCGGTAGAAACCGAAGGCTGCATTCACTC
ACCTTGTCAAGGACCTGAGGATCTCTGCACCCTTATTA
```

FIG.10Q

```
AGACCCTGTGCGGTCTCAAAGATCTTATTCCCTTTAACTAATA
AAAAAAAATAATAAAGCATCACTTACTTAAAATCAGT
TAGCAAATTTCTGTCCAGTTTATTCAGCAGCACCTCCTTGCCC
TCCTCCCAGCTCTGGTATTGCAGCTTCCTCCTGGCTG
CAAACTTTCTCCACAATCTAAATGGAATGTCAGTTTCCTCCTG
TTCCTGTCCATCCGCACCCACTATCTTCATGTTGTTG
CAGATGAAGCGCGCAAGACCGTCTGAAGATACCTTCAACCC
CGTGTATCCATATGACACGGAAACCGGTCCTCCAACTGT
GCCTTTTCTTACTCCTCCCTTTGTATCCCCCAATGGGTTTCAA
GAGAGTCCCCCTGGGGTACTCTCTTTGCGCCTATCCG
AACCTCTAGTTACCTCCAATGGCATGCTTGCGCTCAAAATGG
GCAACGGCCTCTCTCTGGACGAGGCCGGCAACCTTACC
TCCCAAAATGTAACCACTGTGAGCCCCACCTGTGAAAAAACC
AAGTCAAACATAAACCTGGAAATATCTGCACCCCTCAC
AGTTACCTCAGAAGCCCTAACTGTGGCTGCCGCCGCACCTCT
AATGGTCGCGGGCAACACACTCACCATGCAATCACAGG
CCCCGCTAACCGTGCACGACTCCAAACTTAGCATTGCCACCC
AAGGACCCCTCACAGTGTCAGAAGGAAAGCTAGCCCTG
CAAACATCAGGCCCCCTCACCACCACCGATAGCAGTACCCTT
ACTATCACTGCCTCACCCCTCTAACTACTGCCACTGG
TAGCTTGGGCATTGACTTGAAAGAGCCCATTTATACACAAAA
TGGAAAACTAGGACTAAAGTACGGGGCTCCTTTGCATG
TAACAGACGACCTAAACACTTTGACCGTAGCAACTGGTCCAG
GTGTGACTATTAATAATACTTCCTTGCAAACTAAAGTT
ACTGGAGCCTTGGGTTTTGATTCACAAGGCAATATGCAACTT
AATGTAGCAGGAGGACTAAGGATTGATTCTCAAAACAG
ACGCCTTATACTTGATGTTAGTTATCCGTTTGATGCTCAAAAC
CAACTAAATCTAAGACTAGGACAGGGCCCTCTTTTTA
TAAACTCAGCCCACAACTTGGATATTAACTACAACAAAGGCC
TTTACTTGTTTACAGCTTCAAACAATTCCAAAAAGCTT
GAGGTTAACCTAAGCACTGCCAAGGGGTTGATGTTTGACGC
TACAGCCATAGCCATTAATGCAGGAGATGGGCTTGAATT
TGGTTCACCTAATGCACCAAACACAAATCCCCTCAAAACAAA
AATTGGCCATGGCCTAGAATTTGATTCAAACAAGGCTA
TGGTTCCTAAACTAGGAACTGGCCTTAGTTTTGACAGCACAG
GTGCCATTACAGTAGGAAACAAAAATAATGATAAGCTA
ACTTGTGGACCACACCAGCTCCATCTCCTAACTGTAGACTA
AATGCAGAGAAGATGCTAAACTCACTTTGGTCTTAAC
AAAATGTGGCAGTCAAATACTTGCTACAGTTTCAGTTTTGGC
TGTTAAAGGCAGTTTGGCTCCAATATCTGGAACAGTTC
AAAGTGCTCATCTTATTAAGATTTGACGAAAATGGAGTGC
TACTAAACAATTCCTTCCTGGACCCAGAATCTTGGAAC
TTTAGAAATGGAGATCTTACTGAAGGCACAGCCTATACAAAC
GCTGTTGGATTTATGCCTAACCTATCAGCTTATCCAAA
ATCTCACGGTAAAACTGCCAAAAGTAACATTGTCAGTCAAGT
TTACTTAAACGGAGACAAAACTAAACCTGTAACACTAA
```

FIG.10R

```
CCATTACACTAAACGGTACACAGGAAACAGGAGACACAACT
CCAAGTGCATACTCTATGTCATTTTCATGGGACTGGTCT
GGCCACAACTACATTAATGAAATATTTGCCACATCCTCTTACA
CTTTTTCATACATTGCCCAAGAATAAAGAATCGTTTG
TGTTATGTTTCAACGTGTTTATTTTTCAATTGCAGAAAATTTCA
AGTCATTTTTCATTCAGTAGTATAGCCCCACCACCA
CATAGCTTATACAGATCACCGTACCTTAATCAAACTCACAGA
ACCCTAGTATTCAACCTGCCACCTCCCTCCCAACACAC
AGAGTACACAGTCCTTTCTCCCCGGCTGGCCTTAAAAAGCAT
CATATCATGGGTAACAGACATATTCTTAGGTGTTATAT
TCCACACGGTTTCCTGTCGAGCCAAACGCTCATCAGTGATAT
TAATAAACTCCCCGGGCAGCTCACTTAAGTTCATGTCG
CTGTCCAGCTGCTGAGCCACAGGCTGCTGTCCAACTTGCGG
TTGCTTAACGGGCGGCGAAGGAGAAGTCCACTCCTACAT
GGGGGTAGAGTCATAATCGTGCATCAGGATAGGGCGGTGGT
GCTGCAGCAGCGGCGAATAAACTGCTGCCGCCGCCGCT
CCGTCCTGCAGGAATACAACATGGCAGTGGTCTCCTCAGCG
ATGATTCGCACCGCCCGCAGCATAAGGCGCCTTGTCCTC
CGGGCACAGCAGCGCACCCTGATCTCACTTAAATCAGCACA
GTAACTGCAGCACAGCACCACAATATTGTTCAAAATCCC
ACAGTGCAAGGCGCTGTATCCAAAGCTCATGGCGGGGACCA
CAGAACCCACGTGGCCATCATACCACAAGCGCAGGTAGA
TTAAGTGGCGACCCTCATAAACACGCTGGACATAAACATTA
CCTCTTTTGGCATGTTGTAATTCACCACCTCCCGGTAC
CATATAAACCTCTGATTAAACATGGCGCCATCCACCACCATC
CTAAACCAGCTGGCCAAAACCTGCCCGCCGGCTATACA
CTGCAGGGAACCGGGACTGGAACAATGACAGTGGAGAGCC
CAGGACTCGTAACCATGGATCATCATGCTCGTCATGATAT
CAATGTTGGCACAACACAGGCACACGTGCATACACTTCCTCA
GGATTACAAGCTCCTCCCGCGTTAGAACCATATCCCAG
GGAACAACCCATTCCTGAATCAGCGTAAATCCCACACTGCAG
GGAAGACCTCGCACGTAACTCACGTTGTGCATTGTCAA
AGTGTTACATTCGGGCAGCAGCGGATGATCCTCCAGTATGG
TAGCGCGGGTTTCTGTCTCAAAAGGAGGTAGACGATCCC
TACTGTACGGAGTGCGCCGAGACAACCGAGATCGTGTTGGT
CGTAGTGTCATGCCAAATGGAACGCCGGACGTAGTCATA
TTTCCTGAAGCAAAACCAGGTGCGGGCGTGACAAACAGATC
TGCGTCTCCGGTCTCGCCGCTTAGATCGCTCTGTCTAGT
AGTTGTAGTATATCCACTCTCTCAAAGCATCCAGGCGCCCCCC
TGGCTTCGGGTTCTATGTAAACTCCTTCATGCGCCGCT
GCCCTGATAACATCCACCACCGCAGAATAAGCCACACCCAG
CCAACCTACACATTCGTTCTGCGAGTCACACACGGGAGG
AGCGGGAAGAGCTGGAAGAACCATGTTTTTTTTTTATTCCA
AAAGATTATCCAAAACCTCAAAATGAAGATCTATTAAG
TGAACGCGCTCCCCTCCGGTGGCGTGGTCAAACTCTACAGC
CAAAGAACAGATAATGGCATTTGTAAGATGTTGCACAAT
```

FIG.10S

```
GGCTTCCAAAAGGCAAACGGCCCTCACGTCCAAGTGGACGT
AAAGGCTAAACCCTTCAGGGTGAATCTCCTCTATAAACA
TTCCAGCACCTTCAACCATGCCCAAATAATTCTCATCTCGCCA
CCTTCTCAATATATCTCTAAGCAAATCCCGAATATTA
AGTCCGGCCATTGTAAAATCTGCTCCAGAGCGCCCTCCACC
TTCAGCCTCAAGCAGCGAATCATGATTGCAAAAATTCA
GGTTCCTCACAGACCTGTATAAGATTCAAAAGCGGAACATTA
ACAAAAATACCGCGATCCCGTAGGTCCCTTCGCAGGGC
CAGCTGAACATAATCGTGCAGGTCTGCACGGACCAGCGCGG
CCACTTCCCCGCCAGGAACCTTGACAAAAGAACCCACAC
TGATTATGACACGCATACTCGGAGCTATGCTAACCAGCGTAG
CCCCGATGTAAGCTTTGTTGCATGGGCGGCGATATAAA
ATGCAAGGTGCTGCTCAAAAAATCAGGCAAAGCCTCGCGCA
AAAAGAAAGCACATCGTAGTCATGCTCATGCAGATAAA
GGCAGGTAAGCTCCGGAACCACCACAGCCCCCGACACCATT
TTTCTCTCAAACATGTCTGCGGGTTTCTGCATAAACACA
AAATAAAATAACAAAAAACATTTAAACATTAGAAGCCTGTCT
TACAACAGGAAAAACAACCCTTATAAGCATAAGACGG
ACTACGGCCATGCCGGCGTGACCGTAAAAAAACTGGTCACC
GTGATTAAAAAGCACCACCGACAGCTCCTCGGTCATGTC
CGGAGTCATAATGTAAGACTCGGTAAACACATCAGGTTGATT
CATCGGTCAGTGCTAAAAAGCGACCGAAATAGCCCGGG
GGAATACATACCCGCAGGCGTAGAGACAACATTACAGCCCC
CATAGGAGGTATAACAAAATTAATAGGAGAGAAAAACAC
ATAAACACCTGAAAAACCCTCCTGCCTAGGCAAAATAGCACC
CTCCCGCTCCAGAACAACATACAGCGCTTCACAGCGGC
AGCCTAACAGTCAGCCTTACCAGTAAAAAGAAAACCTATTA
AAAAAACACCACTCGACACGGCACCAGCTCAATCAGTC
ACAGTGTAAAAAGGGCCAAGTGCAGAGCGAGTATATATAG
GACTAAAAAATGACGTAACGGTTAAAGTCCACAAAAAAC
ACCCAGAAACCGCACGCGAACCTACGCCCAGAAACGAAAG
CCAAAAACCCACAACTTCCTCAAATCGTCACTTCCGTT
TTCCCACGTTACGTAACTTCCATTTTAAGAAAACTACAATTC
CCAACACATACAAGTTACTCCGCCCTAAAACCTACGT
CACCCGCCCCGTTCCCACGCCCCGCGCCACGTCACAAACTC
CACCCCCTCATTATCATATTGGCTTCAATCCAAAATAAG
GTATAT
```

FIG.10T

Query = Human Hyde, Sbjct = Human Hyde-40 (II)

```
Query: 1    ggggagctgccgcggtcgctccgagaggcggccgcagagccaccaaatgccagaagag   60
            ||||||||||||||||||||||||||||||||||||||||||||||||||||||||||||
sbjct: 1    ggggagctgccgcggtcgctccgagaggcggccgcagagccaccaaatgccagaagag   60

Query: 61   atggacaagccactgatcagcctccacctggtggacagcgatagtagccttgccaaggtc  120
            ||||||||||||||||||||||||||||||||||||||||||||||||||||||||||||
Sbjct: 61   atggacaagccactgatcagcctccacctggtggacagcgatagtagccttgccaaggtc  120

Query: 121  cccgatgaggcccccaaagtgagcatcctgggtagcgggactttgcccgctccctggcc   180
            ||||||||||||||||||||||||||||||||||||||||||||||||||||||||||||
Sbjct: 121  cccgatgaggcccccaaagtgagcatcctgggtagcgggactttgcccgctccctggcc   180

Query: 181  acacgcctggtgggctctggcttcaaagtggttggggagccgcaaccccaaacgcaca    240
            ||||||||||||||||||||||||||||||||||||||||||||||||||||||||||||
Sbjct: 181  acacgcctggtgggctctggcttcaaagtggttggggagccgcaaccccaaacgcaca    240

Query: 241  gccaggctgtttccctcagcggcccaagtgactttccaagagaggagcagtgagctcccg  300
            ||||||||||||||||||||||||||||||||||||||||||||||||||||||||||||
Sbjct: 241  gccaggctgtttccctcagcggcccaagtgactttccaagagaggagcagtgagctcccg  300

Query: 301  gaggtcatctttgtgvtgttccgggagcactactcttcactgtgcagtctcagtgac    360
            ||||||||||||||||||||||||||||||||||||||||||||||||||||||||||||
Sbjct: 301  gaggtcatctttgtgvtgttccgggagcactactcttcactgtgcagtctcagtgac    360
```

FIG.11A

```
Query:  361  cagctggcgggcaagatcctggtggatgtgagcaacccctacagagcaagagcaccttcag  420
             ||||||||||||||||||||||||||||||||||||||||||||||||||||||||||||
Sbjct:  361  cagctggcgggcaagatcctggtggatgtgagcaacccctacagagcaagagcaccttcag  420

Query:  421  catcgtgagtccaatgctgagtacctggcctccctcttccccacttgcacagtggtcaag  480
             ||||||||||||||||||||||||||||||||||||||||||||||||||||||||||||
Sbjct:  421  catcgtgagtccaatgctgagtacctggcctccctcttcccccacttgcacagtggtcaag  480

Query:  481  gccttcaatgtcatctctgcctggaccctgcaggctgcccctgagccccagggatggtaacgggcag  540
             ||||||||||||||||||||||||||||||||||||||||||||||||||||||||||||
Sbjct:  481  gccttcaatgtcatctctgcctggaccctgcaggctgcccctgagccccagggatggtaacgggcag  540

Query:  541  gtgcccatctgcggtgaccagccagaagccaagcgtgctgtctctcggagatggcgctcgcc  600
             ||||||||||||||||||||||||||||||||||||||||||||||||||||||||||||
Sbjct:  541  gtgcccatctgcggtgaccagccagaagccaagcgtgctgtctctcggagatggcgctcgcc  600

Query:  601  atgggcttcatgcccgtggacatgggatccctgcgtcagctggaggtggaggccatg  660
             ||||||||||||||||||||||||||||||||||||||||||||||||||||||||||||
Sbjct:  601  atgggcttcatgcccgtggacatgggatccctgcgtcagctggaggtggaggccatg  660

Query:  661  cccctgcgcctcctcccggcctggaaggtgccacccctgctgccctgggctcttcgtc  720
             ||||||||||||||||||||||||||||||||||||||||||||||||||||||||||||
Sbjct:  661  cccctgcgcctcctcccggcctggaaggtgccacccctgctgccctgggctcttcgtc  720
```

FIG.11B

```
Query:  721  tgcttctatgcctacaacttcgtccggacgttctgcagccctatgtgcaggaaagccag  780
             ||||||||||||||||||||||||||||||||||||||||||||||||||||||||||||
Sbjct:  721  tgcttctatgcctacaacttcgtccggacgttctgcagccctatgtgcaggaaagccag  780

Query:  781  aacaagttcttcaagctgccgtgtccgtggtccgtgtcaacaccacactgccgtgcctac  840
             ||||||||||||||||||||||||||||||||||||||||||||||||||||||||||||
Sbjct:  781  aacaagttcttcaagctgccgtgtccgtggtccgtgtcaacaccacactgccgtgcctac  840

Query:  841  gtgctgctgtcactcgtgtacttgcccggcgtgccctgcagctgcggcgc  900
             ||||||||||||||||||||||||||||||||||||||||||||||||||
Sbjct:  841  gtgctgctgtcactcgtgtacttgcccggcgtgccctgcagctgcggcgc  900

Query:  901  ggcaccaagtaccagcgcttccccgactgctggaccactggctacagcaccgcaagcag  960
             ||||||||||||||||||||||||||||||||||||||||||||||||||||||||||||
Sbjct:  901  ggcaccaagtaccagcgcttccccgactgctggaccactggctacagcaccgcaagcag  960

Query:  961  atcgggctgctcagctttcttctgcgccccctcacgcctctacagcttctgcttgccg  1020
             ||||||||||||||||||||||||||||||||||||||||||||||||||||||||||
Sbjct:  961  atcgggctgctcagctttcttctgcgccccctcacgcctctacagcttctgcttgccg  1020

Query:  1021 ctgcgccgcgccacgcgctacgacctggtcaacctggtcagtcaagcaggtcttggccaac  1080
             ||||||||||||||||||||||||||||||||||||||||||||||||||||||||||||||
Sbjct:  1021 ctgcgccgcgccacgcgctacgacctggtcaacctggtcagtcaagcaggtcttggccaac  1080
```

FIG.11C

```
Query: 1081 aagagccacctctgggtgaggaggtctggcgatggagatctacctctccctgggagtg 1140
             ||||||||||||||||||||||||||||||||||||||||||||||||||||||||||
Sbjct: 1081 aagagccacctctgggtgaggaggtctggcgatggagatctacctctccctgggagtg 1140

Query: 1141 ctggccctcggcacgttgtccctgctgccgtgacctcactgccgtccattgacaactgc 1200
             |||||||||||||||||||||||||||||||||||||||||||||||||||||||||
Sbjct: 1141 ctggccctcggcacgttgtccctgctgccgtgacctcactgccgtccattgacaactgc 1200

Query: 1201 ctcaactggagggagttcagcttcgttcagt 1231
             |||||||||||||||||||||||||||||||
Sbjct: 1201 ctcaactggagggagttcagcttcgttcagt 1231

Query: 1229 agtcctcactggcttttgtggccctcgtgctgagcacactgcacctacggct 1298
             |||||||||||||||||||||||||||||||||||||||||||||||||||
Sbjct: 1461 agtcctcactggcttttgtggccctcgtgctgagcacactgcacctacggct 1520

Query: 1289 ggacccggccttcgaggagagccgctacaagttctacctgcctccacttcacgctca 1348
             ||||||||||||||||||||||||||||||||||||||||||||||||||||||||
Sbjct: 1521 ggacccggccttcgaggagagccgctacaagttctacctgcctccacttcacgctca 1580

Query: 1349 cgctgctggtgccctgcgtcgtcatcctgccaaagccctgtttctcctgccctgcatca 1408
             ||||||||||||||||||||||||||||||||||||||||||||||||||||||||||
Sbjct: 1581 cgctgctggtgccctgcgtcgtcatcctgccaaagccctgtttctcctgccctgcatca 1640
```

FIG.11D

```
Query:  1409  gccgcagactcgccaggatccggagaggctgggagaggagagcaccatcaagttcacgc  1468
              ||||||||||||||||||||||||||||||||||||||||||||||||||||||||||||
Sbjct:  1641  gccgcagactcgccaggatccggagaggctgggagaggagagcaccatcaagttcacgc  1700

Query:  1469  tgcccacagaccacgcccctggccgagaagacgagccacgtatgatgtgcctgccctgggc  1528
              ||||||||||||||||||||||||||||||||||||||||||||||||||||||||||||
Sbjct:  1701  tgcccacagaccacgcccctggccgagaagacgagccacgtatgatgtgcctgccctgggc  1760

Query:  1529  tctggaccccgggcacacgagggggacgtgccctgagcccgttaggttttcttttcttggt  1588
              ||||||||||||||||||||||||||||||||||||||||||||||||||||||||||||
Sbjct:  1761  tctggaccccgggcacacgagggggacgtgccctgagcccgttaggttttcttttcttggt  1820

Query:  1589  ggtgcaaagtggtataactgtgtgcaaataggaggtttgaggtccaaattcctggactc  1648
              ||||||||||||||||||||||||||||||||||||||||||||||||||||||||||||
Sbjct:  1821  ggtgcaaagtggtataactgtgtgcaaataggaggtttgaggtccaaattcctgggactc  1880

Query:  1649  aaatgtatgcagtactattcagaatg  1674
              ||||||||||||||||||||||||||
Sbjct:  1881  aaatgtatgcagtactattcagaatg  1906
```

FIG.11E

```
Query: 1723  acaggatttgcaattatacatagctagctaaaaagttgggtctctgagatttcaacttgt 1782
             ||||||||||||||||||||||||||||||||||||||||||||||||||||||||||||
Sbjct: 1955  acaggatttgcaattatacatagctagctaaaaagttgggtctctgagatttcaacttgt 2014

Query: 1783  agatttaaaaacaagtgccgtacgttaagagaagagcagatcatgctattgtgacatttg 1842
             ||||||||||||||||||||||||||||||||||||||||||||||||||||||||||||
Sbjct: 2015  agatttaaaaacaagtgccgtacgttaagagaagagcagatcatgctattgtgacatttg 2074

Query: 1843  cagagatatacacacactttttgtacag 1870
             ||||||||||||||||||||||||||||
Sbjct: 2075  cagagatatacacacactttttgtacag 2102
```

FIG. 11F

Query = Human Hyde, Sbjct= Human Hyde-40 (Hyde II)

```
Query:   1  MPEEMDKPLISLHLVDSDSSLAKVPDEAPKVSILGSGDFARSLATRLVGSGFKVVVGSRN
Sbjct:   1  MPEEMDKPLISLHLVDSDSSLAKVPDEAPKVSILGSGDFARSLATRLVGSGFKVVVGSRN Query:  61  PKRTARLFPSSAQVTFQEEAVSSPEVIFVAVFREHYSSLCSLSDQLAGKILVDVSNPTEQ
Sbjct:  61  PKRTARLFPSSAQVTFQEEAVSSPEVIFVAVFREHYSSLCSLSDQLAGKILVDVSNPTEQ Query: 121  EHLQHRESNAEYLASLFPTCTVVKAFNVISAWTLQAGPRDGNGQVPICGDQPEAKRAVSE
Sbjct: 121  EHLQHRESNAEYLASLFPTCTVVKAFNVISAWTLQAGPRDGNGQVPICGDQPEAKRAVSE Query: 181  MALAMGFMPVDMGSLASAWEVFAMPLRLLPAWKVPTLLALGLFVCFYAYNFVRDVLQPYV
Sbjct: 181  MALAMGFMPVDMGSLASAWEVFAMPLRLLPAWKVPTLLALGLFVCFYAYNFVRDVLQPYV Query: 241  QESQNKFFKLPVSVVNTTLPCVAYVLLSLVYLPGVLAAALQLRRGTKYQRFPDWLDHWLQ
Sbjct: 241  QESQNKFFKLPVSVVNTTLPCVAYVLLSLVYLPGVLAAALQLRRGTKYQRFPDWLDHWLQ
```

FIG.12A

```
Query: 301 HRKQIGLLSFFCAALHALYSFCLPLRRAHRYDLVNLAVKQVLANKSHLWVEEVWRMEIYX
Sbjct: 301 HRKQIGLLSFFCAALHALYSFCLPLRRAHRYDLVNLAVKQVLANKSHLWVEEVWRMEIY
              HRKQIGLLSFFCAALHALYSFCLPLRRAHRYDLVNLAVKQVLANKSHLWVEEVWRMEIYX Query: 361 XXXXXXXXXXXXXXXXXXXXPSIANSLNWREFSFVQ 394
                               PSIANSLNWREFSFVQ
Sbjct: 361 SLGVLALGTLSLLAVTSLPSIANSLNWREFSFVQ 394
```

FIG.12B

Query = Human, Sbjct = rat

```
Query:  58 gagatggacaagccactgatcagcctccacctggtggacagcgatagccttgccaag 117
           |||||||||||| ||||| ||||| ||| ||||||||||||| ||||||  ||| |||
sbjct:  41 gagatggacaaaccgctcatcagtcgcgcttggtggacagtgatggcagtctggctgag 100

Query: 118 gtccccgatgaggcccccaaagtgagcatcctgggtagcggggactttgcccgctccctg 177
           ||||| || |  |||||||||||| ||||||||| |||| |||||| |||||| ||||||
Sbjct: 101 gtcccaaggagctcccaaagtgagcatcctgggcagcagcggattttgcccgtccctg 160

Query: 178 gccacacgcctggtgggcttcaaagtggttggggagccgcaaccccaaacgc 237
           |||||||||||||||||||| ||||||||||| |||| ||||| ||||||||||
Sbjct: 161 gccacacgcctggtgggcttctgtttgtggttgggtgggaagccgtaaccccaaacgc 220

Query: 238 acagccaggctgtttccctcagcgcccaagtgactttccaagaggagcagtgagctcc 297
           |||||  ||||||||||| ||   | ||||||||||||||||||||| ||||  ||||
Sbjct: 221 actgccggcctctcctccctcttagcccaagtgactttccaggaggagccgtgagctct 280

Query: 298 ccggaggtcatctttgtggctgtgttccgggagcactacttcttcactgtgcagtctcagt 357
           || |||||||||||||||||  |||||| |||||||||||||||||||||||||| || |
Sbjct: 281 ccagaggtcatctttgtggccgtgttccgggagcactacttcctcactgtgcagtcttgct 300

Query: 358 gaccagctggcgggcaagatcctggtggatgtgagcaaccctacagagcaagagcaccttt 417
           ||||| |||| ||||||||||||||||||  ||||||||||| || ||||||| |||||
Sbjct: 341 gaccagtggctggctgcaagatcctagtgatgtgagcaaccccacggagaaggagcgtctt 400
```

FIG.13A/1

```
Query: 418  cagcatcgtgagtccaatgctgagtacctggcctccctcttcccacttgcacagtggtc  477
            ||||  || ||  || ||| ||||||||||||| ||||||||  |||||||| ||||
Sbjct: 401  cagcaccgccagtcgaacgccagtacctggcctccctcttccctgcactgtggtc  460

Query: 478  aaggccttcaatgtcatctctgcctggacccctgcaggctggcccaagggatggtaacggg  537
            |||||||||||||| ||| |||||||  |||||||||||  |||||||||||| |||||
Sbjct: 461  aaggccttcaacgtcatctctgcctggacccctgcaggctggcccaagggatgggaacagg  520

Query: 538  caggtgcccatctgcggtgaccagcagaagccaagcgtgctgtctcggagatggcgctc  597
            |||||||| ||||| || |||||||| ||||||||||| || ||||||||||| ||||
Sbjct: 521  caggtgctctcatctgcggtgaccagcagaagccaagcacacacgttcagagatggcgcgc  580

Query: 598  gccatgggcttcatgcccgtggacatgggatccctgccgtcagcctgggaggtggaggcc  657
            |||||||||||  ||||| ||  | |||||||||||||||| ||||||||| ||||||
Sbjct: 581  gccatgggctttcaccccactggacatgggatccctgcgaggaggtagaggcc  640

Query: 658  atgccctgcgctcctcccggctggaaggtgccacccctgctgccctggggctcttc  717
            ||||||||| || |||| ||||||||||||||| |||||||||||||||  ||||
Sbjct: 641  ataccctgcgcctcctccttccatcctgaaggtgccacacctcctggccctgggctaagc  700

Query: 718  gtctgcttctatgcctacaacttcgtccggacgttctgcagccctatgtgcaggaaagc  777
            |||||||||||||||||||| ||||| |||| |||||||| |||  ||||| |||
Sbjct: 701  acacaaagctatgcctacaacttcatccggacgttctacagccgtacatccggaaagat  760
```

FIG.13A/2

```
Query:  778   cagaacaagttcttcaagctgcccgtgtccgtggtcaacaccacactgccgtgctgtggcc   837
              ||||||||||||||||||| ||||| ||||| |||||||||||| |||||| |||||| |
sbjct:  761   gagaacaagttctacaagatgcccctgtctgttcaacaccacgatacccctgtgtggct   820

Query:  838   tacgtgctgctgtcactcgtgtacttgcccggctgcggctgccctgcagctgcgg        897
              ||||||||||||| ||| |||| ||||| ||||| ||||| |||||| |||||||||
Sbjct:  821   tacgtgctgctgtccctgtttacctgcctggtgctgtgcagctgcctcagctgagg      880

Query:  898   cgcggcaccaagtaccagcgcttccccgactggctgaccactgctacagagccaag      957
              |||| ||||||||||||||||||||||||||||||||||||||||| | |||||||
Sbjct:  881   aggggaccaagtaccagcgcttcccagactggctgaccattggctgcagcaccgcaag   940

Query:  958   cagatcgggctgctcagcttctttctgcgcccctgcacgccctctacagcttctgcttg  1017
              |||||||||||||||||||| ||| ||||||  ||||||||||||||||||||||  |
Sbjct:  941   cagatcgggctactcagcttcagtttttcgccatgctgcacgctctctacagcttctgcctg   1000

Query:  1018  ccgctgcgccgcgccaccggcccgctacgacctggtcaacctggcagtcaagcaggtcttggcc  1077
              ||||||||||||| |||||||||||||| |||||||| |||||||| ||||||| |||||||
Sbjct:  1001  ccgctgcgccgctatgcgctcccaccgctgctggtcaacctggctgtgaagcaggtcctggcc   1060

Query:  1078  aacaagagccacctctgggt---ggaggaggtctggcggatggagatctacctctccctg  1134
              ||||||||||| ||||||||   ||||||||| ||||| ||||||||||  ||||||||
Sbjct:  1061  aacaagagccgctctgggttgaggaagaagtctggcggatggagatatacctgtccctg   1120
```

FIG.13A/3

```
Query:  1135  ggagtgctggccctcggcacgttgtccctgctgccgtgacctcactgccgtccattgca  1194
              || ||||||| ||| ||| ||||| || ||| ||| ||| ||| | ||  ||||||||
sbjct:  1121  ggtgtgctgctctgggcatgctgctgtcactgctgcggttacctgatccttccattgca  1180

Query:  1195  aactcgctcaactggaggagttcagcttcgttcagtcctcactgggctttgtggccctc  1254
              |||| |||||||||||| |||||| |||| ||  | |  | || ||| || |||| |
sbjct:  1181  aactcactcaactggaaggagttcagtttgtgcagtccacgctcgggcttcgtggccctg  1240

Query:  1255  gtgctgagcacactgcacacgctcacctacggctgctggacccgcgcttcgaggagccgc  1314
              |||||||||||| ||||| | | ||| |  ||| ||| ||| || ||  ||||||| |
sbjct:  1241  atgctgagcacaatgcacacccctcacctacggctggacccgtgctttgaggaaaccac  1300

Query:  1315  tacaagttctacctgcctcccacccttcacgctcacgctgctggtgccctgctgtcatc  1374
              ||||||||||||||||| |||| ||||||  ||||||  ||||  |||||||| |||||
sbjct:  1301  tacaagttctacctgccaccacattcacgctcacgctcctgctcctgtgtcatcatc  1360

Query:  1375  ctggccaaagccctgtttctcctgcccatcagccgcagactcgccagatccggaga  1434
              |||||||| |||| ||||| | |||| ||||||||||||| |||||||||||| |
sbjct:  1361  ctggccaagggcctcttctcctcctgccctgccagactcaccaagatccggcagg  1420

Query:  1435  ggctggggagaggagagagcaccatcaagttcacgctgcccacagaccgccctggccgag  1494
              |||||||| |||||||| ||||||| ||||| ||||| ||| |||| |||| ||||||
sbjct:  1421  ggctgggagagggagagatggtgccgtcaagttcatgctgccgccgcacacagggggag  1480

Query:  1495  aagacgagccacgtatgagg  1514
              || || |||||||| ||||
sbjct:  1481  aaaacaagccacgtgtgagg  1500
```

FIG.13A/4

Query = Human, Sbjct= rat

```
Query:   1  MPEEMDKPLISLHLVDSDSSLAKVPDEAPKVSILGSGDFARSLATRLVGSGFKVVVGSRN
            M EMDKPLIS  LVDSD SLA+VP EAPKV ILGSGDFARSLATRLVGSGF VVVGSRN
Sbjct:   1  MSGEMDKPLISRRLVDSDGSLAEVPDEAPKVGILGSGDFARSLATRLVGSGFFVVVGSRN Query:  61  PKRTARLFPSAAQVTFQEEAVSSPEVIFVAVFREHYSSLCSLSDQLAGKILVDVSNPTEQ
            PKRTA LFPS AQVTFQEEAVSSPEVIFVAVFREHYSSLCSL+DQLAGKILVDVSNPTE+
Sbjct:  61  PKRTAGLFPSLAQVTFQEEAVSSPEVIFVAVFREHYSSLCSLADQLAGKILVDVSNPTEK Query: 121  EHLQHRESNAEYLASLFPTCTVVKAFNVISAWTLQAGPRDGNGQVPICGDQPEAKRAVSE
            E LQHR+SNAEYLASLFP  CTVVKAFNVISAW LQAGPRDGN QV ICGDQ EAK VSE
Sbjct: 121  ERLQHRQSNAEYLASLFPACTVVKAFNVISAWALQAGPRDGNRQVLICGDQLEAKHTVSE Query: 181  MALAMGFMPVDMGSLASAWEVEAMPLRLLPAWKVPTLLALGLFVCFYAYNFVRDVLQPYV
            MA AMGF P+DMGSLASA  EVEA+ PLRLLP+WKVPTLLALGL   YAYNF+RDVLQPY+
Sbjct: 181  MARAMGFTPLDMGSLASAREVEAIPLRLLPSWKVPTLLALGLSTQSYAYNFIRDVLQPYI Query: 241  QESQNKFEKLPVSVVNTTLPCVAYVLLSIVYLPGVLAAALQLRRGTKYQRFPDWLDHWLQ
            ++ +NKF+K +P+SVVNTT+PCVAYVLLS+VYLPGVLAAALQLRRGTKYQRFPDWLDHWLQ
Sbjct: 241  RKDENKFYKMPLSVVNTTIPCVAYVLLSIVYLPGVLAAALQLRRGTKYQRFPDWLDHWLQ
```

FIG.13B/1

```
Query:  301  HRKQIGLLSFFCAALHALYSFCLPLRRAHRYDLVNLAVKQVLANKSHLWV-EEVWRMEIY
             HRKQIGLLSFF  A LHALYSFCLPLRR+HRYDLVNLAVKQVLANKS LWV EEVWRMEIY
Sbjct:  301  HRKQIGLLSFFAMLHALYSFCLPLRRSHRYDLVNLAVKQVLANKSRLWEEEVWRMEIY Query:  360  XXXXXXXXXXXXXXXXXXXXXPSIANSLNWREFSFVQSSLGFVALVLSTLHTLTYGWTRAFE
                                  PSIANSLNW+EFSFVQS+LGFVAL+LST+HTLTYGWTRAFE
Sbjct:  361  LSLGVLALGMLSLLAVTSIPSIANSLNWKEFSFVQSTLGFVAIMLSTMHTLTYGWTRAFE Query:  420  ESRYKFYXXXXXXXXXXXXXXXXXILAKALFLLPCISRRLARIRRGWERESTIKFTLPTDHA
             E+ YKFY                 ILAK LFLLPC+S RL +IRRGWER+  +KF LP  H
Sbjct:  421  ENHYKFYLPPTFTLTLLLPCVIILAKGLFLLPCLSHRLTKIRRGWERDGAVKFEMLPAGHT Query:  480  LAEKTSHV  487
                EKTSHV
Sbjct:  481  QGEKTSHV  488
```

FIG.13B/2

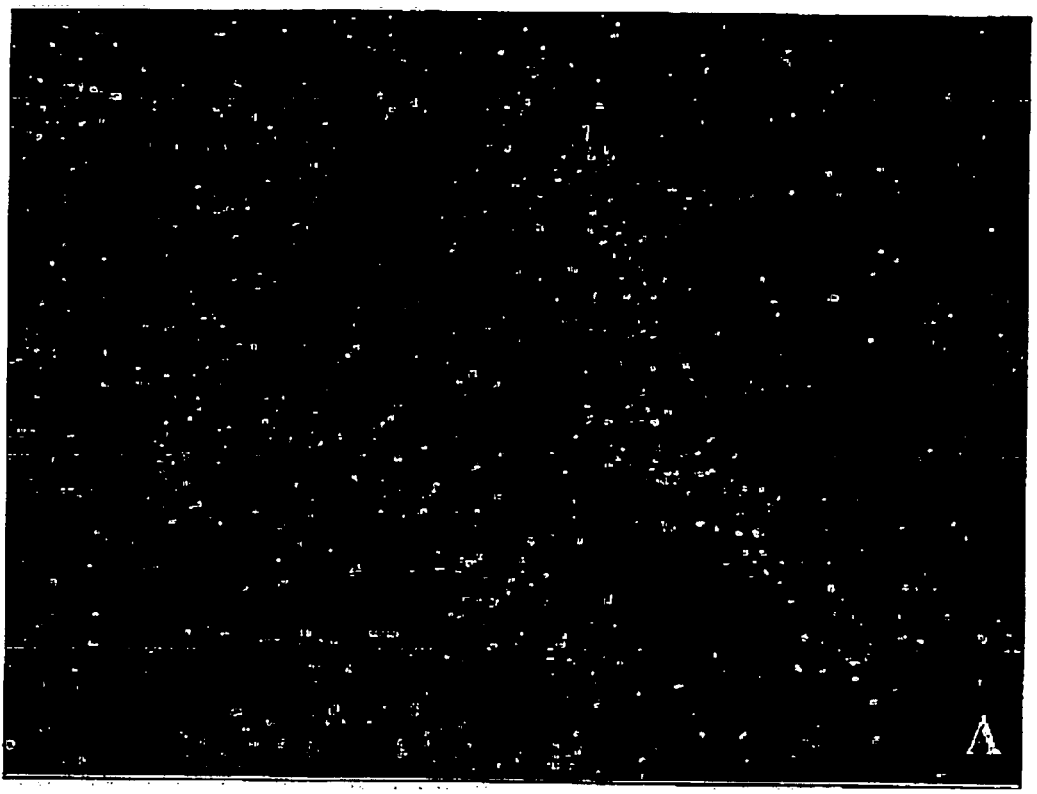
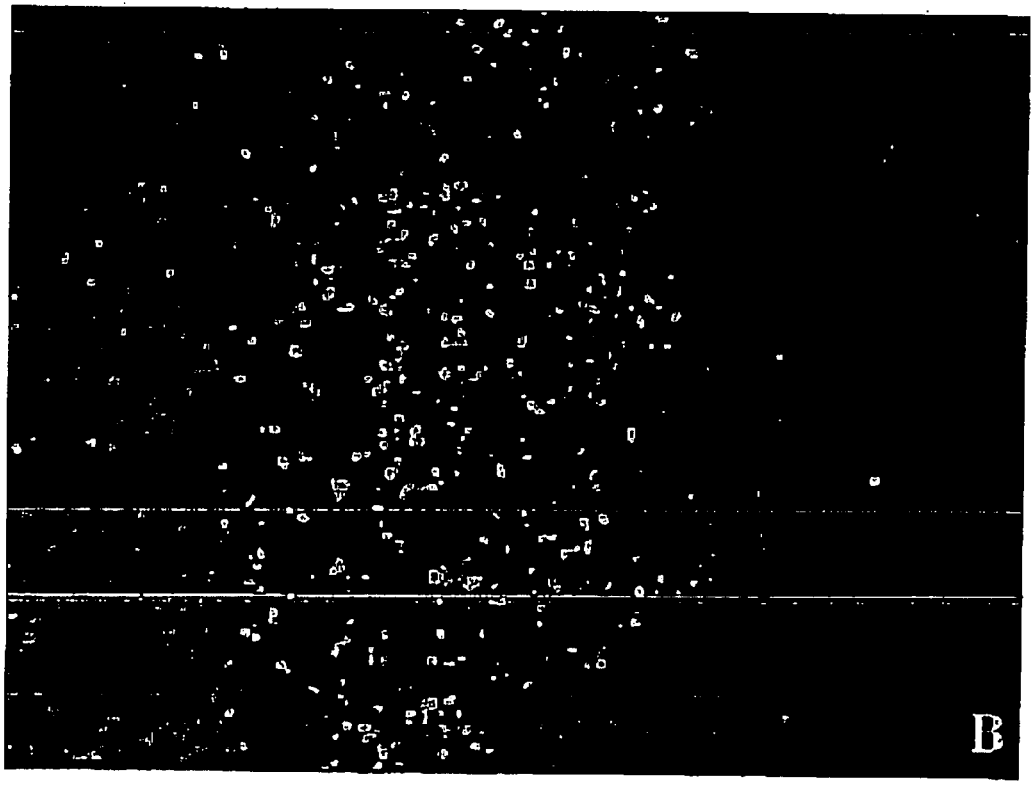
FIG.15

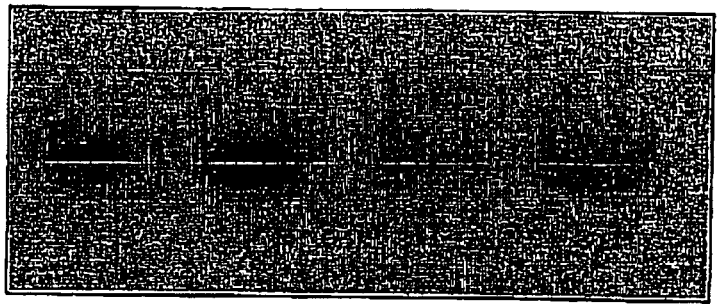
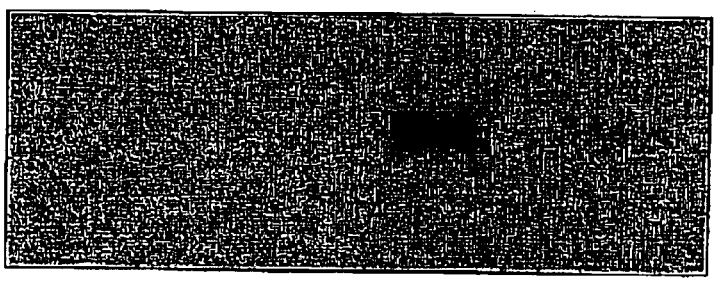
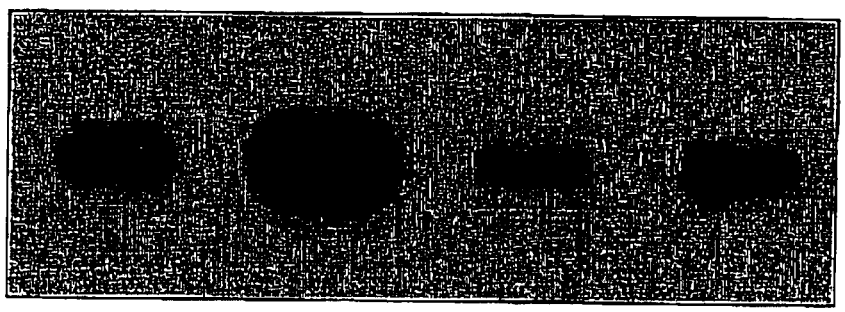
FIG.17

HUMAN P-HYDE PROTEINS

This application claims the benefit, and is a continuation in part of U.S. non-Provisional application Ser. No. 09/302,457 filed on Apr. 29, 1999, now abandoned and U.S. non-Provisional application Ser. No. 09/449,817 filed on Nov. 26, 1999, now pending.

FIELD OF INVENTION

This invention provides isolated nucleic acids of p-Hyde genes, proteins, analogs, fragments, mimetics, mutants, synthetics, and variants thereof of the p-Hyde family. This invention is directed to a method of inducing susceptibility to apoptosis with p-Hyde, a method of suppressing tumor growth with p-Hyde, and a method of treating a subject with cancer with p-Hyde alone or in combination with radiation, chemotherapy, or UV mimetic drugs.

BACKGROUND OF THE INVENTION

Prostate cancer is the most common malignancy in men with over 317,000 new cases and the second leading cause of male caner deaths in the United States (Boring et al., 1993; Steiner et. al, 1995). The molecular mechanisms responsible for the development, progression, and metastasis of prostate cancer remain largely unknown. Up to 20% of prostate cancers occur in men under the age of 65 years of age (Silverberg, 1986) suggesting that prostate carcinogenesis is not only associated with aging, but also to hereditary factors (Silverberg, 1987; McLellan and Norman, 1995; Carter et al., 1992). Genetic linkage studies of 691 affected families have revealed that an earlier age of onset of the disease in the proband and the presence of multiple affected family members are important determinants that increase the risk of prostate cancer. The pattern of inheritance of the putative prostate cancer gene appears to be autosomal dominant with an 88% penetrance rate (Steinberg, 1990). Thus, hereditary factors play an important role in prostate oncogenesis.

Like many carcinomas, prostate cancer formation is a multistep process involving tumor initiation, promotion, conversion, and progression (Carter et al., 1990; Sandberg, 1992). This process is driven by chromosomal instability, spontaneous mutations, and carcinogen induced genetic and epigenetic changes. Chromosomal instability leads to the total or partial gain or loss of chromosomes, translocations, and other abnormalities. Spontaneous mechanisms are age-related and include activation of oncogenes or inactivation of tumor suppressor genes by genetic mutations. These mutations result in the misincorporation of nucleotides during DNA replication of the coding region, alteration of the intron-exon junction sequences affecting the splicing mechanism, and aberrations of regulatory sequences changing the control of critical genes. These mutations escape genetic surveillance by a battery of DNA repair mechanisms and its associated gene products, such as p53 (Effert et al., 1992, Isaacs et al, 1991; Mellon et al., 1992) and p21 (El-Deiry et al., 1994) and PCNA (Templeton et al., 1996). Carcinogen-induced genetic ad epigenetic changes initiate tumors as a consequence of the direct damaging effects of carcinogenic agents of the DNA altering gene expression. Tumor initiation is subsequently followed by tumor promotion as affected cells have selective reproductive and clonal expansion capabilities through altered signaling transduction and proliferation responses to growth factors, resistance to cytotoxicity, and deregulation of terminal differentiation (Yuspa and Poirier, 1988; Weinstein, 1987). Finally, tumor promotion is succeeded by other genetic mutational events that lead to loss of hormone sensitivity, increased cell motility, invasion, alterations in programmed cell death and metastasis. Accordingly, the initiation and progression of cancer is a multistep process whereby genetic alterations or mutations of critical genes ultimately dictate defined cell phenotypes which differ in regard to many important cellular activities including cell proliferation, differentiation, and programmed cell death. The exact mutational events responsible for the multistep progression of prostate cancer, however, is unknown. A better understanding of the molecular mechanisms responsible for prostate cancer may lead to new therapies to combat, and perhaps, to even prevent prostate cancer.

SUMMARY OF THE INVENTION

The present invention provides isolated nucleic acids encoding P-Hyde genes of the p-Hyde family. The p-Hyde gene as shown herein is associated with: (1) the regression of tumor growth in vivo (2) the induction to susceptibility to apoptosis caused by UV or chemotherapy induced DNA damage, and (3) prevention of DNA repair with the upregulation of apoptosis as the result of UV damage and the failure to repair DNA.

This invention provides a novel class of genes which act as inhibitor of a DNA repair enzyme and induce susceptibility of cancer cells to cell death. Also, this invention provides isolated nucleic acids which encodes a mammalian p-Hyde protein which induce susceptibility of a cancer cell to cell death, including allelic, analogs, fragments, mimetics, mutants, synthetics, or variants thereof. This invention provides an isolated nucleic acids which encodes a human p-Hyde protein which induces susceptibility of a cancer cell to cell death, including allelic, analogs, fragments, mimetics, mutants, synthetics, or variants thereof Within this invention is provided a nucleic acid which has the nucleotide sequence as shown SEQ ID NO: 1, SEQ ID NO: 3, SEQ ID NO:5, SEQ ID NO:7 or SEQ ID NO:9.

Also, within the invention is a nucleic acid molecule which encodes a fragment of a polypeptide having the amino acid sequence of SEQ ID NO: 2, SEQ ID NO 4, SEQ ID NO 6, SEQ ID NO 8 or SEQ ID NO: 10, the fragment including at least 15 (25, 30, 50, 60, or 63) contiguous amino acids of SEQ ID NO: 2, SEQ ID NO 4, SEQ ID NO 6, SEQ ID NO 8 or SEQ ID NO 10.

Also, wit the invention is a nucleic acid molecule having the nucleotide sequence which is at least about 82%, 84%, 85%, 87%, 90%, 92%, 95%, or 98% identical to the nucleic acid sequence as shown in SEQ ID NO: 1, SEQ ID NO: 3, SEQ ID NO:5, SEQ ID NO:7 or SEQ ID NO: 9.

Also, within this invention is a nucleic acid molecule which encodes a naturally occurring allelic variant of a polypeptide comprising the amino acid sequence of SEQ ID NO: 2, SEQ ID NO 4, SEQ ID NO 6, SEQ ID NO 8, or SEQ ID NO 10 wherein the nucleic acid molecule hybridizes to a nucleic acid molecule comprising SEQ ID NO: 2, SEQ ID NO 4, SEQ ID NO6, SEQ ID NO 8 or SEQ ID NO 10 or the complement thereof under stringent conditions.

Also within the invention are isolated p-Hyde proteins having an amino acid sequence that is at least about 82%, 84%, 85%, 87%, 90%, 95%, or 98% identical to the amino acid sequence of SEQ ID NO: 1, SEQ ID NO: 3, SEQ ID NO:5, SEQ ID NO:7 or SEQ ID NO 9.

Also within the invention are: an isolated p-Hyde protein protein which is encoded by a nucleic acid molecule having a nucleotide sequence that is at east about 65%, preferably 75%, 80%, 85%, or 95% identical to SEQ ID NO: 1, SEQ ID NO: 3, SEQ ID NO:5, SEQ ID NO:7 or SEQ ID NO 9; and an isolated p-Hyde protein protein which is encoded by a nucleic acid molecule having a nucleotide sequence which hybridizes under stringent hybridization conditions to a nucleic acid molecule having the nucleotide sequence of SEQ ID NO: 1, SEQ ID NO: 3, SEQ ID NO:5, SEQ ID NO:7 or SEQ ID NO 9, or the complement thereof.

The p-Hyde protein of the present invention, or biologically active portions thereof, can be operably linked to a non-p-Hyde polypeptide (e.g., heterologous amino acid sequences) to form p-Hyde fusion proteins.

This invention provides a vector comprising the isolated nucleic acid encoding P-Hyde gene. This invention provides a replication-defective recombinant E1/E3 deleted adenovirus containing a truncated RSV promoter and the P-Hyde cDNA gene (AdRSVpHyde).

This invention provides an oligonucleotide of at least 15 nucleotides capable of specifically hybridizing with a sequence of nucleotides present within a nucleic acid which encodes the p-Hyde, or a sequence which is complementary to the nucleic acid which encodes the p-Hyde. This invention provides au antisense molecule, triplex oligonucleotide, or ribozyme which is capable of specifically hybridizing with the isolated nucleic acid encoding p-Hyde.

This invention provides a method for producing a polypeptide which comprises growing the host vector system under suitable conditions permitting production of the polypeptide and recovering the polypeptide so produced. In one embodiment the method of obtaining a polypeptide in purified form comprises: (a) introducing the vector into a suitable host cell; (b) culturing the resulting cell so as to produce the polypeptide; (c) recovering the polypeptide produced in step (b); and (d) purifying the polypeptide so recovered.

This invention provides a polypeptide comprising the amino acid sequence of a p-Hyde. This invention provides a fusion protein or chimeric comprising the polypeptide. This invention provides an antibody which specifically binds to the polypeptide. This invention provides a pharmaceutical composition comprising an amount of the polypeptide and a pharmaceutically effective carrier or diluent.

This invention provides a method for determining whether a subject carries a mutation in the p-Hyde gene which comprises: (a) obtaining an appropriate nucleic acid sample from the subject; and (b) determining whether the nucleic acid sample from step (a) is, or is derived from, a nucleic acid which encodes mutant p-Hyde so as to thereby determine whether a subject carries a mutation in the p-Hyde gene. In one embodiment is the nucleic acid sample in step (a) comprises mRNA corresponding to the transcript of DNA encoding a mutant p-Hyde, and wherein the determining of step (b) comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant p-Hyde.

This invention provides a method for screening a tumor sample from a human subject for a somatic alteration in a p-Hyde gene in said tumor which comprises gene comparing a first sequence selected form the group consisting of a p-Hyde gene from said tumor sample, p-Hyde RNA from said tumor sample and p-Hyde cDNA made from mRNA from said tumor sample with a second sequence selected from the group consisting of p-Hyde gene from a nontumor sample of said subject, p-Hyde RNA from said nontumor sample and p-Hyde cDNA made from mRNA from said nontumor sample, wherein a difference in the sequence of the p-Hyde gene, p-Hyde RNA or p-Hyde cDNA from said tumor sample from the sequence of the p-Hyde gene, p-Hyde RNA or p-Hyde cDNA from said nontumor sample indicates a somatic alteration in the p-Hyde gene in said tumor sample.

This invention provides a method for screening a tumor sample from a human subject for the presence of a somatic alteration in a p-Hyde gene in said tumor which comprises comparing p-Hyde polypeptide from said tumor sample from said subject to p-Hyde polypeptide from a nontumor sample from said subject to analyze for a difference between the polypeptides, wherein said comparing is performed by (i) detecting either a full length polypeptide or a truncated polypeptide in each sample or (ii) contacting an antibody which specifically binds to either an epitope of an altered p-Hyde polypeptide or an epitope of a wild-type p-Hyde polypeptide to the p-Hyde polypeptide from each sample and detecting antibody binding, wherein a difference between the p-Hyde polypeptide from said tumor sample from the p-Hyde polypeptide from said nontumor sample indicates the presence of a somatic alteration in the p-Hyde gene in said tumor sample.

This invention provides a method for identifying a chemical compound which is capable inducing susceptibility to cell death which comprises: (a) contacting the p-Hyde with a chemical compound under conditions permitting binding between the p-Hyde and the chemical compound; (b) detecting specific binding of the chemical compound to the p-Hyde; and (c) determining whether the chemical compound inhibits the p-Hyde so as to identify a chemical compound which is capable of capable inducing susceptibility to cell death.

This invention provides a method of inhibiting the growth of cancer cells, comprising the steps of obtaining the cells and contacting the cells of the subject with a replication-deficient adenovirus type 5 expression vector comprising an adenovirus genome having a deletion in the E1 and E3 region of the genome and an insertion within the region of a nucleic acid encoding p-Hyde under the control of a Rous Sarcoma virus promoter, thereby inhibiting the growth of the prostate cancer cells.

This invention provides a method of inhibiting the growth a prostate cancer cells, comprising: 1) obtaining a sample of prostate cells from a subject; 2) contacting the cells with a replication deficient adenovirus type 5 expression vector which comprises an adenovirus genome having a deletion in the E1 and E3 regions of the genome and an insertion within the regions of a p-Hyde cDNA under the control of a Rous Sarcoma virus promoter; and 3) introducing the cells into the subject, thereby inhibiting the growth of the cancer cells.

This invention provides a method of suppressing the growth of cancer cells in a subject, comprising introducing into the cancer cell an amount of a nucleic acid encoding a p-Hyde protein, a nucleic acid encoding a fragment of p-Hyde protein, or the nucleic acid encoding a mutant p-Hyde protein, thereby suppressing the growth of cancer cells in the subject.

This invention provides a method of suppressing growth of cancer cells in a subject, comprising administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby suppressing the growth of cancer cells in the subject.

This invention provides a method of inducing susceptibility to apoptosis of cancer cells in a subject, comprising introducing into the cancer cell an amount of a nucleic acid encoding a p-Hyde protein, a nucleic acid encoding a fragment of p-Hyde protein, or the nucleic acid encoding a mutant p-Hyde protein, thereby inducing susceptibility to apoptosis.

This invention provides a method of inducing susceptibility to apoptosis of cancer cells in a subject, comprising administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent thereby inducing susceptibility to apoptosis.

This invention provides a method of treating a subject with cancer which comprises administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby treating the subject with cancer.

This invention provides a method of treating a subject with cancer, comprising: 1) administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein in combination with radiation, chemotherapy, or UV mimetic drugs; and 2) a pharmaceutical acceptable carrier or diluent, thereby treating the subject with cancer.

This invention a method of treating a subject with cancer, comprising administering to the subject a therapeutically effective amount of a pharmaceutical composition comprising 1) an adenovirus type 5 expression vector which comprises a adenovirus genome having a deletion in the E1 and E3 regions of the genome and an insertion within the regions of a full length sense p-Hyde cDNA under the control of a Rous Sarcoma virus promoter, and 2) a suitable carrier or diluent, thereby treating the subject with cancer. In one embodiment the cancer is selected from a group consisting of melanoma; lymphoma; leukemia; and prostate, colorectal, pancreatic, breast, brain, or gastric carcinoma.

Lastly, the present invention provides the means necessary for production of gene-based therapies directed at cancer cells. These therapeutic agents may take the form of polynucleotides comprising all or a portion of the p-Hyde locus placed in appropriate vectors or delivered to target cells in more direct ways such that the function of the p-Hyde protein is reconstituted. Therapeutic agents may also take the form of polypeptides based on either a portion of, or the entire protein sequence of p-Hyde. These may functionally replace the activity of p-Hyde in vivo.

BRIEF DESCRIPTION OF THE DRAWINGS

FIG. 10. Sequence of region A (SEQ ID NO: 10) and of region B (SEQ ID NO: 11) of AdRSVpHyde.

FIG. 11. Comparison of the nucleotide sequence of the p-Hyde family genes between human p-Hyde (I) (SEQ ID NO: 1) and human p-Hyde 40 (II) (SEQ ID NO: 3).

FIG. 12. Comparison of the amino acid sequence of the p-Hyde family genes between human p-Hyde (I) (SEQ ID NO: 2) and human p-Hyde 40 (II) (SEQ ID NO: 3).

FIGS. 13A and 13B) Comparison of the nucleotide sequence of the p-Hyde family genes, between rat p-Hyde (SEQ ID NO: 5) and human p-Hyde (SEQ ID NO: 1). B) Comparison of the amino acid sequence of the p-Hyde family genes between rat p-Hyde (SEQ ID NO: 6) and human p-Hyde.

FIGS. 15A and 15B. TUNEL, assay of DU145 cells in vivo. DU145 xenograft tumors (about 80 mm$^3$) growing on nude mice were either untreated (A) or injected with 5×10$^9$ pfu AdRSVpHyde (B). Tumors were harvested in 21 days. Tumor sections were fixed and proceeded for TUNEL assay. The sections were counter stained with propidium iodide (red) to show the nucleus of cells. The bright yellowish stained cells indicated the apoptotic cells. Tumor sections from control virus-treated DU145 tumor showed the similar results as in (A). Magnification: A, B: ×20.

FIG. 17. Expression of Rb and p53 in various prostate cancer cell lines. Various prostate cancer cells were screened for endogenous Rb and p53 expression at mRNA levels. Each well was loaded with 10 μg of total RNA. Samples were electrophoresed in 12.5% agarose gel, transferred to nylon membrane, and hybridized with $^{32}$P-labeled Rb (which showed an about 4.4 kb transcript) or p53 cDNA (which showed an about 2.5 kb transcript). The Northern blot was then stripped and rehybridized with GAPDH cDNA (which showed a 1.2 kb transcript) to assess RNA integrity and gel loading.

DETAILED DESCRIPTION OF THE INVENTION

Figure 1:
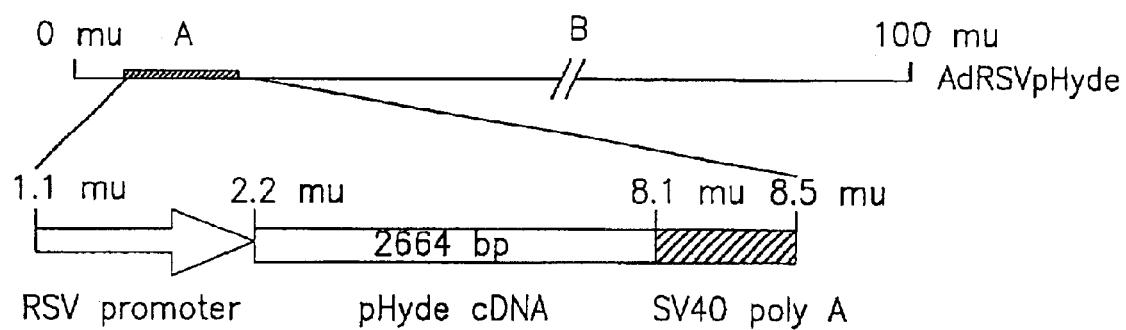
FIG. 1. Schematic presentation of AdRSVpHyde structure. The 2664 bp inserted fragment contains a 1467 bp full-length p-Hyde cDNA gene (SEQ ID NO: 1) and 1166 bp 3' untranslated downstream region. The complete sequence of AdRSVpHyde is set forth in FIG. 10, Specifically, the nucleic acid sequence of region A in FIG. 1 is set forth in FIG. 10 Region A and the nucleic acid sequence of region B in FIG. 2 is set forth in FIG. 10 at Region B.

This invention provides a novel class of genes which act as inhibitor of a DNA repair enzyme and induces suscepti-bility of cancer cells to cell death. Functionally, P-Hyde is and associated with suppression of tumor growth in vivo and increased susceptibility to apoptosis induced by UV irradiation or FUrD treatment. The upregulation of apoptosis due to UV damage is correlated with the presence of intact photoproduct in prostate cancer cell lines stably transfected with p-Hyde. Use of p-Hyde in human gene therapy as monotherapy or in combination with radiation or chemotherapy is useful against cancer or hyperproliferative human diseases. In one embodiment, the class of proteins, such as P-Hyde, are DNA repair enzyme inhibitors which downregulate Nucleotide-Excision-Repair (NER) pathway in prostate cancer, O$^6$-methylguanine-DNA methyl transferase (MGMT) DNA repair pathway in colon cancer cell lines, O$^6$-methylguanine-DNA methyl transferase enzyme (O$^6$MGMT) and 6,4, photoproducts (6,4PP). The class of genes is characterized by comprising a leucine zipper binding domain and a death domain which causes the cell to be apoptotic. Human p-Hyde (I) and human p-Hyde 40 (II) are examples set forth herein, of a family of molecules (the "p-Hyde family") having certain homologous sequences and conserved structural and functional features.

This invention provides an isolated nucleic acid which encodes a mammalian p-Hyde protein which induces susceptibility of a cancer cell to cell death, including allelic, analogs, fragments, mimetics, mutants, synthetics, or variants thereof. This invention provides an isolated nucleic acid which encodes a human p-Hyde protein which induces susceptibility of a cancer cell to cell death, including allelic, analogs, fragments, mimetics, mutants, synthetics, or variants thereof.

As used interchangeably herein a "p-Hyde activity", "biological activity of p-Hyde" or "functional activity of p-Hyde", refers to an activity exerted by a p-Hyde protein, polypeptide or nucleic acid molecule on a p-Hyde responsive cell as determined in vivo, or in vitro, according to standard techniques which causes apoptosis of the cell. P-Hyde refers to a family of genes having the p-Hyde activity. Examples of such genes are rat p-hyde, human p-Hyde (I), and human p-Hyde 40 (II). In one embodiment, these sequences comprise SEQ ID NO: 7 on the nucleotide level and SEQ ID NO: 8 on the amino acid level. Also, examples, of family p-Hyde gene members include isolated nucleic sequences of SEQ ID NOS. 1, 3, 5, or 7 on the nucleotide level and amino acid sequences of SEQ ID NOS: 2, 4, 6 or 8 on the amino acid level.

In one embodiment the p-Hyde gene has a nucleotide sequence having at least 85% similarity with the nucleic acid coding sequence, of SEQ ID NO: 1. In another embodiment the nucleic acid has a nucleotide sequence having at least 87% similarity with the nucleic acid coding sequence of SEQ ID NO: 1. In another embodiment the nucleic acid has a nucleotide sequence having at least 90% similarity with the nucleic acid coding sequence of SEQ ID NO: 1. In another embodiment the nucleic acid has a nucleotide sequence having at least 95% similarity with the nucleic acid coding sequence of SEQ ID NO: 1. In another embodiment the nucleic acid fragment comprises a fragment which begins at the nucleic acid at position 1 of the SEQ ID NO: 1 and ends at position 557 of SEQ ID NO: 1. In another embodiment the nucleic acid comprises a fragment which begins at the nucleic acid at position 1 of SEQ ID NO: 1 and ends at position 158 of SEQ ID NO: 1. In another embodiment the nucleic acid comprises a fragment which begins at the nucleic acid at position 50 of SEQ MD NO: 1 and ends at position 120 of SEQ ID NO: 1. The nucleic acid is DNA, cDNA, genomic DNA, or RNA, Human p-Hyde nucleic acid coding region:

1 ggggagctgc cgcggtcgct ccgagcggcg ggccgcagag ccaccaaaat
gccagaagag 61 atggacaagc cactgatcag cctccacctg gtggacagcg atagtagcct
tgccaaggtc 121 cccgatgagg cccccaaagt gagcatcctg ggtagcgggg actttgcccg
ctccctggcc 181 acacgcctgg tgggctctgg cttcaaagtg gtggtgggga gccgcaaccc
caaacgcaca 241 gccaggctgt ttccctcagc ggcccaagtg actttccaag aggaggcagt
gagctcccg 301 gaggtcatct ttgtggctgt gttccgggag cactactctt cactgtgcag
tctcagtgac 361 cagctggcgg gcaagatcct ggtggatgtg agcaaccccta cagagcaaga
gcaccttcag 421 catcgtgagt ccaatgctga gtacctggcc tccctcttcc ccacttgcac
agtggtcaag 481 gccttcaatg tcatctctgc ctggaccctg ctggctggcc caagggatgg
taacgggcag 541 gtgcccatct gcggtgacca gccagaagcc aagcgtgctg tctcggagat
ggcgctcgcc 601 atgggcttca tgcccgtgga catgggatcc ctggcgtcag cctgggaggt
ggaggccatg 661 cccctgcgcc tcctcccggc ctggaaggtg cccaccctgc tggccctggg
gctcttcgtc 721 tgcttctatg cctacaactt cgtccgggac gttctgcagc cctatgtgca
ggaaagccag 781 aacaagttct tcaagctgcc cgtgtccgtg gtcaacacca cactgccgtg
cgtggcctac 841 gtgctgctgt cactcgtgta cttgcccggc gtgctggcgg ctgccctgca
gctgcggcgc 901 ggcaccaagt accagcgctt ccccgactgg ctggaccact ggctacagca
ccgcaagcag 961 atcgggctgc tcagcttctt ctgcgccgcc ctgcacgccc tctacagctt
ctgcttgccg 1021 ctgcgccgcc cccaccgcta cgacctggtc aacctggcag tcaagcaggt
cttggccaac 1081 aagagccacc tctgggtgga ggaggtctgg cggatggaga tctacctctc
cctgggagtg 1141 ctggccctcg gcacgttgtc cctgctggcc gtgacctcac tgccgtccat
tgcaaactcg 1201 ctcaactgga gggagttcag cttcgttcag tcctcactgg gctttgtggc
cctcgtgctg 1261 agcacactgc acacgctcac ctacggctgg acccgcgcct tcgaggagag
ccgctacaag 1321 ttctacctgc ctcccacctt cacgctcacg ctgctggtgc cctgcgtcgt
catcctggcc 1381 aaagccctgt ttctcctgcc ctgcatcagc cgcagactcg ccaggatccg
gagaggctgg 1441 gagagggaga gcaccatcaa gttcacgctg cccacagacc acgccctggc
cgagaagacg 1501 agccacgtat gaggtgcctg ccctgggctc tggacccgg gcacacgagg
gacggtgccc 1561 tgagcccgtt aggttttctt ttcttggtgg tgcaaagtgg tataactgtg
tgcaaatagg 1621 aggtttgagg tccaaattcc tgggactcaa atgtatgcag tactattcag
aatgatatac 1681 acacatatgt gtatatgtat ttacatatat tccacatata taacaggatt
tgcaattata 1741 catagctagc taaaaagttg ggtctctgag atttcaactt gtagatttaa
aaacaagtgc 1801 cgtacgttaa gagaagagca gatcatgcta ttgtgacatt tgcagagata
tacacacact 1861 ttttgtacag aaaaaaaaaa aaaaaa (SEQ ID NO.: 1)

In another embodiment the nucleic acid encodes an amino acid sequence having the sequence as set forth in SEQ ID NO 2. In one embodiment the the amino acid fragment comprises a fragment which begins at the amino acid at position 1 of SEQ ID NO 2 and ends at position 101. In on embodiment the amino acid fragment comprises a fragment which begins at the amino acid at position 1 of SEQ ID No 2 and ends at position 80. In one embodiment the amino acid fragment comprises a fragment which begins at the amino acid at position 1 of SEQ ID NO 2 and ends at position 60. In one embodiment the amino acid has at least 85% similarity with the nucleic acid coding sequence of SEQ ID NO 2. In another embodiment the amino acid has at least 90% similarity with the nucleic acid coding sequence of SEQ ID NO 2. In another embodiment the amino acid has at leas 95% similarity with the nucleic acid coding sequence of SEQ ID NO 2.

Human p-Hyde amino acid sequence:

1 MPEEMDKPLI SLHLVDSDSS LAKVPDEAPK
VSILGSGDFA RSLATRLVGS GFKVVVGSRN

61 PKRTARLFPS AAQVTFQEEA VSSPEVIFVA
VFREHYSSLC SLSDQLAGKI LVDVSNPTEQ

121 EHLQHRESNA EYLASLFPTC TVVKAFNVIS
AWTLQAGPRD GNGQVPICGD QPEAKRAVSE

181 MALAMGFMPV DMGSLASAWE VEAMPLRLLP
AWKVPTLLAL GLFVCFYAYN PVRDVLQPYV

241 QESQNKFFKL PVSVVNTTLP CVAYVLLSLV
YLPGVLAAAL QLRRGTKYQR FPDWLDHMLQ

301 HRKQIGLLSF FCAALHALYS FCLPLRRAHR
YDLVNLAVKQ VLANKSHLWV EEVWRMEIYL

361 SLGVLALGTL SLLAVTSLPS IANSLNWREF
SFVQSSLGFV ALVLSTLHTL TYGWTRAFEE

421 SRYKFYLPPT FTLTLLVPCV VILAKALFLL
PCISRRLARI RRGWERESTI KTDLPTDHAL

481 AEKTSHV* (SEQ ID NO.: 2)

In one embodiment the p-Hyde gene has a nucleotide sequence having at least 75% similarity with the nucleic acid coding sequence of SEQ ID NO: 3. In another embodiment the nucleic acid has a nucleotide sequence having at least 85% similarity with the nucleic acid coding sequence of SEQ ID NO: 3. In another embodiment the nucleic acid has a nucleotide sequence having at least 90% similarity with the nucleic acid coding sequence of SEQ ID NO: 3. In another embodiment the nucleic acid has a nucleotide sequence having at least 95% similarity with the nucleic acid coding sequence of SEQ ID NO: 3. In another embodiment the nucleic acid fragment comprises a fragment which begins at the nucleic acid at position 1 of the SEQ ID NO: 3 and ends at position 557 of SEQ ID NO: 3. In another embodiment the nucleic acid comprises a fragment which begins at the nucleic acid at position 1 of SEQ ID NO: 3 and ends at position 158 of SEQ ID NO: 3. In another embodiment the nucleic acid comprises a fragment which begins at the nucleic acid at position 50 of SEQ ID NO: 3 and ends at position 120 of SEQ ID NO: 3. The nucleic acid is DNA, cDNA, genomic DNA, or RNA.

Human P-Hyde 40 nucleic acid sequence:

```
   1 ggggagctgc cgcggtcgt ccgagcggcg ggccgcagag ccaccaaaat
     gccagaagag 61 atggacaagc cactgatcag cctccacctg gtggacagcg atagtagcct
     tgccaaggtc 121 cccgatgagg cccccaaagt gagcatcctg ggtagcgggg actttgcccg
     ctccctggcc 181 acacgcctgg tgggctctgg cttcaaagtg gtggtgggga gccgcaaccc
     caaacgcaca 241 gccaggctgt ttccctcagc ggcccaagtg actttccaag aggaggcagt
     gagctcccg 301 gaggtcatct ttgtggctgt gttccgggag cactactctt cactgtgcag
     tctcagtgac 361 cagctggcgg gcaagatcct ggtggatgtg agcaaccctca cagagcaaga
     gcaccttcag 421 catcgtgagt ccaatgctga gtacctggcc tccctcttcc ccacttgcac
     agtggtcaag 481 gccttcaatg tcatctctgc ctggacccctg caggctggcc caagggatgg
     taacgggcag 541 gtgcccatct gcggtgacca gccagaagcc aagcgtgctg tctcggagat
     ggcgctcgcc 601 atgggcttca tgcccgtgga catgggatcc ctggcgtcag cctgggaggt
     ggaggccatg 661 ccctgcgcc tcctcccggc ctggaaggtg cccaccctgc tggccctggg
     gctcttcgtc 721 tgcttctatg cctacaactt cgtccgggac gttctgcagc cctatgtgca
     ggaaagccag 781 aacaagttct tcaagctgcc cgtgtccgtg gtcaacacca cactgccgtg
     cgtggcctac 841 gtgctgctgt cactcgtgta cttgcccggc gtgctggcgg ctgccctgca
     gctgcggcgc 901 ggcaccaagt accagcgctt ccccgactgg ctggaccact ggctacagca
     ccgcaagcag 961 atcgggctgc tcagcttctt ctgcgccgcc ctgcacgccc tctacagctt
     ctgcttgccg 1021 ctgcgccgcg cccaccgcta cgacctggtc aacctggcag tcaagcaggt
     cttggccaac 1081 aagagccacc tctgggtgga ggaggtctgg cggatggaga tctacctctc
     cctgggagtg 1141 ctggccctcg gcacgttgtc cctgctggcc gtgacctcac tgccgtccat
     tgcaaactcg 1201 ctcaactgga gggagttcag cttcgttcag tgtgtggcaa cttccagtgc
     aggaaacaca 1261 ggcagtggaa cccgaagacc tgaatctcag tcccaagacc cccacttacc
     tgcccccgcat 1321 catcagacaa gtttcctagg ccctcggagc ttctgctgct cacttgtgcc
     tgtgtccacc 1381 ccatatggtc atcaagagga tttgagctgg acacgttaaa tgcaggatgc
     gtgcagccaa 1441 cagtggcatg ctggcttttg agtcctcact gggctttgtg gccctcgtgc
     tgagcacact
```

```
1501 gcacacgctc acctacggct ggacccgcgc cttcgaggag agccgctaca
     agttctacct 1561 gcctcccacc ttcacgctca cgctgctggt gccctgcgtc gtcatcctgg
     ccaaagccct 1621 gtttctcctg ccctgcatca gccgcagact cgccaggatc cggagaggct
     gggagaggga 1681 gagcaccatc aagttcacgc tgcccacaga ccacgccctg gccgagaaga
     cgagccacgt 1741 atgaggtgcc tgccctgggc tctggacccc gggcacacga gggacggtgc
     cctgagcccg 1801 ttaggttttc ttttcttggt ggtgcaaagt ggtataactg tgtgcaaata
     ggaggtttga 1861 ggtccaaatt cctgggactc aaatgtatgc agtactattc agaatgatat
     acacacatat 1921 gtgtatatgt atttacatat attccacata tataacagga tttgcaatta
     tacatagcta 1981 gctaaaaagt tgggtctctg agatttcaac ttgtagattt aaaaacaagt
     gccgtacgtt 2041 aagagaagag cagatcatgc tattgtgaca tttgcagaga tatacacaca
     cttttttgtac 2101 agaaaaaaaa aaaaaaaa                                    (SEQ ID NO.: 3)
```

In another embodiment the nucleic acid encodes an amino acid sequence having the sequence as set forth in SEQ ID NO 4. In one embodiment the the amino acid fragment comprises a fragment which begins at the amino acid at position 1 of SEQ ID NO 4 and ends at position 101. In one embodiment the amino acid fragment comprises a fragment which begins at the amino acid at position 1 of SEQ ID NO 4 and ends at position 80. In one embodiment the amino acid fragment comprises a fragment which begins at the amino acid at position 1 of SEQ ID NO 4 and ends at position 60. In one embodiment the amino acid has at least 85% similarity with the nucleic acid coding sequence of SEQ ID NO 4. In another embodiment the amino acid has at least 90% similarity with the nucleic acid coding sequence of SEQ ID NO 4. In another embodiment the amino acid has at least 95% similarity with the nucleic acid coding sequence of SEQ ID NO 4.

Human p-Hyde 40 amino acid sequence:

```
  1 MPEEMDKPLI SLHLVDSDSS LAKVPDEAPK
    VSILGSGDFA RSLATRLVGS GPKWVVVGSRN

61 PKRTARLFPS AAQVTFQEEA VSSPEVIFVA
    VFREHYSSLC SLSDQLAGKI LVDVSNPTEQ

121 EHLQHRESNA EYLASLFPTC TVVKAFNVIS
    AWTLQAGPRD GNGQVPICGD QPEAKRAVSE

181 MALAMGFMPV DMGSLASAWE VEAMPLRLLP
    AWKVPTLLAL GLFVCFYAYN FVRDVLQPYV

241 QESQNKFFKL PVSVVNTTLP CVAYVLLSLV
    YLPGVLAAAL QLRRGTKYQR FPDWLDHWLQ

301 HRKQIGLLSF FCAALHALYS FCLPLRRAHR
    YDLVNLAVKQ VLANKSHLWV EEVWRMEIYL

361 SLGVLALGTL SLLAVTSLPS LANSLNWREF
    SFVQCVATSS AGNTGSGTRR PESQSQDPHL

421 PAPHHQTSFL GPRSFCCSLV PVSTPYGHQE
    DLSWTR                              (SEQ ID No.: 4)
```

In one embodiment the p-Hyde gene has a nucleotide sequence having at least 75% similarity with the nucleic acid coding sequence of SEQ ID NO: 5. In another embodiment the nucleic acid has a nucleotide sequence having at least 85% similarity with the nucleic acid coding sequence of SEQ ID NO: 5. In another embodiment the nucleic acid has a nucleotide sequence having at least 90% similarity with the nucleic acid coding sequence of SEQ ID NO: 5. In another embodiment the nucleic acid has a nucleotide sequence having at least 95% similarity with the nucleic acid coding sequence of SEQ ID NO: 5. In another embodiment the nucleic acid fragment comprises a fragment which begins at the nucleic acid at position 1 of the SEQ ID NO: 5 and ends at position 557 of SEQ ID NO: 5. In another embodiment the nucleic acid comprises a fragment which begins at the nucleic acid at position 1 of SEQ ID NO: 5 and ends at position 158 of SEQ ID NO: 5. In another embodiment the nucleic acid comprises a fragment which begins at the nucleic acid at position 50 of SEQ ID NO: 5 and ends at position 120 of SEQ ID NO: 5. The nucleic acid is DNA, cDNA, genomic DNA, or RNA.

Rat p-Hyde nucleic acid sequence:

```
   1 gaattcggca cgaggctgcc gaggcactgt gatgtccggg gagatggaca
     aaccgctcat 61 cagtcgccgc ttggtggaca gtgatggcag tctggctgag gtccccaagg
     aggctcccaa 121 agtgggcatc ctgggcagcg gggattttgc ccggtccctg gccacacgcc
     tggtgggctc 181 tggcttcttt gtggtggtgg gaagccgtaa ccccaaacgc actgccggcc
     tcttccccctc 241 cttagcccaa gtgactttcc aggaggaggc cgtgagctct ccagaggtca
     tctttgtggc 301 cgtgttccgg gagcactact cctcactgtg cagtcttgct gaccagttgg
     ctggcaagat 361 cctagtggat gtaagcaacc ccacggagaa ggagcgtctt cagcaccgcc
     agtcgaacgc 421 cgagtacctg gcctccctct tcctgcctg cactgtggtc aaggccttca
     acgtcatctc 481 tgcatgggcc ctacaggctg gcccaaggga tgggaacagg caggtgctca
     tctgcggtga 541 ccagctggaa gccaagcaca ccgtctcaga gatggcgcgc gccatgggtt
     tcaccccact 601 ggacatggga tccctggcct cagcgaggga ggtagaggcc atacccctgc
     gcctcttcc 661 atcctggaag gtgcccaccc tcctggccct ggggctaagc acacaaagct
     atgcctacaa 721 cttcatccgg gacgttctac agccgtacat ccggaaagat gagaacaagt
     tctacaagat 781 gccctgtct gtggtcaaca ccacgatacc ctgtgtggct tacgtgctga
     tgtccctggt 841 ttacctgcct ggtgtgctgg cagctgccct tcagctgagg aggggacca
     agtaccagcg 901 cttcccagac tggctggacc attggctgca gcaccgcaag cagatcggge
     tactcagctt 961 tttttccgcc atgctgcacg ctctctacag cttctgcctg ccgctgcgcc
     gctcccaccg 1021 ctatgatctg gtcaacctgg ctgtgaagca ggtcctggcc aacaagagcc
     gcctctgggt 1081 tgaggaagaa gtctggcgga tggagatata cctgtccctg ggtgtgctgg
     ctctgggcat 1141 gctgtcactg ctggcggtta cctcgatccc ttccattgca aactcactca
     actggaagga
```

```
1201 gttcagcttt gtgcagtcca cgctgggctt cgtggccctg atgctgagca
     caatgcacac 1261 cctcacctac ggctggaccc gtgcttttga ggaaaaaccac tacaagttct
     acctgccacc 1321 cacattcacg ctcacgctgc tcctgccctg tgtcatcatc ctggccaagg
     gcctcttcct 1381 cctgccctgc ctcagccaca gactcaccaa gatccgcagg ggctgggaga
     gggatggtgc 1441 cgtcaagttc atgctgcccg ctggccacac acaggggag aaaacaagcc
     acgtgtgagg 1501 ccctggaaat ggagacaggc acagcttgtg ggggcctgg gctgggttcg
     ggtctctttt 1561 ctgggatggt atatgcgtgg gtggccgagg tctgaatttc tgggatgcag
     gtgtatgccg 1621 agatactcag aatggcgtac cacacatgcg ataagtactc acatatattt
     catatataat 1681 aggatttact attattcatta gttaaaaaaa aatagtgggt cctatattt
     caacttatgc 1741 agggtcccta tatttcaact tgagcatttc agagcaaatg ccacacatta
     aacagcagat 1801 cccaccccttg tggtagctgc agagacagac agaaacttct ggttatgaga
     gagactgtat 1861 tttgttggat tctacccttta atccccgttc tctacgttcc cctgttagcc
     acatcttaac 1921 gttggtgcag agctgggaca agagctggct ctggtgcagc ctccccccatc
     ccagggctag 1981 gaaacaagcc tctgatgaac agagggacca ggtctggacc ctcctgctcc
     cgcttccctg 2041 ggctcgagtg gggaggctca gcgggatccc ccgcaatctg tgcaggagtt
     ttcacaggtc 2101 tgtccttttct tccgggagcg gtctgaagcg gccccatctg atcctagctg
     agccgagatt 2161 gttcccccact ccctgaaagt ccagagtcac cgtggagcct gcaaattgct
     ccttctgcga 2221 aggtgtgaag tcaccgtctc accagagcca ttaacgaacc tgatcttcag
     aagaagcata 2281 attgttttccc ctccattaag ttggtggtga ccctctttaa accactgtgc
     cttctcgcct 2341 ttcccatcac taatttgggc atctccatgg agtggactct tgtcggggca
     gttcaggggg 2401 gagggaagca ttagagattg cggagaataa ccatcgaagc ctcccttgga
     tgttcccagg 2461 cgtgccttca ttaaattggt ccctaatgag aatgacaggg gacccctgtt
     gcctgtatgc 2521 agagaaccag ccttctgagc acccaggaaa cacagtggcc ccacgcccctt
     caggggggtc 2581 ccacgtcccc tttcccatgc tttgcctcc ctccctcccg gttacaatca
     accataaaag 2641 tctgcaaata ttgttttttg aattcttaaa gagaccacat cctttgttat
     taccaaaaaa 2701 aaaaaaaaaa aaac                                    (SEQ ID No.: 5)
```

In another embodiment the nucleic acid encodes an amino acid sequence having the sequence as set forth in SEQ ID NO 6. In one embodiment the the amino acid fragment comprises a fragment which begins at the amino acid at position 1 of SEQ ID NO 6 and ends at position 101. In one embodiment the amino acid fragment comprises a fragment which begins at the amino acid at position 1 of SEQ ID NO 6 and ends at position 80. In one embodiment the amino acid fragment comprises a fragment which begins at the amino acid at position 1 of SEQ ID NO 2 and ends at position 60. In one embodiment the the amino acid fragment comprises a fragment which begins at the amino acid at position 61 of SEQ ID NO 6 and ends at position 241. In one embodiment the amino acid fragment comprises a fragment which begins at the amino acid at position 81 of SEQ ID NO 6 and ends at position 361. In one embodiment the amino acid fragment comprises a fragment which begins at the amino acid at position 81 of SEQ ID NO 2 and ends at position 421. In another embodiment the amino acid has at least 70% similarity with the nucleic acid coding sequence of SEQ ID NO 6. In another embodiment the amino acid has at least 75% similarity with the nucleic acid coding sequence of SEQ ID NO 6. In another embodiment the amino acid has at least 80% similarity with the nucleic acid coding sequence of SEQ ID NO 6. In one embodiment the amino acid has at least 85% similarity with the nucleic acid coding sequence of SEQ ID NO 6. In another embodiment the amino acid has at least 90% similarity with the nucleic acid coding sequence of SEQ ID NO 6. In another embodiment the amino acid has at least 95% similarity with the nucleic acid coding sequence of SEQ ID NO 6.

Rat p-Hyde amino acid sequence:

```
  1 MSGEMDKPLI SRRLVDSDGS LAEVPKEAPK
    VGILGSGDPA RSLATRLVGS GFFVVVGSRN

61 PKRTAGLFPS LAQVTFQEEA VSSPEVIFVA
    VFREHYSSLC SLADQLAGKI LVDVSNPTEK

121 ERLQHRQSNA EYLASLFPAC TVVKAFNVIS
    AWALQAGPRD GNRQVLICGD QLEAKHTVSE

181 MARAMGFTPL DMGSLASARE VEAIPLRLLP
    SWKVPTLLAL GLSTQSYAYN FIRDVLQPYI

241 RKDENKFYKM PLSVVNTTIP CVAYVLLSLV
    YLPGVLAAAL QLRRGTKYQR FPDWLDHWLQ

301 HRKQIGLLSP FFAMLHALYS FCLPLRRSHR
    YDLVNLAVKQ VLANKSRLWV EEEVWRMEIY

361 LSLGVLALGM LSLLAVTSIP SIANSLNWKE
    FSFVQSTLGF VALMLSTMHT LTYGWTRAFE

421 ENHYKFYLPP TFTLTLLLPC VIILAKGLFL
    LPCLSHRLTK IRRGWERDGA VKFMLPAGHT

481 QGEKTSHV*                  (SEQ ID NO: 6)
```

Further this invention provides an isolated nucleic acid which encodes an amino acid sequence tccctggccacacgcctg-gtggctctggcttc (SEQ ID NO: 7). Further this invention provides an isolated nucleic acid which encodes an amino acid sequence: AAPCVAYVLLSLVYLPGVLAAALQLR-RGTKYQFRPDWLDHWLQHRKQIGLLSFF (SEQ ID NO: 8). Further this invention provides an isolated nucleic acid, which encodes an amino acid sequence NFIRDV-LQPYIRKDENK (SEQ ID NO: 9).

The invention further encompasses nucleic acid molecules that differ from the nucleotide sequence of SEQ ID NO 1, SEQ ID NO:3, SEQ ID NO:5, or SEQ ID NO:7, due to degeneracy of the genetic code and thus encode the same p-Hyde protein as that encoded by the nucleotide sequence shown in SEQ ID NO: 1, SEQ ID NO:3, SEQ ID NO:5, or SEQ ID NO:7. It will be appreciated by those skilled in the art that DNA sequence polymorphisms that lead to changes in the amino acid sequences of p-Hyde may exist within a population (e.g., the human population). Such genetic polymorphism in the p-Hyde gene may exist among individuals within a population due to natural allelic variation. An allele is one of a group of genes which occur alternatively at a given genetic locus. Such natural allelic variations can typically result in 1–5% variance in the nucleotide sequence of the p-Hyde gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms in p-Hyde that are the result of natural allelic variation and that do not alter the functional activity of p-Hyde are intended to be within the scope of the invention. Moreover, nucleic acid molecules encoding p-Hyde proteins from other species (p-Hyde homologues), which have a nucleotide sequence which differs from that of a human p-Hyde, are intended to be within the scope of the invention. Nucleic acid molecules corresponding to natural allelic variants and homologues of the p-Hyde cDNA of the invention can be isolated based on their identity to the human p-Hyde nucleic acids disclosed herein using the human cDNAs, or a portion thereof, as a hybridization probe according to standard hybridization techniques under stringent hybridization conditions. For example, splice variants of human and mouse p-Hyde cDNA can he isolated based on identity to human and mouse p-Hyde.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6×sodium chloride/sodium citrate (SSC) at about 450 C, followed by one or more washes in 0.2×SSC, 0.1% SDS at 50–650 C. Preferably, an isolated nucleic acid molecule of the invention that hybridizes under stringent conditions to the coding or non-coding (or "sense" or "anti-sense") sequence of SEQ ID NO:1, SEQ ID NO:2, SEQ ID NO:5, or SEQ ID NO:7, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In addition to naturally-occurring allelic variants of the p-Hyde sequence that may exist in the population, the skilled artisan will further appreciate that changes can be introduced by mutation into the nucleotide sequence of SEQ ID NO:1, SEQ ID NO:3, SEQ ID NO:5, or SEQ ID NO:7, thereby leading to changes in the amino acid sequence of the encoded p-Hyde protein, without altering the biological ability of the p-Hyde protein. Mutations can be introduced by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in P-Hyde is preferably replaced with another amino acid residue from the same side chain family. Alternatively, mutations can be introduced randomly along all or part of a P-Hyde coding sequence, such as by saturation mutagenesis, and the resultant mutants can be screened for P-Hyde biological activity to identify mutants that retain activity. Following mutagenesis, the encoded protein can be expressed recombinantly and the activity of the protein can be determined.

In order to avoid severely reducing or eliminating biological activity, amino acid residues that are conserved among the p-Hyde proteins of various species are not altered (except by conservative substitution). Both murine and human p-Hyde protein have a conserved pattern of six cysteine residues. Such conserved domains and cysteine residues are less likely to be amenable to mutation. Other amino acid residues, however, (e.g., those that are not conserved or only semi-conserved among p-Hyde of various species e.g., between murine and human p-Hyde) may not be essential for activity and thus are likely to be amenable to alteration. Accordingly, another aspect of the invention pertains to nucleic acid molecules encoding p-Hyde proteins that contain changes in amino acid residues that are not essential for activity. Such p-Hyde proteins differ in amino acid sequence from SEQ ID NO:2 or SEQ ID NO:4 yet retain biological activity. In one embodiment, the isolated nucleic acid molecule includes a nucleotide sequence encoding a protein that includes an amino acid sequence that is at least about 84% identical, 85%, 90%, 95%, or 98% identical to the amino acid sequence of SEQ ID NO:2, 4, 6, or 8.

The nucleotide encoding p-Hyde includes RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha aromeric nucleic acids, etc.). Also included are synthetic molecules that mimic nucleotides in their ability to bind to a designated sequence via hydrogen bonding and other chemical interactions. Such molecules are known in the art and include, for example, those in which peptide linkages substitute for phosphate linkages in the backbone of the molecule, substantially homologous to primary structural sequence but which include, e.g., in vivo or in vitro chemical and biochemical modifications or which incorporate unusual amino acids. The nucleic acid may be modified. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as 32 P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Ausubel et al., 1992. Besides substantially full-length p-Hyde, the present invention provides for biologically active fragments of the p-hyde which are known to those skilled in the art.

As defined herein an "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"p-Hyde Allele" refers to normal alleles of the p-Hyde locus as well as alleles carrying variations that predispose individuals to develop cancer of many sites including, for example, breast, ovarian, colorectal and prostate cancer. Such predisposing alleles are also called "p-Hyde susceptibility alleles".

"p-Hyde Locus," "p-Hyde Gene," "p-Hyde Nucleic Acids" or "p-Hyde Polynucleotide" each refer to polynucleotides, all of which are in the p-Hyde region, that are likely to be expressed in normal tissue, certain alleles of which predispose an individual to develop breast, ovarian, colorectal and prostate cancers which have p-Hyde activity. Mutations at the p-Hyde locus may be involved in the initiation and/or progression of other types of tumors. The locus is indicated in part by mutations that predispose individuals to develop cancer. These mutations fall within the p-Hyde region described infra. The p-Hyde locus is intended to include coding sequences, intervening sequences and regulatory elements controlling transcription and/or translation. The p-Hyde locus is intended to include all allelic variations of the DNA sequence.

A "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA that has undergone a molecular biological manipulation.

The phrase "nucleic acid encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the native sequence includes the degenerate codons of the native sequence or sequences which may be introduced to provide codon preference in a specific host cell "Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

As used herein, the term "cancer cell" means a tissue that grows by cellular proliferation more rapidly than normal, e.g., more rapidly than adjoining cells, or other cells in the tissue. Neoplastic cells continue to grow after growth stimuli cease. Generally, tumors represent or form a distinct mass of tissue. The present invention relates to both types of tumors, but is particularly valuable in the treatment of cancers.

In one embodiment the cancer cells are selected from a group consisting of: melanoma; lymphoma; leukemia; and prostate, colorectal, pancreatic, breast, brain, or gastric carcinoma. Examples of tumors include but are not limited to: include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, colon carcinoma, pancreatic cancer, breast cancer, ovarian cancer, prostate cancer, squamous cell carcimoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, serinoma, embryonal carcinoma, Wilms' tumor, cervical cancer, germ tumor, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. In a preferred embodiment the tumor is a melanoma or a prostate cell.

Mutations can be made in a nucleic acid encoding p-Hyde such that a particular codon is changed to a codon which codes for a different amino acid but the induction of susceptibility to cell death is maintained. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring struck are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. This isolated nucleic acid also encodes mutant p-Hyde or the wildtype protein.

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to p-Hyde mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

This invention provides for a replicable vector comprising the isolated nucleic acid molecule of the DNA virus. The vector includes, but is not limited to: a plasmid, cosmid, phage or yeast artificial chromosome (YAC) which contains at least a portion of the isolated nucleic acid molecule. As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction and which cuts at that site. Other means are also available and known to an ordinary skilled practitioner. In one embodiment the adenovirus vector is a replication-deficient adenovirus type 5 expression vector. In another embodiment the adenovirus vector comprises an adenovirus genome having a deletion in the E1 and E3 region of the genome and an insertion within the region of a nucleic acid encoding p-Hyde under the control of a promoter. The promoter may be a Rous Sarcoma virus promoter.

Knowledge of the genetic orgaization of adenovirus, a 36 kB, linear and is double-stranded DNA virus, allows substitution of a large piece of adenoviral DNA with foreign sequences up to 7 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use a s a gene transfer vector because of its mid-sized genome, ease of manipulation, high titer, wide target-cell range, and high infectivity. Both ends of the viral genome contain 100–200 base pair Cop) inverted terminal repeats (ITR), which are cis elements necessary for via DNA replication and packaging. The early (E) and late (L) regions of the genome contain different transcription units that are divided by the onset of viral DNA replication. The E1 region E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the E3 or both regions. In nature, adenovirus can package approximately 105% of the wild-type genome, providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the nucleic acid encoding p-Hyde at the position from which the E1 coding sequences have been removed. However, the position of insertion of the p-Hyde coding region within the adenovirus sequences is not critical to the present invention. The nucleic acid encoding a p-Hyde transcription unit also may be inserted in lieu of the deleted E3 region in E3 replacement vectors or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus, demonstrating their safety and therapeutic potential as in vivo gene transfer vectors.

Adenovirus vectors have been used in erotic gene expression and vaccine development. Recently, animal studies suggested that recombinant adenovirus could be used for gene therapy. Experiments in administering recombinant adenovirus to different tissues include trachea instillation, muscle injection, peripheral intravenous injection, and stereotactic inoculation into the brain.

An appropriate promoter arid other necessary vector sequences will be selected so as to be functional in the host, and may include, when appropriate, those naturally associated with p-Hyde genes. Examples of workable combinations of cell lines and expression vectors are described in Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukemia virus, mouse minor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, Cold Spring Harbor, N.Y. (1983).

While such expression vectors may replicate autonomously, they may also replicate by being inserted into the genome of the host cell, by methods well known in the art. Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG.

Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

Viral promoters, cellular promoters/enhancers and inducible promoters/enhancers that could be used in combination with the nucleic acid encoding a p-Hyde in an expression construct include but are not limited to the following: Immunoglobulin Heavy Chain; Immunoglobulin Light Chain; T-Cell Receptor; HLA DQ alpha and DQ beta; beta-Interferon; Interleukin-2; Interleukin-2 Receptor, MHC Class II 5 alpha; MHC Class II HLA-DR alpha; beta-Actin; Muscle Creatine Kinase; Prealbumin (Transthyretin); Elastase I; Metallothionein; Collagenase; Albumin Gene; alpha-Fetoprotein; tau-Globin; beta-Globin; cos; c-HA-ras; Neural Cell Adhesion Molecule (NCAM); alpha 1-Antitrypsin; H2B (TH2B) Histone; Mouse or Type I Collagen; Glucose-Regulated Proteins (GRP94 and GRP78); Rat Growth Hormon; Human Serum Amyloid A (SAA), Troponin I (TN I); Platelet-Derived Growth Factor, Duchenne Muscular; SV40; Polyoma; Retroviruses; Papilloma Virus; Hepatitis B Virus; Human Immunodeficiency Virus; Cytomegaovirus; Gibbon Ape Leukemia Virus; MT II; MMTV (mouse mammary Glucocorticoids; Adenovirus 5 E2.

Additionally any promoter/enhancer combination (as per the Eukaryotic Promoter Data Base EPDB) could also be used to drive expression of a p-Hyde. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

This invention provides a host cell containing the above vector. The host cell may contain the isolated DNA molecule artificially introduced into the host cell. The host cell may be a eukaryotic or bacterial cell (such as *E.coli*), yeast cells, fungal cells, insect cells and animal cells. Suitable animal cells include, but are not limited to Vero cells, HeLa cells, Cos cells, CV1 cells and various mammalian cells.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, p-Hyde protein can be expressed in bacterial cells such as *E. coli*, insect cells, yeast or mammalian cells (such as Chinese hamster ovary cells (CHO) or COS cells). other suitable host cells are known to those skilled in the art Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest.

Preferred selectable markers include those which confer resistance to drugs, such as G418, hygromycin and methotrexate. Nucleic acid encoding a selectable marker can be introduced into a host cell on the same vector as that encoding p-Hyde or can be introduced on a separate vector. Cells stably transfected with the introduced nucleic acid can be identified by drug selection (e.g., cells that have incorporated the selectable marker gene will survive, while the other cells die). A host cell of the invention, such as a prokaryotic or eukaryotic host cell in culture, can be used to produce (i.e., express) p-Hyde protein.

Accordingly, the invention further provides methods for producing p-Hyde protein using the host cells of the invention. In one embodiment, the method comprises culturing the host cell of invention (into which a recombinant expression vector encoding p-Hyde has been introduced) in a suitable medium such that p-Hyde protein is produced. In another embodiment, the method further comprises isolating p-Hyde from the medium or the host cell. The host cells of the invention can also be used to produce nonhuman transgenic animals.

For example, in one embodiment, a host cell of the invention is a fertilized oocyte or an embryonic stem cell into which p-Hyde-coding sequences have been introduced. Such host cells can then he used to create non-human transgenic animals in which exogenous p-Hyde sequences have been introduced into their genome or homologous recombinant animals in which endogenous p-Hyde sequences have been altered. Such animals are useful for studying the function and/or activity of p-Hyde and for identifying and/or evaluating modulators of p-Hyde activity. As used herein, a "transgenic animal', is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc.

A transgenic animal of the invention can be created by introducing p-Hyde-encoding nucleic acid into the male pronuclei of a fertilized oocyte, e.g., by microinjection, retroviral infection, and allowing the oocyte to develop in a pseudopregnant female foster animal. The p-Hyde cDNA sequence e.g., that of (SEQ ID NO:1, 3, 5, or 7) can be introduced as a transgene into the genome of a non-human animal. Alternatively, a nonhuman homologue of the human p-Hyde gene, can be isolated based on hybridization to the human p-Hyde cDNA and used as a transgene. Intronic sequences and polyadenylation signals can also be included in the transgene to increase the efficiency of expression of the transgene. A tissus-specific regulatory sequence(s) can be operably linked to the p-Hyde transgene to direct expression of p-Hyde protein to particular cells. Methods for generating transgenic animals via embryo manipulation and microinjection, particularly animals such as mice, have become conventional in the art and are described for example, in U.S. Pat. Nos. 4,736,866 and 4,870,009, 4,873, 191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the p-Hyde transgene in its genome and/or expression of p-Hyde mRNA in tissues or cells of the animals. A transgenic founder animal can then be used to breed additional animals carrying the transgene. Moreover, transgenic animals carrying a transgene encoding p-Hyde can further be bred to other transgenic animals carrying other transgenes.

To create an homologous recombinant animal, a vector is prepared which contains at least a portion of a p-Hyde gene (e.g., a human or a non-human homolog of the p-Hyde gene, e.g., a murine p-Hyde gene) into which a deletion, addition or substitution has been introduced to thereby alter, e.g., functionally disrupt, the p-Hyde gene. In a preferred embodiment, the vector is designed such that, upon homologous recombination, the endogenous p-Hyde gene is functionally disrupted (i.e., no longer encodes a functional protein; also referred to as a "knock out" vector). Alternatively, the vector can be designed such that, upon homologous recombination, the endogenous p-Hyde gene is mutated or otherwise altered but still encodes functional protein (e.g., the upstream regulatory region can be altered to thereby alter the expression of the endogenous p-Hyde protein).

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, or by computerized implementations of these algorithms (GAP, BESTFIT, FASTA) and TFASTA in the Wisconsin Genetics Software Package Release 7.0, Genetics Computer Group, 575 Science Dr., Madison, Wis.).

"Substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The percent identity between the two sequences is a function of the number of identical positions shared by the sequences (i.e., % identity of identical positions/total # of positions (e.g., overlapping)×100). Preferably, the two sequences are the same length. The determination of percent homology between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to p-Hyde nucleic acid molecules of the invention. BLAST protein searches can be performed with the X13LAST program, score=50, wordlength=3 to obtain amino acid sequences homologous to p-Hyde protein molecules of the invention. To obtain gapped alignments for comparison purposes, Gapped BLAST can be utilized as described in Altschul et al., (1997) Nucleic Acids Res. :3389–3402. When utilizing BLAST and Gapped BLAST programs, the default parameters of the respective programs (e.g., X13LAST and NBLAST) can be used. Another preferred, non-limiting example of a mathematical algorithm utilized for the comparison of sequences is the algorithm of Myers and Miller, CABIOS 4:11–17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, only exact matches are counted.

This invention provides a nucleic acid having a sequence complementary to the sequence of the isolated nucleic acid of the human p-Hyde gene. Specifically, this invention provides an oligonucleotide of at least 15 nucleotides capable of specifically hybridizing with a sequence of nucleotides present within a nucleic acid which encodes the human p-Hyde. In one embodiment the nucleic acid is DNA or RNA. In another embodiment the oligonucleotide is labeled with a detectable marker. In another embodiment the oligonucleotide is a radioactive isotope, a fluorophor or an enzyme Oligonucleotides which are complementary may be obtained as follows: The polymerase chain reaction is then carried out using the two primers. See *PCR Protocols: A Guide to Methods and Applications*. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to a solid phase phosphoramidite triester method using an automated synthesizer. Purification of oligonucleotides is by either native acrylamide gel electrophoresis or by anion-exchange HPLC. The sequence of the synthetic oligonucleotide can be verified using chemical degradation.

High stringent hybridization conditions are selected at about 5° C. lower than the thermal melting point™ for the specific sequence at a defined ionic strength and pH. will be those in which the salt concentration is at least about 0.02 molar at pH 7 and the temperature is at least about 60 C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68C in a 6×SSC solution, washing at room temperature with 6×SSC solution, followed by washing at about 68 C in a 6×SSC in a 0.6×SSX solution.

Hybridization with moderate stringency may be attained for example by: 1) filter pre-hybridizing and hybridizing with a solution of 3×sodium chloride, sodium citrate (SSC), 50% formamide, 0.1M Tris buffer at Ph 7.5, 5×Denhardt's solution; 2) pre-hybridization at 37° C. for 4 hours; 3) hybridization at 37° C. with an amount of labeled probe equal to 3,000,000 cpm total for 16 hours; 4) wash in 2×SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Ausaubel, F. et al.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the pathogenic organism or disease marker to which the relevant sequence listing relates.

The primer pairs of the present invention are useful for determination of the nucleotide sequence of a particular p-Hyde allele using PCR. The pairs of single-stranded DNA primers can be annealed to sequences within or surrounding the p-Hyde gene in order to prime amplifying DNA synthesis of the p-Hyde gene itself. A complete set of these primers allows synthesis of all of the nucleotides of the p-Hyde gene coding sequences, i.e., the exons. The set of primers preferably allows synthesis of both intron and exon sequences. Allele-specific primers can also be used. Such primers anneal only to particular p-Hyde mutant alleles, and thus will only amplify a product in the presence of the mutant allele as a template.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by a phosphoramidite method, or by a triester method. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The nucleic acid of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

Also, this invention provides an antisense molecule capable of specifically hybridizing with the isolated nucleic acid of the human p-Hyde gene. This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein Antisense nucleotides or polynucleotide sequences are useful in preventing or diminishing the expression of the p-Hyde gene, as will be appreciated by those skilled in the art. For example, polynucleotide vectors containing all or a portion of the p-Hyde gene or other sequences from the p-Hyde region (particularly those flanking the p-Hyde gene) may be placed under the control of a promoter in an antisense orientation and introduced into a cell. Expression of such an antisense construct within a cell will interfere with p-Hyde transcription and/or translation and/or replication. Oligomers of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention provides a polypeptide comprising the amino acid sequence of a human p-Hyde. In one embodiment the amino acid sequence is set forth in SEQ ID NOs. 2, 4, 6 or 8. This invention provides a fusion protein or chimeric comprising the polypeptide. This invention provides an antibody which specifically binds to the polypeptide. In one embodiment the antibody is a monoclonal or polyclonal antibody.

The invention also provides p-Hyde chimeric or fusion proteins. As used herein, a p-Hyde "chimeric protein" or "fusion protein" comprises a p-Hyde polypeptide operably linked to a non-p-Hyde polypeptide. A "p-Hyde polypeptide" refers to a polypeptide having an amino acid sequence corresponding to p-Hyde, whereas a "non-p-Hyde polypeptide" refers to a polypeptide having an amino acid sequence corresponding to a protein which is not substantially identical to the p-Hyde protein, e.g., a protein which is different from the p-Hyde protein and which is derived from the same or a different organism. Within a p-Hyde fusion protein the p-Hyde polypeptide can correspond to all or a portion of a p-Hyde protein, preferably at least one biologically active portion of a p-Hyde protein.

Within the fusion protein, the term "operably linked" is intended to indicate that the p-Hyde polypeptide and the non-p-Hyde polypeptide are fused in-frame to each other. The non-p-Hyde polypeptide can be fused to the N-terminus or C-terminus of the p-Hyde polypeptide. In yet another embodiment, the fusion protein is an p-Hyde-immunoglobulin fusion protein in which all or part of p-Hyde is fused to sequences derived from a member of the immunoglobulin protein family. The p-Hyde immunoglobulin fusion proteins of the invention can be incorporated into pharmaceutical compositions and administered to a subject.

The present invention further provides methods of preparing a polynucleotide comprising polymerizing nucleotides to yield a sequence comprised of at least eight consecutive nucleotides of the p-Hyde locus; and methods of preparing a polypeptide comprising polymerizing amino acids to yield a sequence comprising at least five amino acids encoded within the p-Hyde locus.

The present invention provides an isolated polynucleotide comprising all, or a portion of the p-Hyde locus or of a mutated p-Hyde locus. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the p-Hyde locus or its expression product in an analyte. Such methods may further comprise the step of amplifying the portion of the p-Hyde locus, and may further include a step of providing a set of polynucleotides which are primers for amplification of said portion of the p-Hyde locus. The method is useful for either diagnosis of the predisposition to cancer or the diagnosis or prognosis of cancer.

This invention also provides a method of producing a polypeptide encoded by isolated DNA molecule, which comprises growing the above host vector system under suitable conditions permitting production of the polypeptide and recovering the polypeptide so produced.

Further, the isolated polypeptide encoded by the isolated DNA molecule may be linked to a second polypeptide encoded by a nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated DNA molecule. In one embodiment the antibody is a monoclonal antibody. In another embodiment the antibody is a polyclonal antibody. The antibody or DNA molecule may be labelled with a detectable marker including, but not limited to: a radioactive label, or a colorimetric, a luminescent, or a fluorescent marker, or gold. Radioactive labels include, but are not limited to $^{3}H$, $^{14}C$, $^{32}P$, $^{33}P$; $^{35}S$, $^{36}Cl$, $^{57}Co$, $^{59}Co$, $^{59}Fe$, $^{90}Y$, $^{125}I$, $^{131}I$, and $^{186}Re$. Fluorescent makers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detect by a second antibody which may be linked to an enzyme, such as alkaline phosphatase or horseradish peroxidase. Other enzymes which may be employed are well known to one of ordinary skill in the art.

"Specifically binds to an antibody" or "specifically immunoreactive with", when referring to a protein or peptide, refers to a binding reaction which is determinative of the presence of the p-Hyde of the invention in the presence of a heterogeneous population of proteins and other biologics including viruses other than the p-Hyde. Thus, under designated immunoassay condition, the specified antibodies bind to the p-Hyde antigens and do not bind in a significant amount to other antigens present in the sample. Specific binding to an antibody under such conditions may require an antibody that is selected for its specificity for a particular protein. For example, antibodies raised to the human p-Hyde immunogen described herein can be selected to obtain antibodies specifically immunoreactive with the p-Hyde proteins and not with other proteins. These antibodies recognize proteins homologous to the human p-Hyde protein. A variety of immunoassay formats may be used to select antibodies specifically immunoreactive with a particular protein For example, solid-phase ELISA immunoassays are routinely used to select monoclonal antibodies specifically immunoreactive with a protein.

This invention provides a method to select specific regions on the polypeptide encoded by the isolated DNA molecule of the DNA virus to generate antibodies. The protein sequence way be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

The antibodies may be detectably labelled, utilizing conventional labelling techniques well-known to the art. Thus, the antibodies may be radiolabelled using, for example, radioactive isotopes such as $^{3}H$, $^{125}I$, $^{131}I$, and $^{35}S$. The antibodies may also be labelled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exist that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin. Once labeled, the antibody may be employed to identify and quantify immunologic counterparts (antibody or antigenic polypeptide) utilizing techniques well-known to the art.

A description of a radioimmunoassay (RIA) may be found in *Laboratory techniques in Biochemistry and Molecular Biology*, with particular reference to the chapter entitled "An Introduction to Radioimmune Assay and Related Techniques" by Chard, T., incorporated by reference herein. A description of general immunometric assays of various types can be found in the following U.S. Pat. No. 4,376,110 (David et al.) or U.S. Pat. No. 4,098,876 (Piasio).

One can use immunoassays to detect for the p-Hyde gene, specific peptides, or for antibodies to the virus or peptides.

In one embodiment, antibodies to human p-Hyde can be used to detect the agent in the sample. In brief to produce antibodies to the agent or peptides, the sequence being targeted is expressed transfected cells, preferably bacterial cells and purified. The product in injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like.

In a further embodiment of this invention, commercial test kits suitable for use by a medical specialist may be prepared to determine the presence or absence of predetermined binding activity or predetermined binding activity capability to suspected target cells. In accordance with the testing techniques discussed above, one class of such kits will contain at least the labeled polypeptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell. Alterative methods of immortalization include transformation with Epstein Barr Viruses, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies.

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selection of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in *E. coli* is also useful. Examples of such markers include genes specifying resistance to antibiotics. Suitable eukaryote hosts may include plant cells, insect cells, mammalian cells, yeast, and filamentous fungi.

The peptides derived form the nucleic acids, peptide fragments are produced by recombinant technology may be purified by standard techniques well known to those of skill in the art. Recombinantly produced sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods and others.

This invention is directed to analogs of the isolated nucleic acid and polypeptide which comprise the amino acid sequence as set forth above. The analog may have an N-terminal methionine or an N-terminal polyhistidine optionally attached to the N or COOH terminus of the polypeptide which comprise the amino acid sequence.

In another embodiment, this invention contemplates peptide fragments of the polypeptide which result from proteolytic digestion products of the polypeptide. In another embodiment, the derivative of the polypeptide has one or more chemical moieties attached thereto. In another embodiment the chemical moiety is a water soluble polymer. In another embodiment the chemical moiety is polyethylene glycol. In another embodiment the chemical moiety is mono-, di-, tri- or tetrapegylated. In another embodiment the chemical moiety is N-terminal monopegylated.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

Attachment of polyethylene glycol (PEG) to compounds in particularly useful because PEG has very low toxicity in mammals (Carpenter et al., *Toxicol Appl Pharmacol.* 1971 January; 18(1):35–40). For example, a PEG adduct of adenosine deaminase was approved in the United States for use in humans for the treatment of severe combined immunodeficiency syndrome. A second advantage afforded by the conjugation of PEG is that of effectively reducing the immunogenicty and antigenicity of heterologous compounds. For example, a PEG adduct of a human protein might be useful for the treatment of disease in other mammal species without the risk of triggering a severe immune response. The compound of the present invention may be delivered in a microencapsulation device so as to reduce or prevent an host immune response against the compound or against cells which may produce the compound. The compound of the present invention may also be delivered microencapsulated in a membrane, such as a liposome.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment, the amino acid residues of the polypeptide described herein are preferred to be in the "L" isomeric form. In another embodiment, the residues in the "D" isomeric form can be substituted for any L-amino acid residue, as long as the desired functional property of lectin activity is retained by the polypeptide. $NH_2$ refers to the free amino group present at the amino terminus of a polypeptide. COOR refers to the free carboxy group present at the carboxy terminus of a polypeptide. Abbreviations used herein are in keeping with standard polypeptide nomenclature, *J. Biol. Chem.*, 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Synthetic polypeptide, prepared using the well known techniques of solid phase, liquid phase, or peptide condensation techniques, or any combination thereof, can include natural and unnatural amino acids. Amino acids used for peptide synthesis may be standard Boc(N-amino protected N-t-butyloxycarbonyl) amino acid resin with the standard deprotecting, neutralizaton, coupling and wash protocols of the original solid phase procedure of Merrifield (1963, J. Am. Chem Soc. 85:2149–2154), or the base-labile N-amino protected 9-fluorenylmethoxycarbonyl (Fmoc) amino acids first described by Carpino and Han (1972, J. Org. Chem. 37:3403–3409). Thus, polypeptide of the invention may comprise D-amino acids, a combination of D- and L-amino acids, and various "designer" amino acids (e.g., methyl amino acids, C-methyl amino acids, and N-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, alpha-helices, alpha turns, beta sheets, beta-turns, and cyclic peptides can be generated.

In one aspect of the invention, the peptides may comprise a special amino acid at the C-terminus which incorporates either $CO_2H$ or $CONH_2$ side chain to simulate a free glycine or a glycine-amide group. Another way to consider this special residue would be as a D or L amino acid analog with a side chain consisting of the liner or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

A constrained, cyclic or rigidized peptide may be prepared synthetically, provided that in at least two positions in the sequence of the peptide an amino acid or amino acid analog is inserted that provides a chemical functional group capable of cross-lining to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as carboxyl-glutamic acid (Gla) (Bachem) to chelate a transition metal and form a cross-link. Protected carboxyl glutamic acid may be prepared by modifying he synthesis described by Zee-Cheng and Olson (1980, Biophys. Biochem. Res. Commun. 94:1128–1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides; Analysis, Synthesis, Biology, Vol. 3, Gross and Meienhofer, eds., Academic Press: New York, pp. 137–167; Ponsanti et al., 1990, Tetrahedron 46:925–8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); γ-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6carboxylic acid), a dipeptide analog (Kemp et al., 1985, J. Org. Chem. 50:5834–5838); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention Modifications of peptides are well known to one of ordinary skill, and include phosphorylation, carboxymethylation, and acylation. Modifications may be effected by chemical or enzymatic means. In another aspect, glycosylated or fatty acylated peptide derivatives way be prepared. Preparation of glycosylated or fatty acylated peptides is well known in the arts. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in the peptide. This and other peptide-fatty acid conjugates suitable for use in the present invention are disclosed in U.K. Patent GB-8809162.4 and International Patent Application PCT/AU89/00166.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Chemical Moieties for Derivatization

Chemical moieties suitable for derivatization, may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

This invention provides a method for determining whether a subject carries a mutation in the p-Hyde gene which comprises: a) obtaining an appropriate nucleic acid sample from the subject; and (b) determining whether the nucleic acid sample from step (a) is, or is derived from, a nucleic acid which encodes mutant p-Hyde so as to thereby determine whether a subject carries a mutation in the p-Hyde gene. In one embodiment, the nucleic acid sample in step (a) comprises mRNA corresponding to the transcript of DNA encoding a mutant p-Hyde, and wherein the determining of step (b) comprises: (i) contacting the mRNA with the oligonucleotide under conditions permitting binding of the mRNA to the oligonucleotide so as to form a complex; (ii) isolating the complex so formed; and (i) identifying the mRNA in the isolated complex so as to thereby determine whether the mRNA is, or is derived from, a nucleic acid which encodes mutant p-Hyde. In another embodiment, the determining of step (b) comprises: i) contacting the nucleic acid sample of step (a), and the isolated nucleic acid with restriction enzymes under conditions permitting the digestion of the nucleic acid sample, and the isolated nucleic acid into distinct, distinguishable pieces of nucleic acid; (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant p-Hyde.

The present invention further provides methods of preparing a polynucleotide comprising polymerizing nucleotides to yield a sequence comprised of at least eight consecutive nucleotides of the p-Hyde gene; and methods of preparing a polypeptide comprising polymerizing amino acids to yield a sequence comprising at least five amino acids encoded within the p-Hyde gene.

This invention provides a pharmaceutical composition comprising an amount of the polypeptide and a pharmaceutically effective carrier or diluent.

This invention provides a method for determining whether a subject carries a mutation in the p-Hyde gene which comprises: (a) obtaining an appropriate nucleic acid sample from the subject; and (b) determining whether the nucleic acid sample from step (a) is, or is derived from, a nucleic acid which encodes mutant p-Hyde so as to thereby determine whether a subject carries a mutation in the p-Hyde gene. In one embodiment the nucleic acid sample in step (a) comprises mRNA corresponding to the transcript of DNA encoding a mutant p-Hyde, and wherein the determining of step (b) comprises: (i) contacting the mRNA with the oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant p-Hyde. In another embodiment the determining of step (b) comprises: (i) contacting the nucleic acid sample of step (a), and the isolated nucleic acid of claim 1 with restriction enzymes under conditions permitting the digestion of the nucleic acid sample and the isolated nucleic acid into distinct, distinguishable pieces of nucleic acid, (ii) isolating the pieces of nucleic, acid, and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant p-Hyde.

Detection of point mutations or variations may be accomplished by molecular cloning of the p-Hyde allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined. There are six well known methods for a more complete, yet still indirect, test for confirming the presence of a susceptibility allele: 1) single stranded conformation analysis (SSCA) 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. For allele-specific PCR, primers are used which hybridize at their 3' ends to a particular p-Hyde mutation. If the particular p-Hyde mutation is not present, an amplification product is not observed. Amplification Refractory Mutation System (ARMS) can also be used, is disclosed in European Patent Application Publication No. 0332435. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the p-Hyde mutation found in that individual. Other techniques for detecting insertions and deletions as known in the art can be used.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR (see below) before hybridization. Changes in DNA of the p-Hyde gene can also be detected using Southern hybridization, especially if the changes are gross rearrangements, such as deletions and insertions.

As noted above, non-PCR based screening assays are also contemplated in this invention This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a 10 sup 3–10 sup 6 increase in sensitivity.

Two-step label amplification methodologies are known in the art. These assays work on the principle that a small ligand (such as digoxigenin, biotin, or the like) is attached to a nucleic acid probe capable of specifically binding p-Hyde. Allele specific probes are also contemplated within the scope of this example. In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate.

In a second example, the small ligand is recognized by a second ligand-enzyme conjugate that is capable of specifically complexing to the first ligand. A well known embodiment of this example is the biotin-avidin type of interactions.

It is also contemplated within the scope of this invention that the nucleic acid probe assays of this invention will employ a cocktail of nucleic acid probes capable of detecting p-Hyde. Thus, in one example to detect the presence of p-Hyde in a cell sample, more than one probe complementary to p-Hyde is employed and in particular the number of different probes is alternatively 2, 3, or 5 different nucleic acid probe sequences. In another example, to detect the presence of mutations in the p-Hyde gene sequence in a patient more than one probe complementary to p-Hyde is employed where the cocktail includes probes capable of patients with alternate-specific mutations identified in populations of patients with alterations in p-Hyde. In this embodiment, any number of probes can be used, and will preferably include probes corresponding to the major gene mutations identified as predisposing an individual to breast cancer.

This invention provides a method for screening a tumor sample from a human subject for a somatic alteration in a p-Hyde gene in said tumor which comprises gene comparing a first sequence selected form the group consisting of a p-Hyde gene from said tumor sample, p-Hyde RNA from said tumor sample and p-Hyde cDNA made from mRNA from said tumor sample with a second sequence selected from the group consisting of p-Hyde gene from a nontumor sample of said subject, p-Hyde RNA from said nontumor sample and p-Hyde cDNA made from mRNA from said nontumor sample, wherein a difference in the sequence of the p-Hyde gene,p-Hyde RNA or p-Hyde cDNA from said tumor sample from the sequence of the p-Hyde gene, p-Hyde RNA or p-Hyde cDNA from said nontumor sample indicates a somatic alteration in the p-Hyde gene in said tumor sample.

This invention provides a method for screening a tumor sample from a human subject for the presence of a somatic alteration in a p-Hyde gene in said tumor which comprises comparing p-Hyde polypeptide from said tumor sample from said subject to p-Hyde polypeptide from a nontumor sample from said subject to analyze for a difference between the polypeptides, wherein said comparing is performed by (i) detecting either a full length polypeptide or a truncated polypeptide in each sample or (ii) contracting an antibody which specifically binds to either an epitope of an altered p-Hyde polypeptide, or an epitope of a wild-type p-Hyde polypeptide to the p-Hyde polypeptide from each sample and detecting antibody binding, wherein a difference between the p-Hyde polypeptide from said tumor sample from the p-Hyde polypeptide from said nontumor sample indicates the presence of a somatic alteration in the p-Hyde gene in said tumor sample.

This invention is particularly useful for screening compounds by using the p-Hyde polypeptide or binding fragment thereof in any of a variety of drug screening techniques. The p-Hyde polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a p-Hyde polypeptide or fragment and the agent being tested, or examine the degree to which the formation of a complex between a p-Hyde polypeptide or fragment and a known ligand is interfered with by the agent being tested.

Thus, the present invention provides methods of screening for drugs comprising contacting such an agent with a p-Hyde polypeptide or fragment thereof and assaying (i) for the presence of a complex between the agent and the p-Hyde polypeptide or fragment, or (ii) for the presence of a complex between the p-Hyde polypeptide or fragment and a ligand, by methods well known in the art. In such competitive binding assays the p-Hyde polypeptide or fragment is typically labeled. Free p-Hyde polypeptide or fragment is separated from that present in a protein:protein complex, and the amount of free (i.e., uncomplexed) label is a measure of the binding of the agent being tested to p-Hyde or its interference with p-Hyde:ligand binding, respectively.

Another technique for drug screening provides throughout screening for compounds having suitable binding affinity to the p-Hyde polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with p-Hyde polypeptide and washed. Bound p-Hyde polypeptide is then detected by methods well known in the art.

Purified p-Hyde, can be coated directly onto plates for use in the aforementioned drug screening techniques. However, non-neutralizing antibodies to the polypeptide can be used to capture antibodies to immobilize the p-Hyde polypeptide on the solid phase. This invention also contemplates the use of competitive drug screening assays in which neutralizing antibodies capable of specifically binding the p-Hyde polypeptide compete with a test compound for binding to the p-Hyde polypeptide or fragments thereof. In this manner, the antibodies can be used to detect the presence of any peptide which shares one or more antigenic determinants of the p-Hyde polypeptide.

A further technique for drug screening involves the use of host eukaryotic cell lines or cells (such as described above) which have a nonfunctional p-Hyde gene. These host cell lines or cells are defective at the p-Hyde polypeptide level. The host cell lines or cells are grown in the presence of drug compound. The rate of growth of the host cells is measured to determine if the compound is capable of regulating the growth of p-Hyde defective cells.

The goal of rational drug design is to produce structural analogs of biologically active polypeptides of interest or of small molecules with which they interact (e.g., agonists, antagonists, inhibitors) in order to fashion drags which are, for example, more active or stable forms of the polypeptide, or which, e.g., enhance or interfere with the function of a polypeptide in vivo. See, e.g., Hodgson, *Biotechnology (NY)*. 1991 January;9(1):19–21. In one approach, one first determines the three-dimensional structure of a protein of interest (e.g., p-Hyde polypeptide) or, for example, of the p-Hyde-receptor or ligand complex, by x-ray crystallography, by computer modeling or most typically, by a combination of approaches. Less often, useful information regarding the structure of a polypeptide may be gained by modeling based on the structure of homologous proteins. In addition, peptides (e.g., p-Hyde polypeptide) are analyzed by an alanine scan. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved p-Hyde polypeptide activity or stability or which act as inhibitors, agonists, antagonists, etc. of p-Hyde polypeptide activity. By virtue of the availability of cloned p-Hyde sequence, sufficient amounts of the p-Hyde polypeptide may be made available to perform such analytical studies as x-ray crystallography. In addition, the knowledge of the p-Hyde protein sequence provided herein will guide those employing computer modeling techniques in place of, or in addition to x-ray crystallography.

This invention provides a method for identifying a chemical compound which is capable inducing susceptibility to cell death which comprises: (a) contacting the p-Hyde with a chemical compound under conditions permitting binding between the p-Hyde and the chemical compound; (b) detecting specific binding of the chemical compound to the p-Hyde; and (c) determining whether the chemical compound inhibits the p-Hyde so as to identify a chemical compound which is capable of capable inducing susceptibility to cell death. Useful diagnostic techniques include, but are not limited to fluorescent in situ hybridization (FISH), direct DNA sequencing, PFGE analysis; Southern blot analysis, single stranded conformation analysis (SSCA), Rnase protection assay, allele-specific oligonucleotide (ASO), dot blot analysis and PCR-SSCP, as discussed in detail further below.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of tumors. Southern blots displaying hybridizing fragment (differing in length from control DNA when probed with sequences near or including the p-Hyde gene) indicate a possible mutation. If restriction enzymes which produce very large restriction fragments are used, then pulsed field gel electrophoresis (PFGE) is employed.

Detection of point mutations may be accomplished by molecular cloning of the p-Hyde allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined. There are six well known methods for a more complete, yet still indirect, test for confirming the presence of a susceptibility allele: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. For allele-specific PCR, primers are used which hybridize at their 3' ends to a particular p-Hyde mutation. If the particular p-Hyde mutation is not present, an amplification product is not observed. Amplification Refractory Mutation System (ARMS) can also be used, is disclosed in European Patent Application Publication No. 0332435. Insertions and deletions of genes can also be detected by cloning, sequencing and amplification. In addition, restriction fragment length polymorphism (RFLP) probes for the gene or surrounding genes can be used to score alteration of an allele or an insertion in a polymorphic fragment. Such a method is particularly useful for screening relatives of an affected individual for the presence of the p-Hyde mutation found in that individual. Other techniques for detecting insertions and deletions as known in the art can be used.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR (see below) before hybridization. Changes in DNA of the p-Hyde gene can also be detected using Southern hybridization, especially if the changes are gross rearrangements, such as deletions and insertions.

DNA sequences of the p-Hyde gene which have been amplified by use of PCR may also be screened using allele-specific probes. These probes are nucleic acid oligomers, each of which contains a region of the p-Hyde gene sequence harboring a known mutation. For example, one oligomer may be about 30 nucleotides in length, corresponding to a portion of the p-Hyde gene sequence. By use of a battery of such allele-specific probes, PCR amplification products can be screened to identify the presence of a previously identified mutation in the p-Hyde gene. Hybridization of allele-specific probes with amplified p-Hyde sequences can be performed, for example, on a nylon filter. Hybridization to a particular probe under stringent hybridization conditions indicates the presence of the same mutation in the tumor tissue as in the allele-specific probe.

Alteration of p-Hyde mRNA expression can be detected by any techniques known in the art. These include Northern blot analysis, PCR amplification and RNase protection. Diminished mRNA expression indicates all alteration of the wild-type p-Hyde gene.

Alteration of wild-type p-Hyde genes can also be detected by screening for alteration of wild-type p-Hyde proteins. For example, monoclonal antibodies immunoreactive with p-Hyde can be used to screen a tissue. Lack of cognate antigen would indicate a p-Hyde mutation. Antibodies specific for products of mutant alleles could also be used to detect mutant p-Hyde gene product. Such immunological assays can be done in any convenient formats known in the art. These include Western blots, immunohistochemical assays and ELISA assays. Any means for detecting an altered p-Hyde protein can be used to detect alteration of wild-type p-Hyde genes. Functional assays, such as protein binding determination, can be used. In addition, assays can be used which detect p-Hyde biochemical function. Finding a mutant p-Hyde gene product indicates alteration of a wild-type p-Hyde gene. Mutant p-Hyde genes or gene products can also be detected in other human body samples, such as serum, stool, urine and sputum.

The present invention also provides for fusion polypeptides, comprising p-Hyde polypeptides and fragments. Homologous polypeptides may be fusions between two or more p-Hyde polypeptide sequences or between the sequences of p-Hyde and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor. Fusion proteins will typically be made by either recombinant nucleic acid methods, as described below, or may be chemically synthesized.

Probes for p-Hyde alleles may be derived from the sequences of the p-Hyde region or its cDNAs. The probes may be of any suitable length, which span all or a portion of the p-Hyde region, and which allow specific hybridization to the p-Hyde region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. The probes will include an isolated polynucleotide attached to a label or reporter molecule and may be used to isolate other polynucleotide sequences, having sequence similarity by standard methods. For techniques for preparing and labeling probes see, e.g., Ausubel et al., 1992

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art. Portions of the polynucleotide sequence having at least about eight nucleotides, usually at least about 15 nucleotides, and fewer than about 6 kb, usually fewer than about 1.0 kb, from a polynucleotide sequence encoding p-Hyde are preferred as probes, The probes may also be used to determine whether mRNA encoding p-Hyde is present in a cell or tissue.

This invention provides a method of inhibiting the growth of cancer cells, comprising the steps of obtaining the cell and contacting the cells of the subject with a replication-deficient adenovirus type 5 expression vector comprising an adenovirus genome having a deletion in the E1 and E3 region of the genome and an insertion within the region of a nucleic acid encoding p-Hyde under the control of a Rous Sarcoma virus promoter, thereby inhibiting the growth of the prostate cancer cells.

This invention provides a method of inhibiting the growth a prostate cancer cells, comprising: 1) obtaining a sample of prostate cells from a subject; 2) contacting the cells with a replication deficient adenovirus type 5 expression vector which comprises an adenovirus genome having a deletion in the E1 and E3 regions of the genome and an insertion within the regions of a p-Hyde cDNA under the control of a Rous Sarcoma virus promoter, and 3) introducing the cells into the subject, thereby inhibiting the growth of the cancer cells.

This invention provides a method of suppressing the growth of cancer cells in a subject, comprising introducing into the cancer cell an amount of a nucleic acid encoding a p-Hyde protein, a nucleic acid encoding a fragment of p-Hyde protein, or the nucleic acid encoding a mutant p-Hyde protein, thereby suppressing the growth of cancer cells in the subject.

This invention provides a method of suppressing growth of cancer cells in a subject, comprising administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby suppressing the growth of cancer cells in the subject.

As demonstrated herein apoptotic response was assessed using DNA laddering assay. DNAs were extracted after the respective treatment (24 hours with 1 mM Hydroxyurea followed by 24 hours with 0.1 mM 5'-dFUrd) and analyzed on 1.6% agarose gel electrophoresis. In agreement with cell cycle analyses, apoptotic response of the stable transfectants AT1-H1 and AT3-H1 (pcHYDE transfected AT-1 and AT-3) are consistently and significantly higher relative to both parental (AT-1 and AT-3) and pcDNA-transfected parental cell lines (AT1-pcl and AT3-pcl). In particular, the highest apoptotic response occurred in synchronized culture under the induction with 0.1 mM 5'-dFUrd as shown in FIG. 15. The enhanced apoptotic response in AT1-H1 and AT3-H1 transfectant after hydroxyurea treatment is the result of "thymineless death" (Kyprianou, 1994, Kyprianou et al., 1994) leading to depletion of intracellular thymidine-5-triphosphate (TTP) pools through indirect inhibition of thymidylate synthetase by fluorodeoxyuridine. However, the exact mechanism of the apoptosis itself in association with TTP depletion is not known. Taken together, these data suggest that the apoptotic response in the pcHYDE stable transfectants is likely due to the downstream effect of pcHYDE gene product.

This invention provides a method of inducing susceptibility to apoptosis of cancer cells, comprising introducing into the cancer cell an amount of a nucleic acid encoding a p-Hyde protein, a nucleic acid encoding a fragment of p-Hyde protein, or the nucleic acid encoding a mutant p-Hyde protein, thereby inducing susceptibility to apoptosis.

This invention provides a method of inducing susceptibility to apoptosis of cancer cells in a subject, comprising administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby inducing susceptibility to apoptosis.

Figure 9:
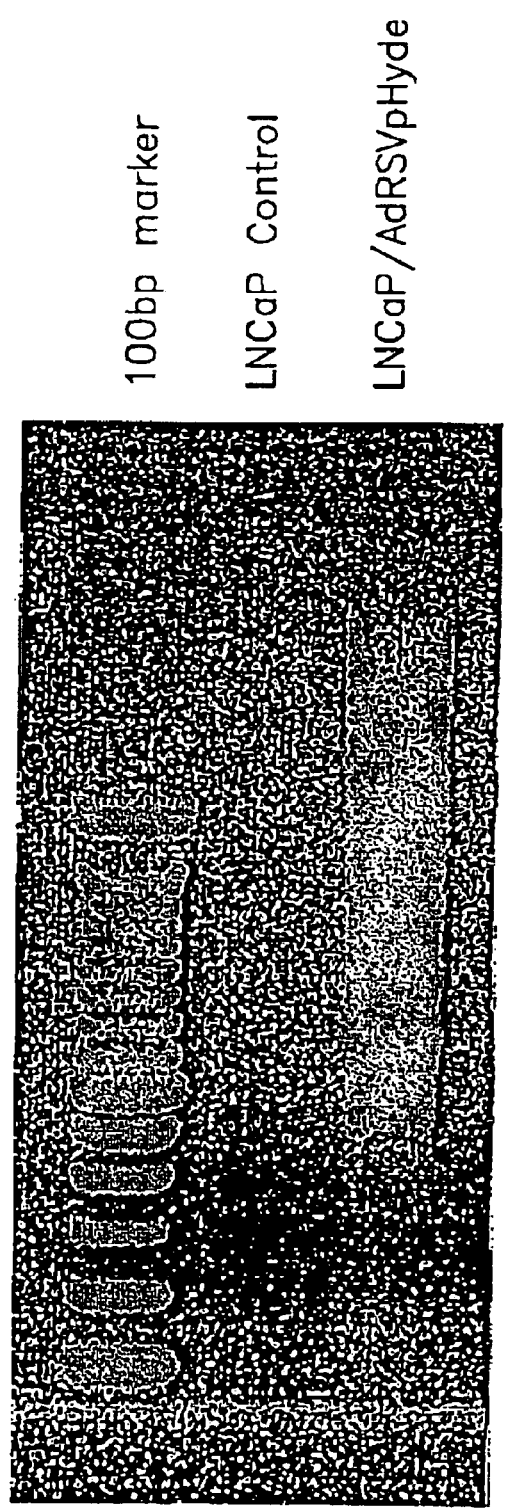
FIG. 9. AdRSVp-Hyde induced apoptosis in LNCaP cells. Cells were untreated or transduced by AdRSVpHyde at MOI=100, supernatant were collected 48 h post transduction. Soluble DNA was extracted from floating cells and electrophoresed on a 2% agarose gel.

As demonstrated herein, p-Hyde suppresses cancer growth in vivo. The lowest level of p-Hyde expression was observed in AT3 cell line as shown in FIG. 9. For this reason, AT3 cell line was transfected with pcHYDE, a construct of p-Hyde in mammalian expression vector of pcDNA3.1(−) under G418 selection. As negative control , AT-3 cell line was also transfected with the vector only and the stable transfectants obtained was designated as AT3-pc. Thee tumor growth of the parental cell line of AT-3 and in stable transfectant AT3-H1 and AT3-H2 have been evaluated in vivo. One million cells of each cell lines in 0.3 ml of Hanks solution were inoculated subcutaneously in each flank of inbred male Copenhagen rat. In this initial experiment, three groups of each five rats were injected with each cell line. The size of tumors were scored after a time schedule shown in FIG. 18. These preliminary results indicated that both AT3-H1 and AT3-H2 stable transfectant grew significantly slower than the AT-3 parental cell line demonstrating that the tumor growth regression in both stable transfectants and regulated by the pcHYDE gene product.

Interestingly, p-Hyde has the dual ability to act like a tumor suppressor gene and induce susceptibility to apoptosis by what may be p53 independent pathways. The growth of prostate tumors in rats was greatly inhibited p-Hyde. Moreover, prostate cancer cells expressing p-Hyde were more sensitive to UV DNA damage driving these cells into cell programmed death. Analysis of DNA repair enzyme activity suggests a defect resulting in the presence of intact (6-4) PP and decreased cell survival by colony forming assay. However, the capacity of p-Hyde to induce susceptibility to apoptosis is not limited to UV DNA damage. Chemotherapy agent, Fluorodeoxyuridine, a pyrimidine antimetabolite which is related to fluorouracil (5-FU) and has been used for treatment of a wide variety of human epithelial malignancies, also more readily induces apoptosis in prostate cancer cell expressing p-Hyde. Moreover, cancer cells expressing p-Hyde are also more susceptible to gamma radiation. Thus, the mechanisms of cellular DNA injury are different for UV, gamma radiation, and Fluorodeoxyuridine suggesting that the ability to make cells more susceptible to apoptosis is more global in action. This unique function of p-Hyde may represent a new class genes that induce susceptibility to apoptosis. This is different than the function ascribed to tumor suppressor genes like p53 which directly induces apoptosis, not sensitivity to apoptosis (Yonish- Rouach et al., 1991). Moreover, p-Hyde activity is in contrast to bcl-2 where the absence of bcl-2, not the presence of, makes the cancer cell more susceptible to cell programmed death (McDonnellet al., 1992).

This invention provides a method of suppressing cancer cells, comprising introducing into the cancer cell an amount of a nucleic acid encoding a p-Hyde protein, a nucleic acid encoding a fragment of p-Hyde protein, or the nucleic acid encoding a mutant p-Hyde protein, thereby inducing susceptibility to apoptosis.

This invention provides a method of suppressing cancer cells a subject, comprising administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby suppressing cancer cells.

This invention provides a method of treating a subject with cancer which comprises administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein and a pharmaceutical acceptable carrier or diluent, thereby treating the subject with cancer.

This invention provides a method of treating a subject with cancer, comprising: 1) administering to the subject a pharmaceutical composition comprising a therapeutically effective amount of a nucleic acid encoding a p-Hyde protein, a nucleic acid encoding a fragment of p-Hyde protein, or the nucleic acid encoding a mutant p-Hyde protein in combination with radiation, chemotherapy, or UV mimetic drugs; and 2) a pharmaceutical acceptable carrier or digest, thereby treating the subject with cancer.

The unique functional features of the p-Hyde gene may be exploited for the treatment of hyperproliferative disorders and cancer. One effective therapeutic strategy, for example, may be the treatment of carcinoma cells expressing p-Hyde with chemotherapy agents or UV mimetic drugs (such as acetylaminofluorine). However, cancer cells are not likely to produce significant levels of the growth inhibition p-Hyde. Consequently, the p-Hyde gene my be introduced into cancer cells by gene therapy. Tumors transduced with vectors containing p-Hyde may not only be directly suppressed by p-Hyde as demonstrated in this study, but also when treated in combination with DNA damaging therapy such as chemotherapy, UV mimetic drugs, or radiation, have even a greater anti-cancer effect. Since gene therapy will target cancer cells, then enhancement of apoptosis will occur more selectively in cancer cells following DNA damage (UV, radiation, or chemotherapy).

Figure 16A:
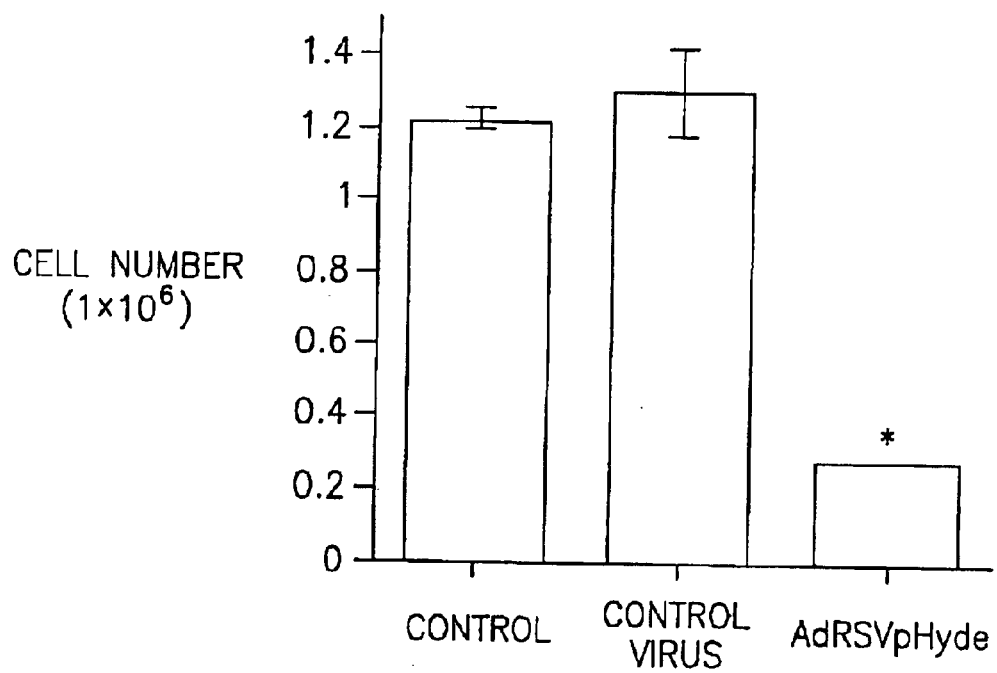
FIGS. 16A and 16B. Inhibitory effects of pHyde on growth of prostate cancer cell lines DU145 and LNCaP. DU145 (A) and LNCaP (B) cells were transduced with or without adenoviral vectors (control virus or AdRSVpHyde) at MOI=100. Cell numbers were counted at day 5 after viral transduction The data represent the results from two independent experiments each performed in duplicate. *Some error bars were too all to see in the figure.
Figure 16B:
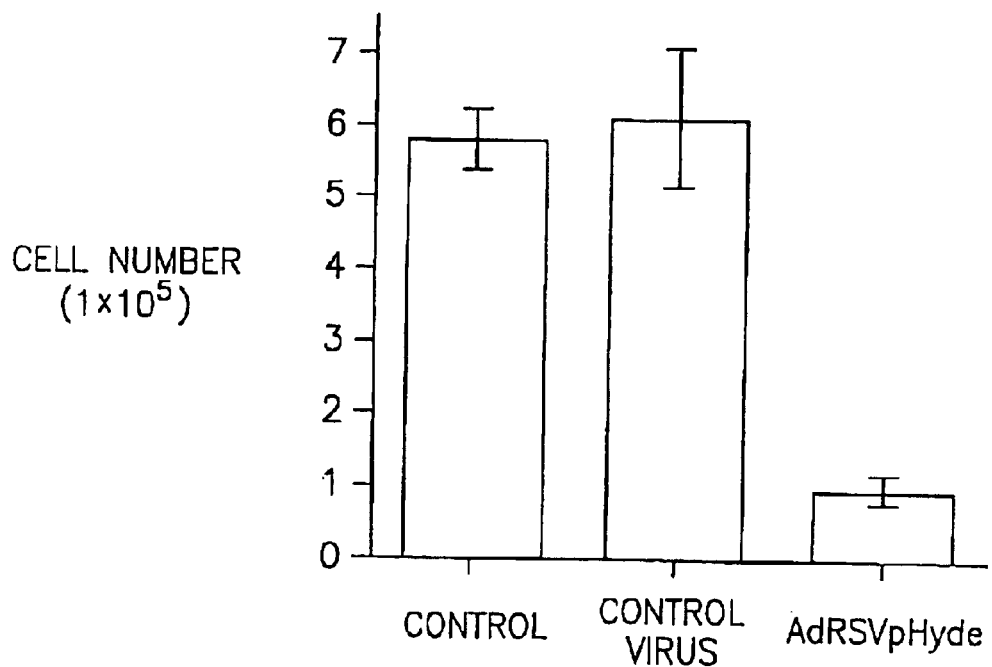

Three DNA enzyme repair systems were evaluated in parental compared to p-Hyde transfected cells: uridine phosphorylase, uridine kinase, and UV damage repair. UV damage repair was impaired in the p-Hyde transfected cells. FIG. 16 shows that decreased DNA repair activity results in higher levels of intact photoproducts (64PP). Consistent with these data, pHyde transfected cells also bad a significant reduction in survival following V exposure compared to parental AT3 cells as determined by colony formation assay. Thus, DNA repair enzyme impairment correlated with shorter survival and induction of apoptosis in prostate cancer cells infected with p-Hyde.

This invention a method of treating a subject with cancer, comprising administering to the subject a therapeutically effective amount of a pharmaceutical composition comprising: 1) an adenovirus type 5 expression vector which comprises an adenovirus genome having a deletion in the E1 and E3 regions of the genome and an insertion within the regions of a full length sense p-Hyde cDNA under the control of a Rous Sarcoma virus promoter, and 2) a suitable carrier or diluent, thereby treating the subject with cancer. In one embodiment the cancer is selected from a group consisting of: melanoma; lymphoma; leukemia; and prostate, colorectal, pancreatic, breast, brain, or gastric carcinoma.

The present invention provides the means necessary for production of gene-based therapies directed at cancer cells. These therapeutic agents may take the form of polynucleotides comprising all or a portion of the p-Hyde locus placed in appropriate vectors or delivered to target cells in more direct ways such that the function of the p-Hyde protein is reconstituted. Therapeutic agents may also take the form of polypeptides based on either a portion of, or the entire protein sequence of p-Hyde. These may functionally replace the activity of p-Hyde in vivo.

A suitable bodily fluid includes, but is not limited to: serum, plasma, cerebrospinal fluid, lymphocytes, urine, tansudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting.

The diagnostic assays of the invention can be nucleic acid assays such as nucleic acid hybridization assays and assays which detect amplification of specific nucleic acid to detect for a nucleic acid sequence of the human p-Hyde described herein.

Target specific probes may be used in the nucleic acid hybridization diagnostic. The probes are specific for or complementary to the target of interest. For precise allelic differentiations, the probes should be about 14 nucleotides long and preferably about 20–30 nucleotides. For more general detection of the human p-Hyde of the invention, nucleic acid probes are about 50 to about 1000 nucleotides, most preferably about 200 to about 400 nucleotides.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction and others) or chemically (e.g by methods such as the phosphoramidite method, or by the triester method).

An alternative means for determining the presence of the human p-Hyde is in situ hybridization, or more recently, in situ polymerase chain reaction. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above described probes are also useful for in-situ hybridization or in order to locate tissues which express this gene, or for other hybridization assays for the presence of this gene or its MRNA in various biological tissues. In-situ hybridization is a sensitive localization method which is not dependent on expression of antigens or native vs. denatured conditions.

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

As used herein, "pharmaceutical composition" could mean therapeutically effective amounts of polypeptide products of the invention together with suitable diluents, preservatives, solubilizers, emulsifiers, adjuvant and/or carriers useful in SCF (stem cell factor) therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermaly, subcutaneously, intraperitonealy, intraventricularly, intracranialy.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed,* 1984, Benjamin/Cummings: Menlo Park, Calif., p. 384). Of a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may, therefore elicit relatively short-lived pharmacological activity. Consequently, frequent administrations of relatively large doses of bioactive compounds may by required to sustain therapeutic efficacy. Compounsd modified by the covalent attachment of water-soluble polymers such as polyethylene glycol, copolymers of polyethylene glycol and polypropylene glycol, carboxymethyl cellulose, dextan, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages

The sufficient amount may include but is not limited to from about 1 µg/kg to about 1000 mg/kg. The amount may be 10 mg/kg. The pharmaceutically acceptable form of the composition includes a pharmaceutically acceptable carrier.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably proven a clinically significant deficit in the activity, function and response of the host.

According to the invention, the component or components of a therapeutic composition of the invention may be introduced parenterally, transmucosally, e.g, orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

According to the present invention, a method is also provided of supplying wild-type p-Hyde function to a cell which carries mutant p-Hyde alleles. Supplying such a function should suppress neoplastic growth of the recipient cells. The wild-type p-Hyde gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant p-Hyde allele, the gene fragment should encode a part of the p-Hyde protein which is required for non-neoplastic growth of the cell. More preferred is the situation where the wild-type p-Hyde gene or a part thereof is introduced into the mutant cell in such a way that it recombines with the endogenous mutant p-Hyde gene present in the cell. Such recombination requires a double recombination event which results in the correction of the p-Hyde gene mutation. Vectors for introduction of genes both for recombination and for extrachromosomal maintenance are known in the art, and any suitable vector may be used. Methods for introducing DNA into cells such as electroporation, calciumphosphate co-precipitation and viral transduction are known in the art, and the choice of method is within the competence of the routineer. Cells transformed with the wild-type p-Hyde gene can be used as model systems to study cancer remission and drug treatments which promote such remission.

As generally discussed above, the p-Hyde gene or fragment, where applicable, may be employed in gene therapy methods in order to increase the amount of the expression products of such genes in cancer cells. Such gene therapy is particularly appropriate for use in both cancerous and pre-cancerous cells, in which the level of p-Hyde polypeptide is absent or diminished compared to normal cells. It may also be useful to increase the level of expression of a given p-Hyde gene even in those rumor cells in which the mutant gene is expressed at a "normal" level, but the gene product is not fully functional.

Gene therapy would be carried out according to generally accepted methods. Cells from a patient's tumor would be first analyzed by the diagnostic methods described above, to ascertain the production of p-Hyde polypeptide in the tumor cells. A virus or plasmid vector (see further details below), containing a copy of the p-Hyde gene linked to expression control elements and capable of replicating inside the rumor cells, is prepared. Suitable vectors are known, such as disclosed in U.S. Pat. No. 5,252,479 and PCT published application WO 93/07282. The vector is then injected into the patient, either locally at the site of the rumor or systemically (in order to reach any rumor cells that may have metastasized to other sites). If the transfected gene is not permanently incorporated into the genome of each of the targeted minor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papavaviruses, e.g., SV40, adenovirus, vaccinia virus, adeno-associated virus, herpesvirus including HSV and EBV and retroviruses of avian, murine, and human origin. Most human gene therapy protocols have been based on disabled murine retroviruses.

Peptides which have p-Hyde activity can be supplied to cells which carry mutant or missing p-Hyde alleles. The sequence of the p-Hyde protein is disclosed (SEQ ID NO:2). Protein can be produced by expression of the cDNA sequence in bacteria, for example, using known expression vectors. Alternatively, p-Hyde polypeptide can be extracted from p-Hyde-producing mammalian cells. In addition, the techniques of synthetic chemistry can be employed to synthesize p-Hyde protein. Any of such techniques can provide the preparation of the present invention which comprises the p-Hyde protein. The preparation is substantially free of other human proteins. This is most readily accomplished by synthesis in a microorganism or in vitro.

P-Hyde molecules can be introduced into cells by microinjection or by use of liposomes, for example. Alternatively, some active molecules may be taken up by cells, actively or by diffusion Extracellular application of the p-Hyde gene product may be sufficient to affect rumor growth. Supply of molecules with p-Hyde activity should lead to partial reversal of the neoplastic state. Other molecules with p-Hyde activity (for example, peptides, drugs or organic compounds) may also be used to effect such a reversal. Modified polypeptides having substantially similar function are also used for peptide therapy.

In another embodiment, the active compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CPC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any a particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

It is contemplated by this invention that p-Hyde replacement therapy could be used similarly in conjunction with chemo- or radiotherapeutic intervention. To induce susceptibility to cell death or to inhibit cell growth or to kill cells, such as malignant or metastatic cells, using the methods and compositions of the present invention, one would contact a "target" cell with the expression vector and at least one DNA damaging agent In oen embodiment the cell is contacted with a single composition or pharmacological formulation that includes both agents, or by contacting the cell with two distinct compositions or formulations, at the same time, wherein one composition includes the vector and the other includes the DNA damaging agent. In another embodiment, treatment with the vector may precede or follow the DNA damaging agent treatment by intervals ranging from minutes to weeks. Protocols and methods are known to those skilled in the art.

DNA damaging agents or factors are known to those skilled in the art and means any chemical compound or treatment method that induces DNA damage when applied to a cell. Such agents and factors include radiation and waves that induce DNA damage such as, gamma-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In another embodiment one may irradiate the localized tumor site with DNA damaging radiation such as X-rays, UV-light, gamma-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with a p-Hyde expression construct, as described above. Agents that directly cross-link nucleic acids, specifically DNA, are envisaged and are shown herein, to eventuate DNA damage leading to a synergistic antineoplastic combination. Agents such as cisplatin and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally. Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasm, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage rages for radioisotopes vary widely, and depend on the half-life of the isotope, the strength and type of radiation emitted, and the uptake by the neoplastic cells.

Several non-viral methods for the transfer of expression constructs into cultured mammalian cells also are contemplated by the preset invention. These include calcium phosphate precipitation DEAE-dextran, direct microinjection, DNA-loaded liposomes and lipofectamine-DNA complexes, cell sonication, gene bombardment using high velocity microprojectiles, and receptor-mediated transfection. Some of these techniques may be successfully adapted for in vivo or ex vivo use. Also, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

In another embodiment, the active compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid).

In yet another embodiment, the therapeutic compound can be delivered in a controlled release system, For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25.351 (1989); Howard et al., J. Neurosurg. 71:105 (1989)). In yet another embodiment a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

As can be readily appreciated by one of ordinary skill in the art, the methods and pharmaceutical compositions of the present invention are particularly suited to administration to a mammal, preferable a human subject.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The present invention provides a kit comprising the all the essential materials and reagents required for inhibiting prostate tumor cell proliferation, transforming prostate cells or detecting prostate cancer cells, may be assembled together in a kit. This generally will comprise selected expression constructs. Also included may be various media for replication of the expression constructs and host cells for such replication. Such kits will comprise distinct containers for each individual reagent. When the components of the kit are provided in one or more liquid solutions, the liquid solution preferably is an aqueous solution, with a sterile aqueous solution being particularly preferred. For in vivo use, the expression construct may be formulated into a pharmaceutically acceptable syringeable composition. In this case, the container means may itself be an inhalent, syringe, pipette, eye dropper, or other such like apparatus, from which the formulation may be applied to an infected area of the body, such as the lungs, injected into an animal, or even applied to and mixed with the other components of the kit. The components of the kit may also be provided in dried or lyophilized forms. When reagents or components are provided as a dried form, reconstitution generally is by the addition of a suitable solvent. It is envisioned that solvent also may be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalent, syringe, pipette, forceps, measured spoon, eye dropper or any such medically approved delivery vehicle.

The following examples are presented in order to more fully illustrate the preferred embodiments of the invention. They should in no way be construed, however, as limiting the broad scope of the invention.

EXPERIMENTAL DETAILS SECTION

EXAMPLE p-Hyde Induces Susceptibility to Induction of Cell Programmed Cell Death in Prostate Cancer Materials and Methods Cell Lines Two rat prostatic cancer cell lines (anaplastic tumor, low metastatic AT-1 and highly metastatic MAT-LyLu) were used for the cDNA competition hybridization strategy. Other Dunning rat prostate cancer cell lines used for Northern analyses were AT-3, MAT-LyLu, MAT-Lu and G. These cell lines were derived from established in-vivo Dunning R3327 rat prostatic tumor sublines and further developed as in-vitro cell lines by Isaacs et al. at Johns Hopkins Oncology Center, Baltimore, Md. (Isaacs et al., 1986). Human prostate cancer cell lines PPC-1, LNCaP, TSU and DU145 used for Northern analyses were obtained from American Tissue Culture Collection, Rockville, Md. All cells were grown in RYMI 1640 medium (Mediate Herndon, Va.) in the presence of 10% fetal calf serum, 50 units of penicillin G and 50 $\mu$g streptomycin sulfate per ml and 250 $\mu$M dexamethasone as previously described (Isaacs et al, 1986).

Cloning Strategy

Radiolabeled MAT-LyLu cDNA population in the presence of vast excess amount of competitor non-radiolabeled AT-1 cDNA population was used to identify cDNAs clones in the MAT-LyLu cDNA library (Rinaldy and Steiner, 1997). One of these cDNAs was novel and designated as p-Hyde. The prostate cancer associated p-Hyde cDNA was further characterized.

Characterization of cDNA

Sequencing p-Hyde cDNA was originally obtained as a λUni ZAP® XR clone, and was further subcloned into pBluescript SK– vector through an vivo excision protocol, as described (Stratagene, La Jolla, Calif.). This double-stranded cDNA was further subjected for Dye Terminator Cycle Sequencing (Perkin Elmer, Foster City, Calif.) using ABI 377 automatic DNA sequencer Version 3.0. The open reading frame of p-Hyde cDNA was determined using the DNA Strider program (Pasteur Institute, Paris).

Northern Blot Analyses

Total RNAs were isolated from cell lines during exponential growth (70% confluence) by using RNAZol B as suggested by the supplier (Tel-Test Inc., Friendswood, Tx.) and subjected to Northern blot analyses. Reverse and forward PCR primer were designed and used to amplify 1.35 kb of the p-Hyde sequence representing the 1467 bases of its open reading frame. The PCR product was radiolabeled by random oligo labeling technique (Multiprime DNA Labeling System, Amersham) and used as a probe for Northern analyses. Relative expression of p-Hyde gene was compared to an internal control (cyclophylin) by scanning of the autoradiogram with a PDI Discovery Series Scanner equipped with Quantity One software.

In vitro Transcription and Translation

The open reading frame of the cDNA was confirmed using in-vitro transcription (capped mRNA) as described followed by in-vitro translation using rabbit reticulocyte lysate (Stratagene, La Jolla, Calif.) in the presence of 75 Ci of L-[$^{35}$S] Methionine (Amersham, Arlington Heights, Ill.). The in vitro translation product was ther identified on 10% SDS polyacrylamide gel electrophoresis by autoradiography.

Subcloning of p-Hyde into pcDNA3.1 (–)

cDNA insert was released from the pBluescript SK⁻ vector through double digests by KpnI and SacI (SK fragment). This fragment represents the intact p-Hyde sequence and was then ligated into dephosphorylated KpnI-SacI double digests of mammalian shuttle vector pcDNA 3.1 (−) (Invitrogen). Ligation mix was used to transfect competent DH5α, selected for ampicillin resistance followed by plasmid preparation using standard cesium chloride density gradient centrifugation. The new conduct of p-Hyde was then used to transfect AT3 rat prostatic cancer sublime by using lipofectamine (Gibco/BRL) followed by G418 selection (Rinaldy et al., 1988). Eight clones were obtained and two of them, AT3-H1 and AT3-H2, were used to assess the function of p-Hyde in its association with apoptosis. In addition, AT3 cell line was also transfected with pcDNA3.1 (−) vector only and its stable transfected cel 1 line, designated as AT3-pc was used as negative control relative to stable transfectant of AT3-H1 and AT3-H2 for the functional assessment of the p-Hyde.

Apoptosis Assay

Apoptosis intensity in AT3 parental cell line was assessed in comparison with AT3-H1, AT3-H2 and AT3-pc as negative control. Two apoptotic agents were employed for this assessment: (1) UV damage of the DNA using UV dosage of 200 J/m2; apoptosis intensity was assayed at 36 h post-UV irradiation and (2) 100 $\mu$M Fluorodeoxyuridine (FUrD) treatment for 36 hours followed by the apoptosis assay. After these apoptotic induction, cells were collected in two fractions: floating and attached cells. Both cell fractions were counted using Neubauer chamber and trypan blue exclusion. DNA were extracted separately from both fractions and analyzed on 1.6% agarose gel electrophoresis to visualize the DNA laddering.

UV-damage Repair Assay

Ultraviolet induced damage in the DNA was assayed using mouse monoclonal antibody specifically cross reacts with cyclobutane pyrimidine dimer (TDM-2) and photoproduct (64M-2). The presence of cyclobutane dimer and 64 photoproducts in DNAs were assessed in microtiter plates (100 and 200 ng/well) using both antibodies separately in a standard ELISA technique. In addition, the UV resistance was also assessed by using UV gradient assay as published (Rinaldy et al, 1988).

Uridine Phosphorylase Assay

Cell extract will be prepared from the cell pellet Before and after the induction with 1 mM 5-dFUrd for 24 hours, the corresponding cell extract will be prepared in 50 mM Potassium Phosphate buffer pH 7.4 through sonication followed by dialysis against the reaction buffer (50 mM potassium phosphate, pH 7.4). The amount of protein will be determined by using standard Lowry or Biorad assay. The same amount of protein from all cell lines will be assayed for UP activity in 50 mM potassium phosphate buffer (pH 7.4) containing 10 mM uridine or thymidine as substrate. After 30 min incubation at 37° C., the reaction will be terminated by adding methanol followed by centrifugation. An aliquot of the supernatant will be run on HPLC column (6×200 mm) of ERC-ODS-1171 (ERMA CR, Inc). The amount of reaction product Uracil or Thymidine can be measured with UV detector at 265 nm compared to the standard. As negative control, the similar reaction mixture will be boiled before the incubation.

Construction of cDNA Libraries

In the first stage, cDNA libraries derived from AT-1 and MAT-LyLu cell lines were generated using Uni ZAP XR vector based on the protocol of Stratagene. The independent clones obtained were 1.9 and 3.4 million clones for MAT-LyLu and AT-1, respectively. These unamplified libraries were subjected to PCR amplification of the cDNA insert population. Reverse primers (RP) and forward primers (FP), downstream and upstream of XhoI and Eco RI cloning site, were used to amplify the cDNA insert population. The distance between both primers in λUni ZAP® or pBluescript was 228 bases.

Design of Competition Probes

Two PCP probes were amplified: radiolabeled MAT-LyLu cDNA population probe and the non-radiolabeled AT-1 cDNA population probe (the cold competitor). The radiolabeled MAT-LyLu PCR product was enriched using S400 Sephacryl spin column. The majority of the unincorporated $^{32}$p-dCTP, primer dimer, and 228 bp of PCR product resulting from the amplification of αDNA without insert was separated from the cDNAs. The purified radiolabeled cDNAs were mixed with 30 fold excess of non-radiolabeled cold competitor AT-1 PCR products and used as a competition-probe to screen the MAT-LyLu cDNA library.

Two kinds of unexpected radiolabeled PCR products that may potentially interfere with the hybridization between the radiolabeled cDNA of the competition probe and the screened cDNA of the library were: 1) the non-exponential amplification of the cDNA and 2) 228 bp PCR product derived from the αDNA without cDNA insert. In order to reduce the possible cross-hybrid on between these two unexpected PCR products with the vector of the screened library, excess amounts of HindIII-digested DNA, PvuII-digested-pBluescript DNA, and the 228 bp PCR product of the pBluescript based on both primers were mixed with the competition probe. Preliminary assessment of this complete mixed competition probe indicated that the hybridization of the MAT-LyLu cDNA library with this probe was extremely weak; whereas the duplicate filter hybridized with the same probe, but without non-radiolabeled AT-1 PCR product, was extremely positive. This clearly indicate that the positive hybridization of the MAT-LyLu products was due to the radiolabeled MAT-LyLu cDNAs of the PCR products which was not competed by the AT-1 cDNAs.

Screening of MAT-LyLu cDNA Libraries

Independent cDNA clones of the unamplified MAT-LyLu phage cDNA library (250,000 clones) were screened with the competition probe as described above. Nineteen enhanced signals were observed; these putative prostate cancer- or metastasis-associated plaques were then rescreened. As the result of this rescreening, 12 individual plaques were purified. The cDNAs were excised and subcloned into plasmid based vectors (pBluescript). This is possible due to the ability of helper phage ExAssist (Stratagene) to excise the cDNA with the pBluescript sequence in circular form as a filamentous phage secreted from the cell. Recombinant pBluescript plasmids were recovered by infecting an F' stain of E. coli (SOLR strain, Stratagene), ampicillin resistant colonies were selected, and the plasmid DNA was extracted. The obtained plasmids were digested with Eco RI and XhoI to identify the cDNA inserts by agarose gel electrophoresis. The results indicated that only four plasmids carried cDNA inserts.

Sequencing of Four Candidate Genes

All four cDNAs were partially sequenced at both the 3' and 5'-ends. These initial sequences were used to search the Genbank nucleic acid database of NCBI for homology or similarities. Three of the cDNAs matched known sequences 1) rat mitochondrial genes coding for 16 s and 12 s rRNAs and tRNAs specific for valine and phenylalanine (Accession #emb/V00680/MIRNR2). 2) rat nucleolar proteins B23.1 mRNA (Accession #gb/J03969/RATB23NP) and 3) rat nucleolar proteins B23.1 and B23.2 (Accession #gb/M37041/RATNUCBA7). The results of this competitive hybridization were consistent with the recognized phenotypic difference between both cell lines. MAT-LyLu exhibits twice the number of both nucleoli and mitochondria (Isaacs et al, 1986). This also suggests that the MAT-LyLu cell line is metabolically more active due to higher gene-dosage or gene-amplification of nucleolar and mitochondrial rRNA and its associated genes.

The Complete Sequence of the Putative Gene, p-Hyde

The fourth cDNA designated as p-Hyde, had an initial sequence, which did not match any known full length sequences in the BLASTN nucleic aid database of the NCBI. Accordingly, p-Hyde cDNA was completely sequenced by using a walk-through sequencing strategy in both directions for three redundancies. Nine contigs from each sequencing direction were obtained and compounded as a full length composite of 2694 bases. The poly(A) tail on the 3'-end and polyadenylation signal sequence of GAGAAA (a slight modification of the conserved AATAAA sequence) located at the position 27 upstream from the poly(A) was also identified. SEQ ID No. 3 sets forth the resulting nucleic acid sequence of the rat p-Hyde and the resulting amino acid sequences of the rat p-Hyde.

Generation of PCR Probe Representing Open Reading Frame p-Hyde Gene

FIG. 8B shows the PCR amplification of the cDNA insert was conducted using three sets of sequencing primers. PCR product based on primer 11 and 5 represents the open reading frame of the p-Hyde cDNA. It was further radiolabeled by Random-Oligo-Labeling technique and used as a representative probe for the cDNA insert in Northern analysis.

Northern Blot Analysis of p-Hyde

Some of the rat prostate cancer sublines (AT-1, MAT-LyLu, MAT-Lu, AT-3 and G) and human prostate cancer cell line (PPC, LNCaP, DU145 and TSU) were assessed by Northern blot analysis using PCR radiolabeled probe. The result indicated that the transcript of the human counterpart was slightly smaller relative to the rat p-Hyde mRNA. The same blot was further hybridized with cyclophylin cDNA as internal control. In this autoradiogram, 28S and 18S ribosomal RNA were used as marker. The length of the transcript was calculated based on the Spirin's formula $M=1550 \times S^{2.1}$ where M=molecular weight and S=Svedberg's constant (McConkey, 1967). Signals of the p-Hyde and cyclophylin transcripts were quantitated and normalized using a computerized densitometer (Quantity-One software, PDI). The levels of p-Hyde mRNA expression from both rat and human prostate cancer cell lines were compared. This data indicated that there was differential expression of p-Hyde gene in both Dunning rat and human prostate cancer cell lines which suggests that there may be a functional correlation between p-Hyde expression and prostate cancer progression. MAT-Lu showed the highest level of transcription, whereas AT-3 had the lowest. These data also indicated that the level of transcription in MAT-LyLu was relatively higher than that of AT-1 suggesting that the novel cDNA was the result of cDNA competition between MAT-LyLu and AT-1 cDNAs. More importantly, the human homologue of p-Hyde does exist as demonstrated in the human prostate cancer cell lines. The highest level of p-Hyde transcription occurred in PPC-1, whereas the lowest was in the LNCaP cell line.

Analysis of the Deduced Amino Acid Sequence of p-Hyde Derived from ORF

Open reading of the cDNA consists of 1467 bases coding for 489 no acid residues; the calculated molecular weight of this protein is 54.8 kD. Further molecular analyses of this deduced amino acid sequence is based on the Kyte-Doolittle hydrophilicity plot, James-Wolf antigenic index and Emini surface probability plot using Laser Gene DNAstar software. In addition, hydrophilicity profile of the deduced amino acid sequence was deduced based on Hopp and Woods using Antigen program for the prediction of its antigenic determinants (Table II). The results of the first three analyses were in agreement with the fourth one. Two peptide regions (residues 113 through 131 and residues 223 through 249) exhibited the highest points of hydrophilicity and the antigenic index. Both peptide sequences can be used as immunogenic peptide to generate antibody. Its application to detect the translation product of p-Hyde in Western analysis was in agreement with the highest score of its surface probability.

TABLE I

| Average Hydrophilicity | Amino-Acid Sequence |
| --- | --- |
| 2.53 | 241 to 246 |
| 1.93 | 117 to 122 |
| 1.73 | 119 to 124 |

Confirmation of the ORF by in vitro Transcription and Translation

To confirm the reading frame based on the sequencing data, the p-Hyde cDNA which is constructed in pBluescript was digested with KpnI rendering the linearized construct to be accessible for T3-RNA polymerase. This enzyme directs the synthesis of the riboprobe with 5'cap structure (5'me7Gppp5'G analog) similar to those present in eukaryotic mRNA (Stratagene). The 5'cap is important to increase the yield and the stability of the synthesized mRNA as well as to enhance the in-vitro translation efficiency of the mRNA. This capped mRNA was then used as a template for in-vitro translation using rabbit reticulocyte lysates (Stratagene) in the presence of $^{35}$S-Methionine. The translation products were identified under denaturing conditions using polyacrylamide gel electrophoresis containing 8 M urea. The autoradiograph shown in FIG. 14 revealed that two translation products (55 and 55.5 kDa protein) were observed.

Molecular weights of these two proteins are in agreement with the calculated molecular weight of the deduced amino acid sequence of the reading frame. In addition, two start codons were also identified in this reading frame correlating with the two translation products obtained through in vitro translation of the riboprobe. The difference in molecular weight between both translation products is in agreement with the difference in 4 amino acid residues (MSGE) on the C terminal between both start codons. The molecular weight difference between both translation products is in agreement with the 0.5 kDa molecular weight of MSGE.

Subcloning of p-Hyde Insert into pCDNA 3.1 (−) and transfection into Rat and Human Prostate Cancer Cell Lines Referring to the data of differential expression of p-Hyde in rat and human prostate cancer cell lines, it is tempting to integrate this gene into cell line expressing the lowest level of p-Hyde followed by the assessment of the function of this gene in its stable transfectants. For this purpose, p-Hyde cDNA was subcloned into pcDNA3.1 (−) mammalian expression vector (Invitrogen). The following features of pcDNA3.1 facilitate both subcloning and gene expression: (1) An extensive multiple cloning site to facilitate cloning in one direction. (2) A CMV promoter to drive the constitutive transcription and translation of the inserted p-Hyde cDNA, and (3) An SV40 splice acceptor linked to a SV40 polyadenylation signal to facilitate expression. The KpnI-XbaI fragment of the p-Hyde cDNA containing an intact open reading frame was successfully subcloned into pcDNA3.1 (−) vector. The CsCl-banding-purified-pcDNA containing HYDE insert (designated as pcHYDE) was then transfected into rat (AT-1 and AT-3) and human (DU145 and PPC-1) prostate cancer cell line using Lipofectamine (Gibco/BRL) under G418 selection. In addition to this pcHYDE, all cell lines were also successfully transfected with the pcDNA3.1(−) vector as negative control. The results of obtaining the stable transfectants indicated that pcHYDE gene product is not toxic to the host cell.

In vitro Assessment of Stable p-Hyde Transfectants

The function of pcHYDE in stable transfectants (AT1 and AT3 group) listed were assessed in vitro in association with the cell cycle and apoptosis. The objective for the apoptosis assessment is based on the hypothesis that p-Hyde is a rat homologue of the murine putative TSAP-6 gene which is associated with the upregulation of apoptosis response under the induction of tumor suppressor p53 (Amson et al., 1996). Whereas the cell cycle analysis is referred to the fact that MAT-LyLu cell line is highly metastatic and the level of p-Hyde expression in this cell line is relatively higher an AT-1 cell line.

Cell Cycle Analysis

The strategy of the cell cycle analysis is based on the arrest of cell population in G1 and S boundary after 24 hours treatment with 1 mM Hydroxyurea (Iwasaka et al., 1995). As a result, the G2 phase should be zero. Cells were harvested after hydroxyurea release at 0, 10 and 24 hours and subjected to flowcytometer analysis using standard propidium iodide staining. The result is shown in TABLE III and showed that both AT1-H1 and AT3-H1, at 10 hours after the release of Hydroxyurea, were relatively slow in entering the S-phase, whereas the parental cell line (AT1 and AT3) were faster. At 24 hours aft the release, the G2 cells were all elevated indicating that cell cycle was in progress. Overall, the slow enhance into S phase in both pcHYDE stable transfectants does not corroborate directly that it is correlated with the slower tumor growth in vivo. The progress of re-entering the cell cycle at 0, 10 and 24 hours after the release of Hydroxyurea were followed by flowcytometer. Consistently, no G2 phase was detected at $t_0$—after 24 hours treatment with Hydroxyurea—demonstrating the cell cycle arrest in the G1 and S boundary.

Overall, the arrest of all cell cultures in G1 and S boundary by 1 mM Hydroxyurea treatment for 24 hours was confirmed referring to the 0% population of G2. Those results demonstarte that the slower response in entering the S phase in AT1-H1 and AT3-H1 is likely due to the effect of the pcHYDE gene product that may reflect the growth characteristic of these stable transfectants in vivo.

Induction of Susceptibility to Apoptosis

Apoptotic response was assessed using DNA laddering assay. DNAs were extracted after the respective treatment (24 hours with 1 mM Hydroxyurea followed by 24 hours with 0.1 mM 5'-dFUrd) and analyzed on 1.6% agarose gel electrophoresis. In agreement with cell cycle analyses, apoptotic response of the stable transfectants AT1-H1 and AT3-H1 (pcHYDE transfected AT-1 and AT-3) are consistently and significantly higher relative to both parental (AT-1 and AT-3) and pcDNA-transfected parental cell lines (AT1-pcl and AT3-pcl). In particular, the highest apoptotic response occurred in synchronized culture under the induction with 0.1 mM 5'-dFUrd.

The enhanced apoptotic response in AT1-H1 and AT3-H1 transfectant after hydroxyurea treatment is the result of "thymineless death" (Kyprianou, 1994, Kyprianou et al., 1994) leading to depletion of intracellular thymidine-5-triphosphate (TTP) pools through indirect inhibition of thymidylate synthetase by fluorodeoxyuridine. Taken together, these data demonstrate that the apoptotic response in the pcHYDE stable transfectants is due to the downstream effect of pcHYDE gene product.

UV-damaged DNA Cannot be Repaired in Prostate Cells Transfected with pHyde

Three DNA enzyme repair systems were evaluated in parental compared to p-Hyde transfected cells: uridine phosphorylase, uridine kinase, and UV damage repair. UV damage repair was impaired in the the transfected cells. Decreased DNA repair activity results in higher levels of intact photoproducts (64PP). Consistent with these data, pHyde transfected cells also had a significant reduction in survival following UV exposure compared to parental AT3 cells as determined by colony formation assay. Thus, DNA repair enzyme impairment correlated with shorter survival and induction of apoptosis in prostate cancer cells transfected with p-Hyde.

Northern RNA Analysis of p-Hyde Confirms Overexpression of p-Hyde

To confirm the correlation between apoptotic response and p-Hyde on the transcription level, Northern analysis of the total RNA derived from AT3-H1, AT3-H2 relative to AT3 parental cell line was performed. The result clearly demonstrated that the transcription level of pcHYDE in stable transfectant of AT3-H1 and AT3-H2 were significantly higher relative to AT3 parental cell line. This Northern analysis was carried out only in AT3, AT3-H1 and AT3-H2 using Hyde PCR product and internal control cyclophilin as a probe.

p-Hyde Suppresses Prostate Cancer Growth

The lowest level of p-Hyde expression was observed in AT3 cell line. For this reason, AT3 cell line was transfected with pcHYDE, a Construct of p-Hyde in mammalian expression vector of pcDNA3.1(−) under G418 selections. As negative control, AT-3 cell line was also transfected with the vector only and the stable transfectants obtained was designated as AT3-pc.

The tumor growth of the parental cell line of AT-3 and in stable transfectant AT3-H1 and AT3-H2 have been evaluated in vivo. One million cells of each cell lines in 0.3 ml of Hanks solution were inoculated subcutaneously in each flank of inbred male Copenhagen rat. In this initial experiment, three groups of each five rats were injected with each cell line. The size of tumors were scored after a time schedule. These results indicated that both AT3-H1 and AT3-H2 stable transfectant grew significantly slower than the AT-3 parental cell line suggesting that the tumor growth regression in both stable transfectants are regulated by the pcHYDE gene product.

Tumor progression represents an accumulation of genetic changes that affect oncogene and tumor suppressor gene expression, thereby altering the responsiveness of the cell to autocrine and paracrine positive and negative growth regulators. The Dunning tumor rat model of prostate cancer tumor progression consists of a spectrum of prostate cancer phenotypes ranging from well differentiated to poorly differentiated with differing responses to androgens. Moreover, the sublines originated and evolved from the same original spontaneous rat prostate tumor, thus making this present study of tumor progression unique. The development of these cell lines as the results of progression of tumor within a single and multiple serial passage.

The screening strategy of competition hybridization of cDNA library generated from highly metastatic rat MAT- LyLu cell line resulted in a novel cDNA clone designated as p-Hyde (Rinaldy and Steiner, 1997). The full length of this cDNA, indicated as its restriction map, consists of 2713 nucleic acid residues; it contains two reading frames consisting of 1467 and 1452 residues, respectively. Forty six percent of the sequence is the untranslated region and majority of this is in the 3' end of the gene. The nucleic acid sequence of the rat p-Hyde is set forth in SEQ ID NO 3 and the nucleic acid sequence of the human p-Hyde is set forth in SEQ ID NO 1.

The level of expression of p-Hyde was determined by Northern blot analyses in both rat and human prostate cancer cell lines and compared to the cyclophylin expression as internal control. The Dunning rat prostatic cancer cell lines AT-1, MAT-LyLu, MAT-Lu, AT-3 and G, and human prostate cancer cell lines PPC1, LNCap, TSU and DU145 all expressed p-Hyde, albeit at different levels. The transcript size of the human counterpart is slightly smaller relative to the rat p-Hyde mRNA. The data also indicated that there is a differential expression of p-Hyde gene in both rat and human prostatic cancer cell lines suggesting that there may be a functional correlation between p-Hyde expression and prostate cancer progression. MAT-Lu showed the highest level of transcription, whereas AT-3 had the lowest. The striking difference between these two cell lines is important in its association with the growth characteristic of MAT-Lu cell line which is highly metastatic. These data also indicated that the level of transcription in MAT-LyLu was relatively (10%) higher than that of AT-1, demonstrating that the novel cDNA was the result of cDNA competition between MAT-LyLu and AT-1 cDNAs (Rinaldy and Steiner, 1997). Of significance, the human homologue of p-Hyde does exist in the human prostate cancer cell lines. The highest level of p-Hyde transcription occurred in PPC1, a primary androgen sensitive human prostate cancer cell line, whereas it was lowest in LNCaP cell line, an androgen-insensitive prostate cancer cell line. Thus, p-Hyde does not appear to be specific to mammalian prostate tissue, but has been found in other tissues including placenta and breast and in other species such as mouse and human suggesting that its role is important in fundamental cellular biology.

Tumor Suppression and Induction of Susceptibility to Apoptosis

Interestingly, p-Hyde has the dual ability to act like a tumor suppressor gene and induce susceptibility to apoptosis by what may be p53 independent pathways. The growth of prostate tumors in rats was greatly inhibited by p-Hyde. Moreover, prostate cancer cells expressing p-Hyde were more sensitive to UV DNA damage driving these cells into cell programmed death. Analysis of DNA repair enzyme activity suggests a defect resulting in the presence of intact (6-4) PP and decreased cell survival by colony forming assay. However, the capacity of p-Hyde to induce susceptibility to apoptosis is not limited to UV DNA damage. Chemotherapy agent, Fluorodeoxyuridine, a pyrimidine antimetabolite which is related to fluorouracil (5-FU) and has been used for treatment of a wide variety of human epithelial malignancies, also more readily induces apoptosis in prostate cancer cell expressing p-Hyde. Moreover, cancer cells expressing p-Hyde are also more susceptible to gamma radiation. Thus, the mechanisms of cellular DNA injury are different for UV, gamma radiation, and Fluorodeoxyuridine suggesting that the ability to make cells more susceptible to apoptosis is more global in action. This unique function of p-Hyde represents a new class genes that induce susceptibility to apoptosis. This is different than the function ascribed to tumor suppressor genes like p53 which directly induces apoptosis, not sensitivity to apoptosis (Yonish-Rouach et al., 1991). Moreover, p-Hyde activity is in contrast to bcl-2 where the absence of bcl-2, not the presence of, makes the cancer cell more susceptible to cell programmed death (McDonnell et al., 1992).

Use in Therapy of Human Disease

These unique functional features of the p-Hyde gene may be exploited for the treatment of hyperproliferative disorders and cancer. One effective therapeutic strategy, for example, may be the treatment of carcinoma cells express p-Hyde with chemotherapy agents or UV mimetic drugs (such as acetylaminofluorine). However, cancer cells are not likely to produce significant levels of the growth inhibition p-Hyde. Consequently, the p-Hyde gene my be introduced into cancer cells by gene therapy. Tumors transduced with vectors containing p-Hyde may not only be directly suppressed by p-Hyde as demonstrated in this study, but also when treated in combination with DNA damaging therapy such as chemotherapy, UV mimetic drugs, or radiation, have even a greater anti-cancer effect. Since gene therapy will target cancer cells, the enhancement of apoptosis will occur more selectively in cancer cells following DNA damage (UV, radiation, or chemotherapy).

EXAMPLE 2

Prostate Cancer Gene Therapy Using Adenovirus Expressing a Novel Tumor Suppressor Gene pHyde Materials and Methods Cell Lines and Tissue Culture Condition Human prostate cancer cell (obtained from ATCC, Rockville, Md.) PFC-1, DU145, PC-3, LNCaP, and TSU-Pr1 were grown in RPMI-1640 medium (Cellgro, Heredon, Va.) containing 10% fetal bovine serum (Hyclone Laboratories, Logan, Utah) at 37° C. and 5% $CO_2$. Human embryonic kidney cell line 293 (ATCC) was grown in D-MEM medium (Cellgro) containing 10% heat inactivated fetal bovine serum at 37° C. and 5% $CO_2$.

Construction of AdRSVpHyde

A rat p-Hyde cDNA gene was isolatd as described in U.S Ser. No.: 09/302,457. After digestion with EcoR I, a 2.6 kb fragment which contains the 1467 bp full-length coding sequence of p-Hyde cDNA was subcloned under the control of a truncated RSV promoter (395 bp) into an E1/E3 deleted adenoviral shuttle vector. The resultant adenoviral shuttle vector was cotransfected into 293 cells with pYM17, an adenoviral type 5 genome plasmid, by calcium phosphate method. Individual plaques were screened for recombinant AdRSVpHyde by PCR using specific primers for both the RSV promoter and pHyde cDNA sequences. Single viral clones were propagated in 293 cells. The culture medium of the 293 cells showing the completed cytopathic effect (CPE) was collected and the adenovirus was purified and concentrated by twice CsCl2 gradient ultracentrifugation. The viral titration and transduction were performed as previously described. The schematic diagram of AdRSVp-Hyde was illustrated in FIG. 1. The sequence of AdRSVp-Hyde is set forth in FIG. 10.

Northern Blot

Cells were extracted and total RNA was isolated by RNeasy Kit (Qiagen, Santa Clarita, Calif.). Total RNA was loaded on a 1.2% polyacrylamide gel and processed to electrophoresis. The standard Northern blot transfer to a Nylon membrane (Hybond-N+, Amersham Life Science, Buckinghamshire, England) was performed as previously described. The cDNA probes (pHyde or p53) were labeled by a-$^{32}$P-dCTP using random primer method (Prime-It II Kit, Stratagene, La Jolla, Calif.). The membrane was hybridized with the probe in Rapid-hyb buffer (Amersham Life Science) according to the Manufacturer's protocol. The membrane was exposed to a Kodak X-ray film under one intensifying screens at −80° C. for autoradiography. GAPDH cDNA probe was labeled as described above and used as an internal control for normalization.

Western Blot

Cells were extracted and processed for gel electrophoresis as previously described.(Lu Y, Whitaker L, Li X, et al, Coexpression of galectin-1 and its complementary glycoconjugates laminin and lysosome-associated membrane proteins in murine PCC4.aza1R embryonal carcinoma cells induced to differentiation by butyrate. *Mol Cell Differ.* 1995;3:175–191). Cell extract lysates (100 mg) were loaded on 12% polyacrylamide gels and subjected to sodium dodecylsulfate (SDS) gel electrophoresis, then transferred to a nitrocellulose membrane (Bio-Rad Laboratories, Hercules, Calif.). The membrane was treated with blocking solution (15% nonfat milk, 0.02% sodium azide in Phosphate-buffered saline) overnight at 4° C. The membrane was incubated for 1 hr at room temperature with rabbit anti-rat pHyde polyclonal antibody (specifically generated by Research Genetics, Inc. based on the computer-created antigenic peptide derived from pHyde coding sequences). The membrane was then incubated for 1 hr at room temperature with $^{125}$I-labeled second antibody (Amersham Life Science, Arlington Heights, Ill.). The membrane was exposed to a Kodak X-ray film between two intensifying screen at −80° C. for autoradiography.

AdRSVpHyde in vitro Studies

Human prostate cancer cells were infected with AdRSVpHyde in vitro with a multiplicity of infection (MOI) of 100 or 200. After viral infection, cells were incubated at 37° C. and cell numbers were determined at day 5 after viral infection.

In vivo Studies Using DU145 Xenograft Tumors

DU145 cells ($1.4 \times 10^7$ cells in 0.2 ml of PBS) were injected subcutaneously into the flank of male nude mice (Harlan Sprague Dawley). When the tumors reached an average volume of 80 mm$^3$, $5 \times 10^9$ pfu adenoviral vectors (AdRSVpHyde or control adenovirus AdRSVlacZ) or PBS alone for untreated controls were injected directly into the tumor. Tumor volume was measured every three to four days until the animals were euthanized. All the animals were sacrificed at day 52 after viral injection when several of them showed distress or had a tumor burden greater than 15% of total body weight. Tumor samples were collected and processed for H&E staining.

DNA Extraction and Gel Electrophoretic Analysis of DNA Fragmentation

Soluable DNA was extracted as described previously (in Oridate N, Lotan D, Xu X-C, Hong W K, and Lotan R. Differentiation induction of apoptosis by all-trans-retinoic acid and N-(4-hydroxyphenyl)retinamide in human head and neck squamous cell carcinoma cell lines. *Clin. Cancer Res.* 1996;2:855–863) Briefly, the cells floating in medium were collected 48 h post transduction by centrifugation. The pellet was resuspended in Tris-EDTA buffer (pH 8.0). The cells were lysed in 10 mM Tr-s-HCl (pH 8.0), 10 mM EDTA, and 0.5% Triton X-100 on ice for 15 min. The lysate was centrifuged at 12,000×g for 15 min to separate soluble (fragmented) DNA from pellet (intact genomic) DNA. Soluble DNA was treated with Rnase A (50 ug/ml) at 37 C for 1 h, followed by treatment with proteinase K (100 ug/ml) in 0.5% SDS, at 50 C for 2 h. The residual material was extracted with phenol/chloroform, precipitated in ethanol, electrophoresed on a 2% agarose gel.

Results

Exogenous p-Hyde Expression in DU145 Cells

Figure 2A:
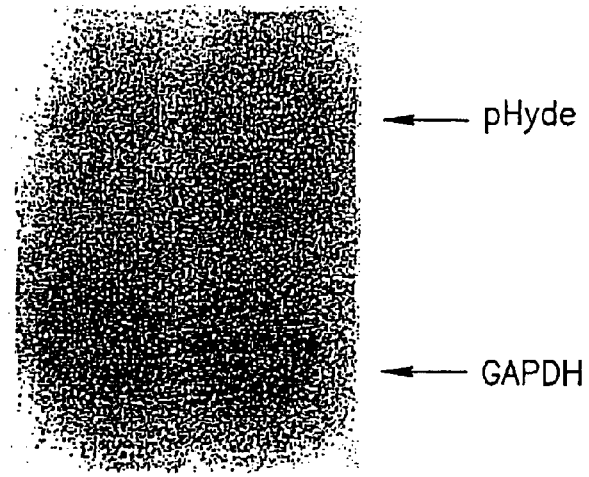
FIGS. 2A and 2B. Expression of pHyde by AdRSV-pHyde. DU145 cells transduced by AdRSVpHyde at MOI=200 were harvested in 48 h post infection for either mRNA or protein extraction. (A) Expression of p-Hyde at mRNA level in DU145 cells. Sample wells were each loaded with 10 mg of total RNA, electrophoresed in 12.5% agarose gel, transferred to nylon membrane, and hybridized with $^{32}$P-labeled pHyde cDNA. Northern blot was stripped and rehybridized with GAPDH to assess gel loading. (B) Expression of pHyde at protein level in DU145 cells. Protein extracts (50 mg) were loaded on a 12% SDS-PAGE gel. Rabbit anti-rat pHyde antibody was used as the primary antibody.
Figure 2B:
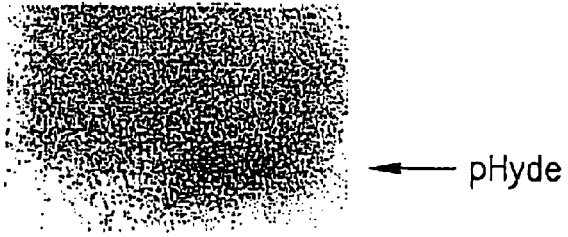

To determine whether AdRSVpHyde is able to successfully transfer and express rat pHyde at mRNA and protein levels, DU145 cells were transduced by AdRSVpHyde at MOI=200. The cell extract were harvested 48 h after viral transduction to determine the p-Hyde expression. While there was a minor endogenous expression of pHyde at mRNA level (FIG. 2A) but not at protein level (FIG. 2B) in DU145 cells, there was an apparent high exogenous p-Hyde expression induced by AdRSVpHyde at both mRNA (FIG. 2A) and protein (FIG. 2B) levels.

Prostate Cancer Cell Growth Inhibited by AdRSVHyde

Figure 3A:
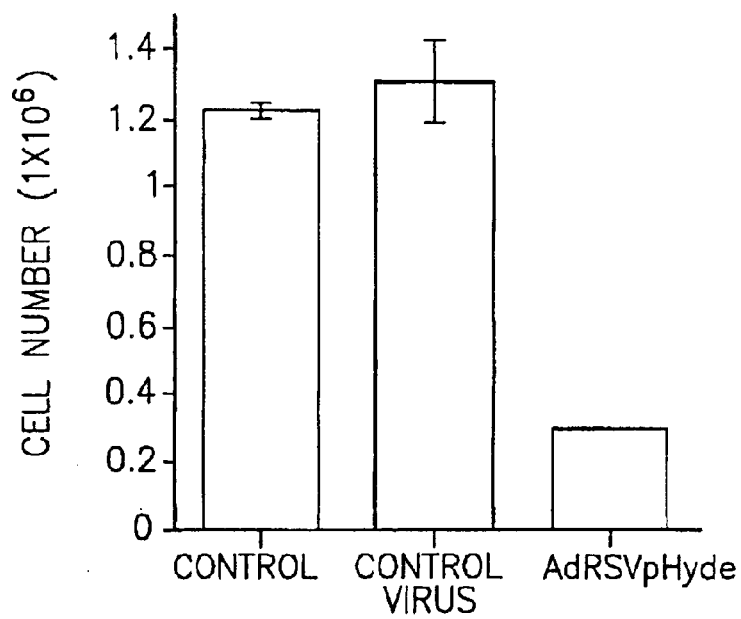
FIGS. 3A and 3B. Inhibitory effects of p-Hyde on prostate cancer cell growth. DU145 (A) and LNCAP (B) cells were transduced with or without adenoviral vectors at MOI=100. Cell numbers were counted at day 5 after viral transduction. The data represent the results from two independent experiments with each in duplicates.
Figure 3B:
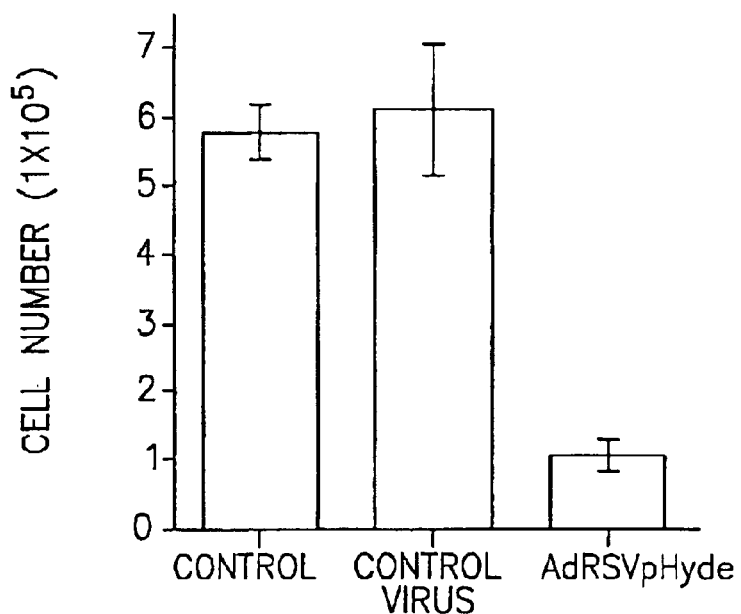

To determine the effects of p-Hyde on cell growth of human prostate cancer cell lines, DU145 and LNCaP were treated with AdRSVpHyde, AdRSVlacZ (control vector), and no virus in vitro. AdRSVpHyde significantly inhibited the growth of DU145 and LNCaP cells, with 76.9% (FIG. 3A) and 83.1% (FIG. 3B) inhibition respectively, compared to untreated control cells.

AdRSVpHyde Inhibited Prostate Tumor Growth in vivo

Figure 4:
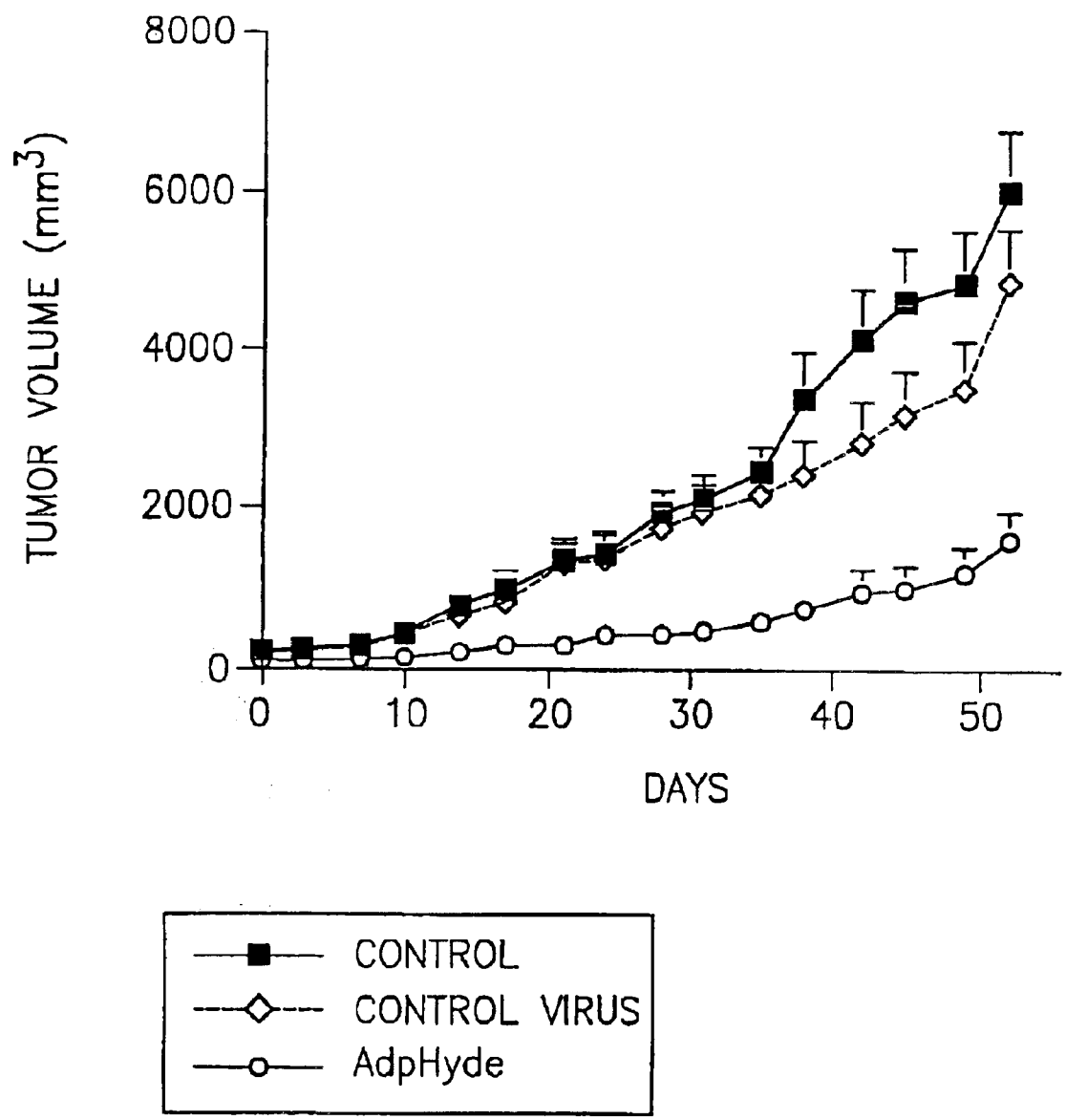
FIG. 4. AdRSVpHyde inhibits prostate tumor growth in vivo. DU145 cells ($1.4 \times 10^7$ cells) were injected subcutaneously into the flanks of nude nice. When tumors reached an average volume of 80 mm$^3$ (about one month after tumor cell inoculation), tumors were untreated (control), or in intratumorally injected (day 0) either by $3 \times 10^9$ pfu control virus AdRSVlacZ (control virus), or $5 \times 10^9$ pfu AdRSVp-Hyde (AdRSVpHyde). The tumor sizes were periodically measured at tomes shown in the figure up to day 52 days post viral injection FIGS. 5A-5F. Morphological changes of DU145 and LNCaP cells transduced by AdRSVpHyde. Cells were transduced by control adenovirus AdRSVlacZ or by AdRSVp-Hyde at MOI=100. The morphologic features of untreated control cells and viral-transduced cells were recorded at day 5 post viral transduction. All the photos are at the same magnification (66×). (A) and (D): Untasted control cells; (B) and (E): Viral control AdRSVlacZ treated cells; (C) and (F): AdRSVpHyde treated cells.

To evaluate the effects of AdRSVpHyde treatment of prostate cancer cell growth in vivo, DU145 human prostate tumors were established in nude mice by injecting $1.4 \times 10^7$ PPC-1 cells subcutaneously into the flanks of nude mice. When mice developed tumors with an averaging 80 mm$^3$ volume, the mice were divided into three groups: AdRSVpHyde treated (n=7), AdRSVlacZ control virus treated (n=7), and untreated groups (n=7). Treated tumors were injected with a single dose of $5 \times 10^9$ pfu of either the control virus or AdRSVpHyde. As shown in FIG. 4, untreated and control virus treated DU145 tumors grew rapidly relative to the AdRSVpHyde treated tumors. By day 53 following viral injection, the tumor burden in nude mice bearing untreated and control virus treated DU145 tumors reached 5953 mm$^3$ and 4777 mm$^3$ respectively. In contrast, DU145 tumors transduced by AdRSVpHyde had a significant reduction in tumor volume (1515 mm$^3$) compared to untreated and control virus treated-DU145 tumors, that is, 25.4% of untreated and 31.7% of control virus treated DU145 tumor volume (FIG. 4).

Figure 6:
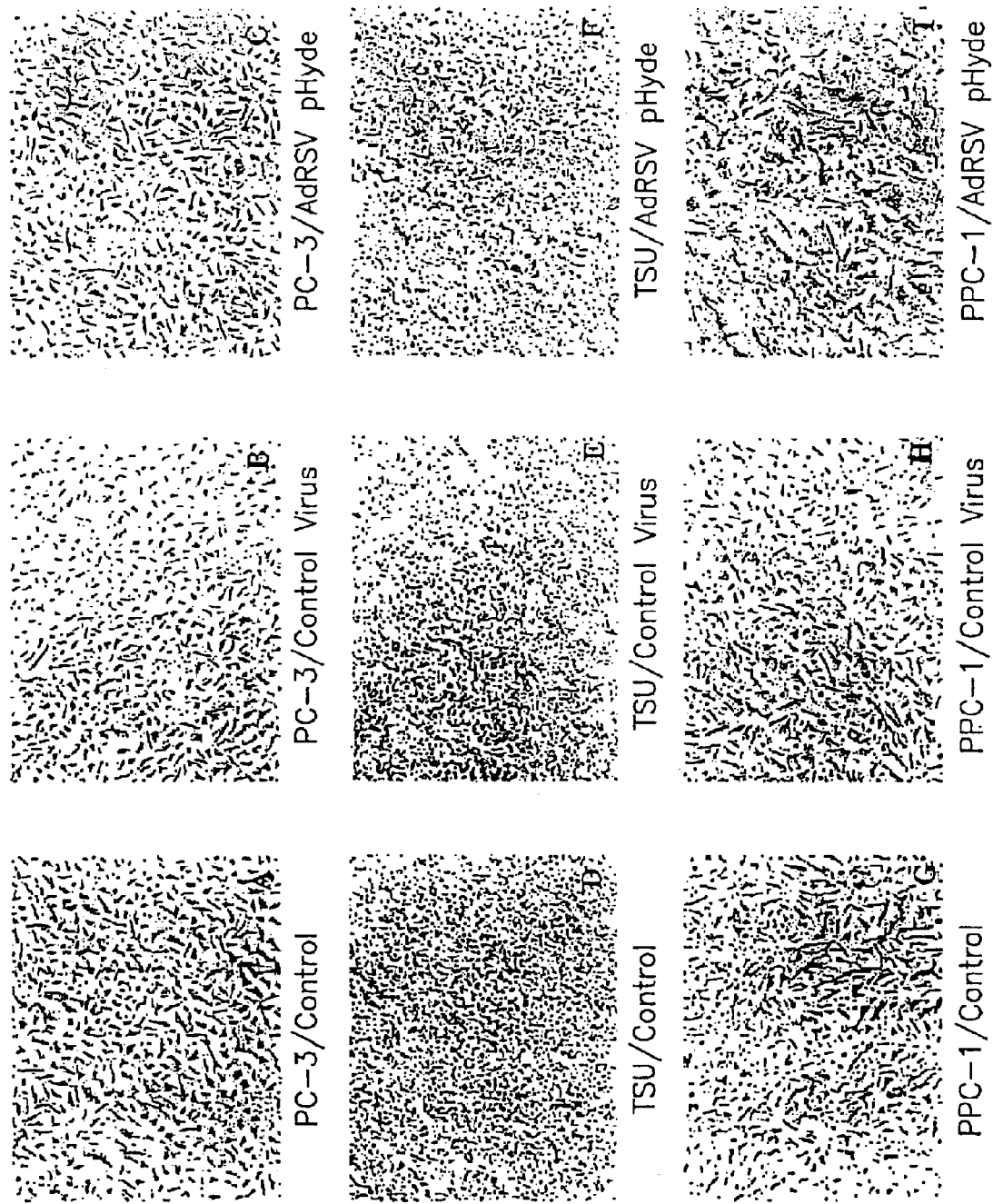
FIGS. 6A-6I. Morphological changes of PC-3, TSU, and PPC-1 cells transduced by AdRSVpHyde. Cells transduced by control adenovirus AdRSVlacZ or by AdRSVpHyde at MOI=100. The morphologic features of untreated control cells and viral-transduced cells were recorded at day 5 post viral transduction. All the photos are at the same magnification (66×). (A, D, G): Untreated control cells; (B, E, H): Viral control AdRSVlacZ treated cells; (C, F, I): AdRSV-pHyde treated cells.
Figure 7:
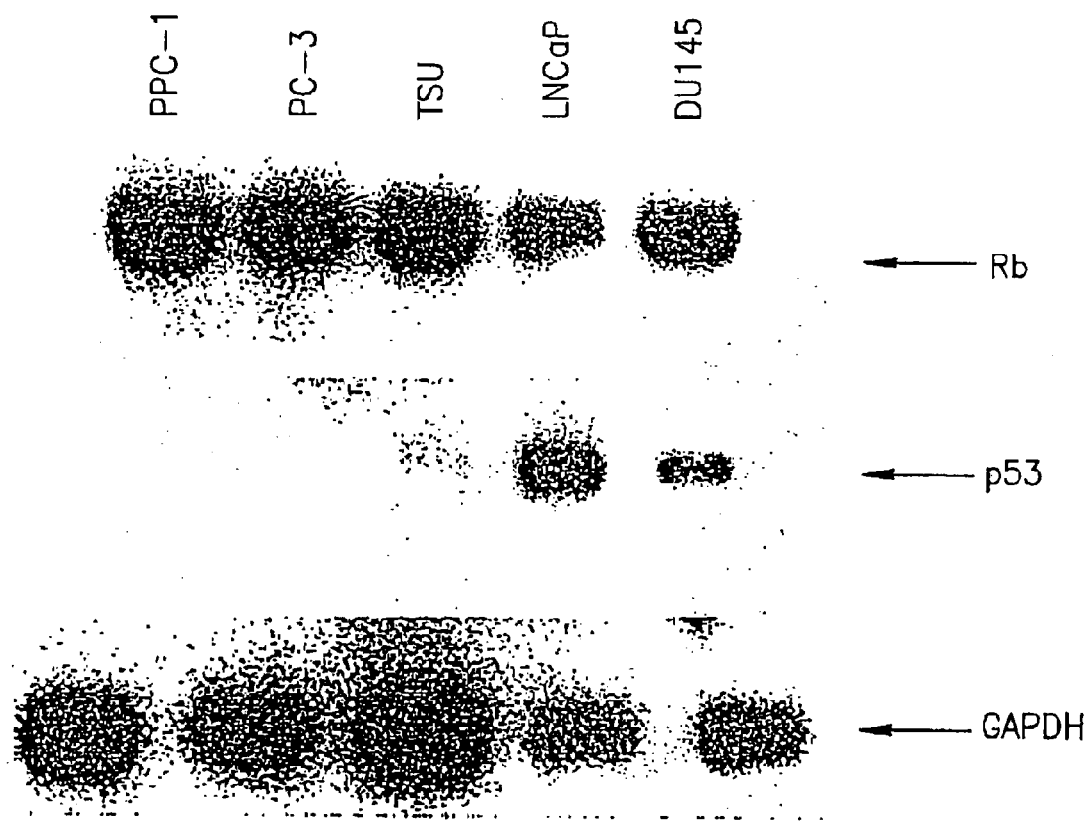
FIG. 7. Expression of p53 and Rb mRNA in various prostate cancer cell lines. Sample wells were each loaded with 10 mg of total RNA, electrophoresed in 12.5% agarose gel, transferred to nylon membrane, and hybridized with $^{32}$P-labeled p53 or Rb cDNA probe. Northern blot was stripped and rehybridized with GAPDH to normalize the gel loading.

Growth Inhibition by AdRSVpHyde Correlated to p53 Expression in Prostate Cancer Cells One observation in the in vitro study was that the phenotype of DU145 and LNCaP cells transduced by AdRSVpHyde were also altered. Unlike the control and control virus treated cells, AdRSVpHyde-transduced cells had a marked morphology of round, detaching and floated dying cells, a characteristic of cells undergoing apoptosis, and cell number decreased quickly over time (FIG. 5). Consistently, AdRSVpHyde showed a strong inhibition on the growth of these two cell lines (FIG. 3). However, AdRSVpHyde did not inhibit the cellular growth of PC-3 and TSU-Pr cells, and had only a minor growth inhibition on PPC-1 cells (data not shown). Consistently, there was no evident morphological differences between untreated control, control virus-treated and AdRSVpHyde-treated cells in these lines (FIG. 6). To determine whether the differential expression of various genes, especially those involved in apoptosis pathway, accounted for the differential inhibitory effect by AdRSVpHyde on different prostate cancer cell lines, several genes including p53 and Rb were screened at mRNA level by Northern hybridization. Interestingly but not too surprisingly, p53 was found to only express in DU145 and LNCaP cells but not in PC-3, TSU-Pr, and PPC-1 cells; in contrast, Rb gene were all expressed at the mRNA level in these cells (FIG. 7).

Figure 8:
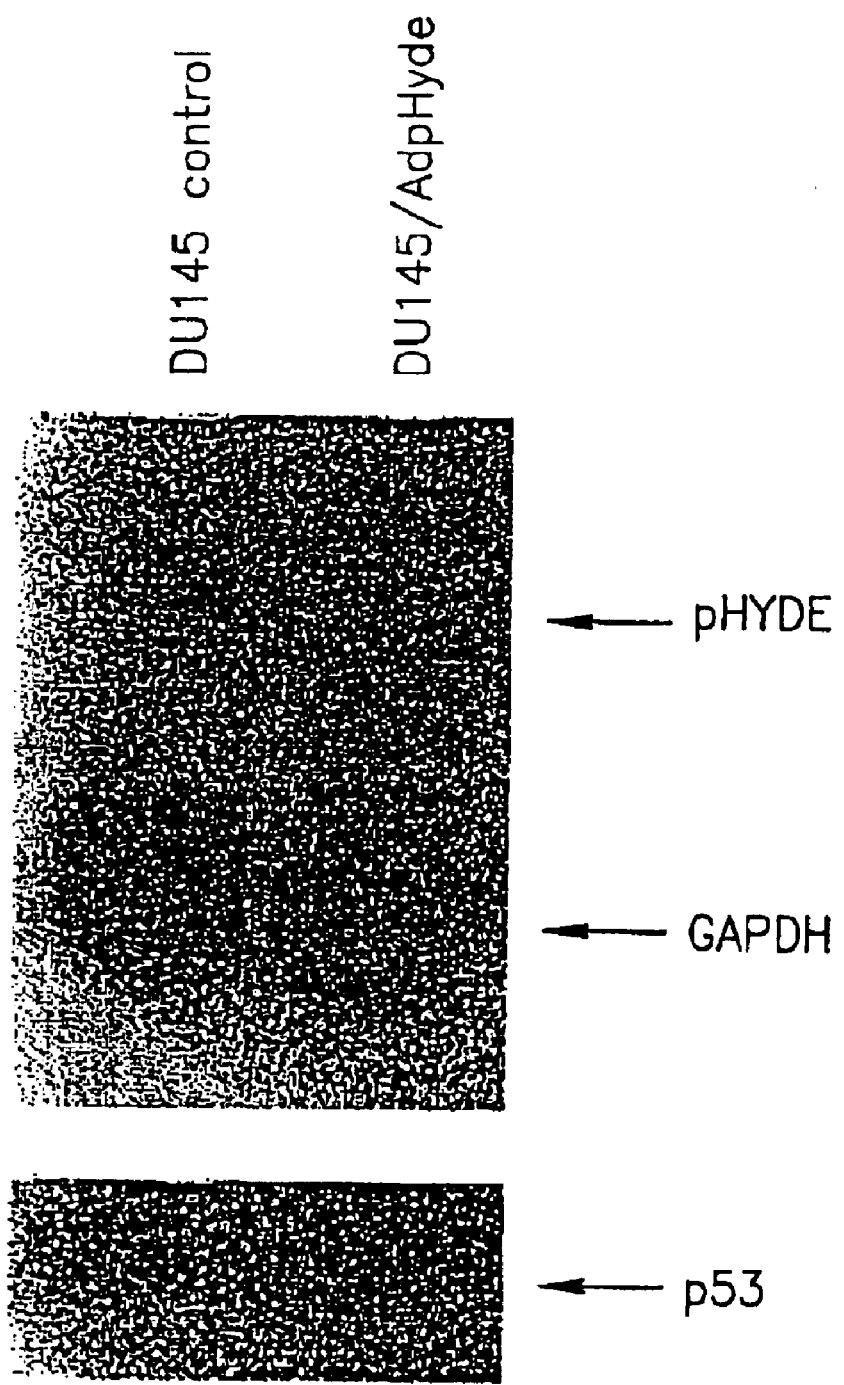
FIG. 8. The p-Hyde open reading frame. The PCR amplified product of the p-Hyde cDNA using Primer set 11-3 (lane 2) 12-4 (lane 3) and 11-5 (lane 4). 1 Hind III (lane 1) and pX174 Hind III (lane 7) were used as markers (A). AdRS-VpHyde induced p53 expression in DU145 Cells. The same Northern blot in FIG. 2A was stripped and rehybridized with $^{32}$P-labeled p53 cDNA (B).

Therefore, it appeared that there was a correlation between p53 expression and AdRSVpHyde-mediated inhibition. To determine whether p-Hyde regulated p53 expression, the same Northern blot in FIG. 2A was stripped and rehybridized with p53 probe. Indeed an induction of p53 mRNA was observed in AdRSVpHyde transduced DU145 cells (FIG. 8). Furthermore, transduction of LNCaP cells by AdRSVpHyde showed DNA laddering pattern, a marker for cells undergoing apoptosis (FIG. 9), indicate that pHyde expression induced apoptosis in LNCaP cells. Taken together, these results demonstrate that p-Hyde may function via p53 pathway to induce apoptosis and its growth inhibition may depend on p53 expression in the target cells.

The previous study showed that pHyde has the dual ability to act like a tumor suppressor gene and induce susceptibility to apoptosis. The growth of prostate tumors in rats was greatly inhibited by p-Hyde. Moreover, prostate cancer cells expressing pHyde were more sensitive to UV DNA damage driving these cells into cell programmed death. In this study AdRSVpHyde was shown to have an effective inhibition on cell growth both in vitro and in vivo for the prostate cancer cells expressing p53, but not for the prostate cancer cells missing p53 expression. One possibility is the p-Hyde can induce apoptosis by p53-dependent (such as in DU145 and LNCaP cells) and p53-independent pathways which requires an outside cell death trigger such as UV or chemicals (such as methylnitrosourea) to act as a co-inducer for apoptosis. Consistent with our result that only DU145 and LNCaP, but not PPC-1, PC-3 and TSU-Pr, expressed p53 at mRNA level (FIG. 7), other groups found that only DU145 and LNCaP cells expressed p53 at protein level but not PC-3 and TSU-Pr. Interestingly, p53 protein in DU145 was claimed to be a mutant p53.[21] Therefore, it seems that existence of p53 protein, regardless of its wild-type or mutant status, is required for p-Hyde to act as a tumor suppressor gene alone. This possibility, that the mutation in p53 protein in DU145 cells may not affect its ability for pHyde-mediated growth inhibition, need to be further studied. Moreover, the potential inhibitory effects by combination of AdRSVpHyde and UV (or methylnitrosourea) on cells missing p53 protein expression (such as PC-3 and TSU-Pr) will be further characterized.

One interests and important finding of this study was that AdRSVpHyde induced p53 expression in DU145 cells. Not only this may explain that pHyde acts in a more global manner to induce susceptibility to apoptosis, but also partially explains why p-Hyde has a partial sequence homologue with TSAP-6, a human protein claimed to be involved in p53-associated pathway: because p-Hyde could be a rat homologue of TSAP-6 gene, or a member of the TSAP-6 like family which is involved in p53-associated pathway. Furthermore, there is very few, if any, identified cellular proteins which act as regulators for p53 gene, which is a transcription factor to act many downstream genes. The significance of the finding that p-Hyde up-regulates p53 expression and the consequent exploration for a now cellular regulation mechanism are exciting. Nevertheless, whether pHyde directly regulates p53 gene at the transcriptional level will be determined in our current study by employing p53 promoter/CAT reporter chimeric gene in the presence and absence of p-Hyde protein in DU145 cells.

In summary, pHyde is a novel a tumor suppressor gene and AdRSVpHyde effectively inhibites prostate cancer both in vitro and in vivo. The monotherapy of AdRSVpHyde alone or combined therapy of AdRSVpHyde with radio- or chemo-therapy should have an effective therapeutic potential for treatment of locally advanced prostate cancer.

EXAMPLE 3

The other classical method for detecting apoptosis, TUNEL assay, was also used to demonstrate that AdRSVpHyde indeed caused DU145 cells to apoptosis. Seventy two hours after viral transduction, DU145 cells growing on culture dish were subjected to TUNEL assay. There were more fluorescence-stained cells in AdRSVpHyde transduced cells (FIGS. 14C and 14F) compared to untreated control (FIGS. 14A and 14D) or control virus transduced cells, (FIGS. 14B and 14E), indicating that there were more apoptotoic cells in AsRSVpHyde treated cells than the latter two kinds. In addition, tumor sections from DU145 xenograft tumors growing in nude mice showed that there was a significant apoptosis occurring in AdRSVpHyde treated tumors (FIG. 15B), compared to that of untreated tumors (FIG. 15A) and control virus treated tumors.

Figure 14:
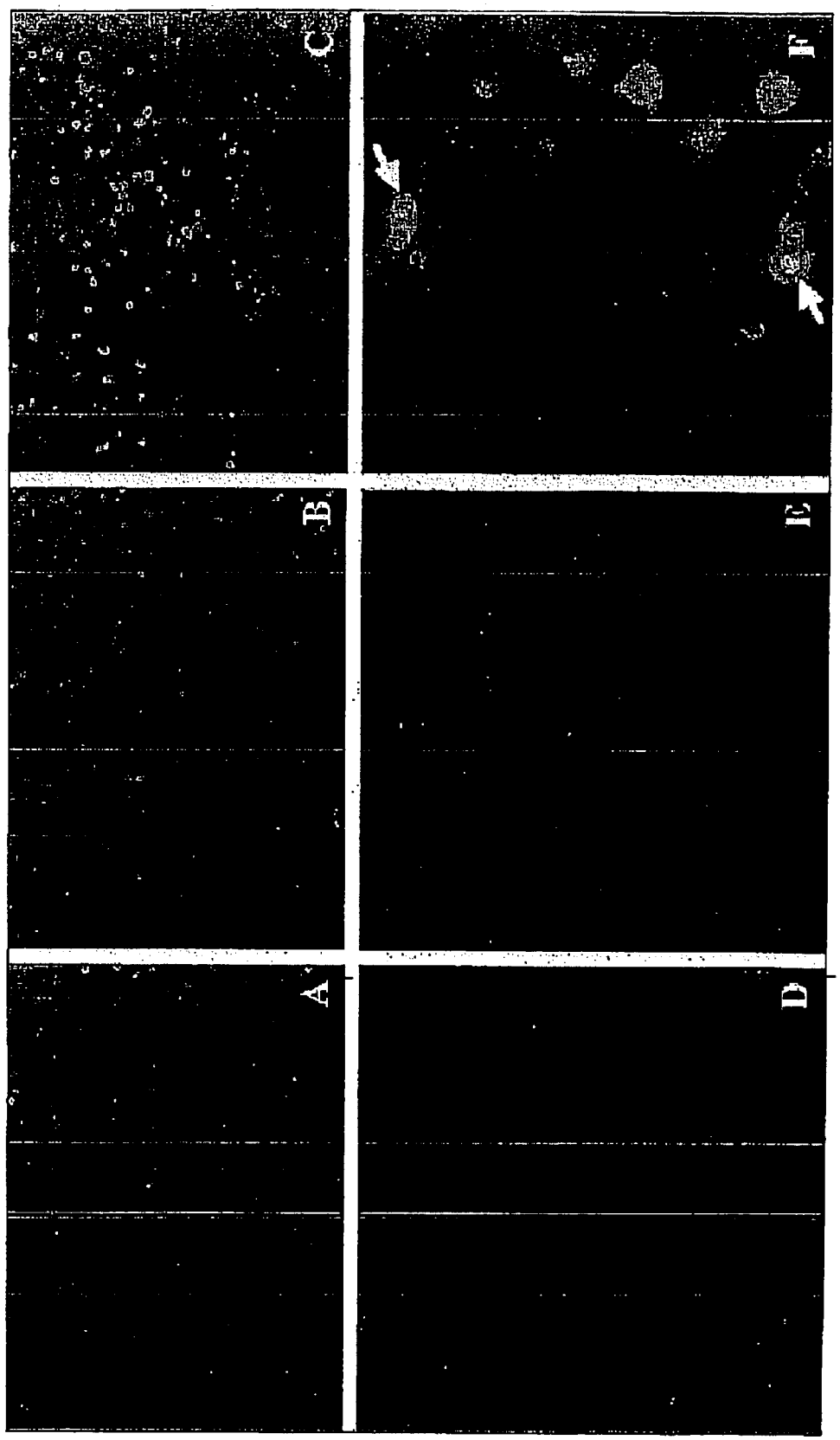
FIGS. 14A and 14F, TUNEL, assay of DU145 cells in vitro. DU145 cells were either untreated (A,D), or transduced with control virus (B, E) or AdRSVpHyde (C, F) at MOI=200, three days after transduction the cells were fixed and proceeded for TUNEL assay. The cells were then visualized by fluorescence microscopy. The arrows indicated some apoptotic cells. Magnification: A, B, C: ×20. D, E, F: ×40.

The TNUEL assay conducted on AdRSVpHyde transduced DU145 cells did not show comparable numbers of apoptotic cells (about 10% stained cells FIG. 14) to account for the growth inhibition (76.9% inhibition, FIG. 16). One explanation is that the growth inhibition of the cells was recorded at day 5 after AdRSVpHyde transduction (FIG. 16), whereas the in vitro TUNEL staining was performed on cells 3 daus, after AdRSVpHyde transdution (FIG. 14). P-Hyde-mediated apoptosis may take time to peak, which might not be evident yet in cells at day 3 after viral transduction. In vivo TUNEL staining of AdRSVpHyde treated DU145 xenograft tumor sections, derived 21 days after AdRSVpHyde transduction, showed a significantly higher amount of apoptosis cells (FIG. 15) compared to that of in vitro TUNEL staining (FIG. 14). Another explanation is that apoptosis may accounts for only part of the pHyde-mediated growth inhibition, in other words, pHyde-mediated growth inhibition my be composed of apoptosis and some other unknown mechanisms. As described below, AdRSVpHyde was able to inhibit cell growth of another human prostate cancer cell line TSU, however, no apoptosis was observed in AdRSVpHyde transduced TSU cells.

To determine whether there is an association between p53 status and susceptibility to apoptosis by pHyde, four different human prostate cancer cell lines PC3, TSU, LNCaP and DU145 were screened for the endogenous expression of p53 and their sensitivity to the pHyde-mediated growth inhibition and apoptosis were compared. The Northern blot analysis showed that PC-3 and TSU cells did not express p53 at the mRNA levels, whereas both LNCaP and DU145 cells expressed p53 mRNA. In contrast, all four cell lines expressed comparable Rb mRNA levels (FIG. 17). Consistently, other group has showed that DU145 and LNCaP cells, but not PC-3 cells, expressed p53 protein by Western blot analysis.

Figure 18A:
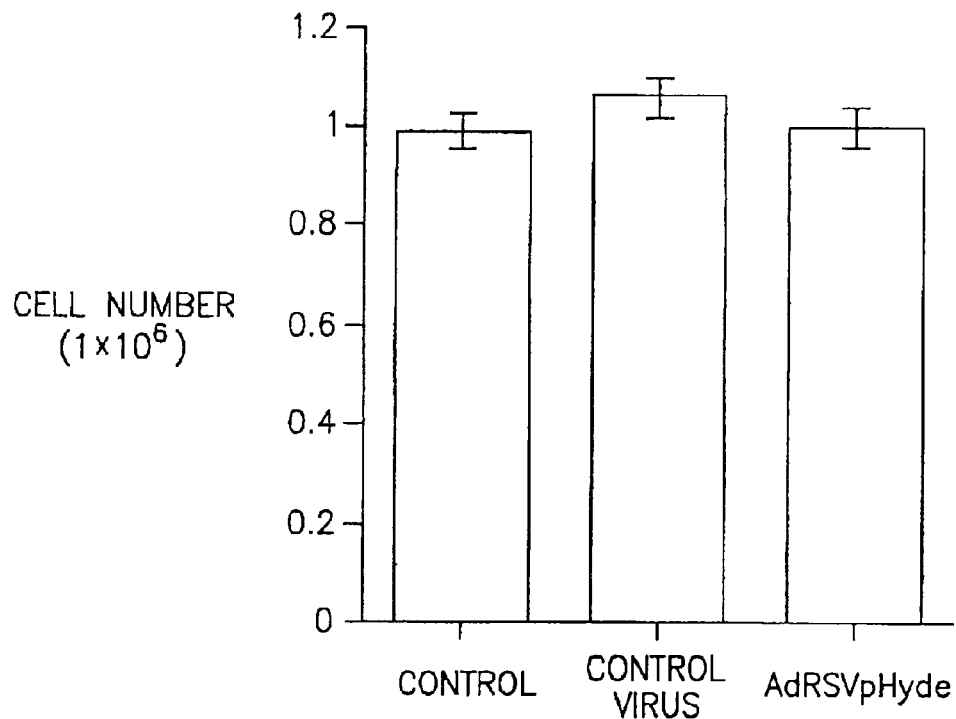
FIGS. 18A and 18B. Inhibitory effects of pHyde on growth of prostate cancer cell lines; PC-3 and TSU. PC-3 (A) and TSU (B) cells were transduced with or without adenoviral vectors (control virus or AdRSVpHyde) at MOI= 200. Cell numbers were counted at day 5 after viral transduction. The data represent the results from two independent experiments each performed in duplicate. *Some error bars were too small to see in the figure.
Figure 18B:
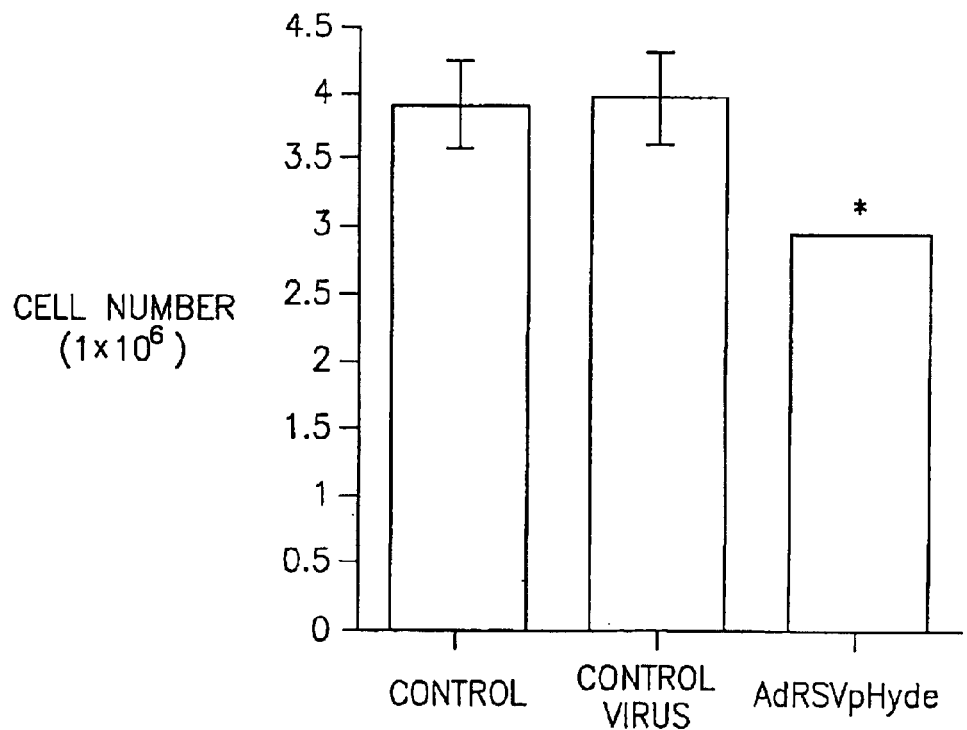

To determine the sensitivity of these four cell lines to the pHyde-mediated growth inhibition and apoptosis, cells were transduced with AdRSVpHyde and the growth was monitored AdRSVpHyde had a strong growth inhibition on DU145 and LNCaP cells (76.9% and 83.1% inhibition compared to the untreated control, respectively, FIG. 17), the two cell lines that expressed p53. Interestingly, for the two cell lines, PC-3 and TSU, not expressing p53, AdRSVpHyde had no inhibitory effect on the growth of PC-3 cells, but had a minor inhibitory effect (24.5% inhibition compared to untreated control) on the growth of TSU cells (FIG. 18). However, both AdRSVpHyde transduced PC-3 and TSU cells did not show any apoptosis as detected by DNA fragmentatin and TUNEL assays. These results suggest that there may be an association between the presence of p53 and the susceptibility of cell to the pHyde-mediated apoptosis. p53 may be required for the pHyde-mediated apoptotic induction. In addition, preliminary results showed that caspase-3, a key apoptotic protease was elevated after AdRSVpHyde transduction in DU145 cells.

REFERENCES

Amson R B, Nemani M, Roperch J P, Israeli D. Bougueleret L, Le Gall I, Medhioub M, Lines-Gruz G, Lethrosne F, Pasturaud P, Piouffre L, Prieur S, Susini L, Alvaro V, Millasseau P, Guidicelli C, Bui H, Massart C, Cazed L, Dufour F, Bruzzoni-Giovanelli H, Owadi H, Hennion C, Charpak G, Dausset J, Calvo F, Oren M, Cohen D and A Telerman (1996). Isolation of 10 differentially expressed cDNAs in p53-induced apoptosis: Activation of the vertebrate homologue of the *Drosophila* seven in absentia gene, Proc.Natl.Acad.Sci.USA, 93, 3953–3957.

Anand S, Verma H, Kumar L and N Singh (1995) Induction of apoptosis in chronic myelogenous leukemia lymphocytes by hydroxyurea and adriamycin, Cancer Letters, 88, 101–105.

Ausubel F M, Brent R, Kingston R E, Moore D D, Seidman J G, Smith J A and K Struhl (1987–1997) Current protocols in molecular biology, John Wiley & Sons, Inc.

Boring C C, Squires T S and T Tong (1993) Cancer Statistics, Cancer 43, 7–26.

Carter B H, Piantadosi S and J T Isaacs (1990) Clinical evidence for and implications of the multistep development of prostate cancer, The Journal of Urol., 143, 742–746.

Carter B S, Beaty T H, Steinberg G D, Childs B and PC Walsh (1992) Mendelian inheritance of prostate cancer, Proc. Natl. Acad. Sci. USA, 89, 3367–3371.

Effert P J, Neubauer A, Walter P J, et al. (1992) Alteration of the p53 gene are associated with the progression of a human prostate carcinoma, J Urol, 147, 789–793.

El Deiry W S, Harper J W, O'Connor P M, Velculescu V E, Canman C E, Jackman J, Pietenpol J A, Burrell M, Hill D E, Wang Y, Wiman K G, Mercer W E, Kastan M B, Kohn K W, Elledge S J, Kinzler K W, and B Vogelstein (1994) WAF1/CIP1 is induced in p53-mediated G1 arrest and apoptosis Cancer Research, 54, 1169–1174.

Findenig G, Mader R M, Fritzer-Szekerez M, Steger G G and T Szekerez (1996), Modulation of 5-fluorouracil resistance in human colon tumor cell lines by azidothymidine,Ocol. Res. (US), 8, 189–196.

Fournier R E K, and P H Ruddle (1977) Microcell mediated transfer of murine chromosomes into mouse, chinese hamster and human somatic cells, Proc Natl.Acad.Sci USA, 74, 319–323.

Gerschenfeldt H K and Weissman I L (1986), Cloning of a cDNA for a T cell-specific serine protease from a cytotoxic T lymphocyte, Science, 232, 854–858.

Grem J L (1990) Fluoronated pyrimidines, in Cancer Chemotherapy:Principle and Practice, ed, by B A Chapner and J M Collins, Philadelphia: J B Lippincott, pp. 89–190.

Inaba M, Mitsuhashi J, Sawada H, Miike N, Naoe Y, Daimon A, Koizumi K, Tsujimoto H and M Fukushima (1996), Reduced activity of anabolizing enzymes in 5-fluorouracil-resistant human stomach cancer cells, Jpn J Cancer Res (Japan), 87, 212–220.

Isaacs W B, Carter B S, Ewing C M (1991) Wild-type p53 suppresses growth of human prostate cancer cells containing mutant p53 alleles, Cancer Res 51, 4716–4720.

Isaacs J T, Isaacs W B, Feitz W F J, and Scheres J (1986) Establishment and characterization of seven Dunning rat prostatic cancer cell lines and their use in developing methods for predicting metastatic abilities of prostate cancer, The Prostate, 9, 261–281.

Isaacs S T, Wake N, Coffey D S, and Sandberg A A (1982), Cancer Res, 42, 2353–2361.

Iwasaki T, Shinkai K, Mukai M, Yoshioka K, Fuji Y, Nakahara K, Matsuda H and H Akedo (1995) Cell cycle dependent invasion in vitro by rat ascites hepatoma cells, Int. J. Cancer, 63, 282–287.

Kaur G P, Rinaldy A, Lloyd R S and R S Athwal (1992) A gene that partially complements xeroderma pigmentosum group A cells maps to human chromosome 8, Somatic Cell and Molecular Genetics, 18, 371–379.

Kyprianou, N, Bains A K, and Jacobs S C. (1994) Induction of apoptosis in androgen-independent human prostate cancer cells undergoing thymineless death. Prostate 25, 66–75.

Kyprianou, N. (1994) Apoptosis: Therapeutic significance in the treatment of androgen-dependent and androgen-independent prostate cancer. World J Urol 12, 299–303.

Lennon G, Auffray C, Polymeropoulos A and N B Soares (1996) The I.M.A.G.E. Consortium: An Integrated Molecular Analysis of Genomes and Their Expression, Genomics, 33, 151 152.

Lowe S W, Schmitt E M, Smith S W, Osborne B A and T Jacks (1993) Nature (London) 362, 847–849.

Mangiarotti G, Chung S, Zucker C, and Lodish HF (1981) Selection and analysis of cloned develomentally regulated Dictiostelium discoidum genes by hybridization-competition, Nucleic Acids Res. 9, 947–963.

McConkey E H (1967) The fractionation of RNA's by sucrose gradient centrifugation, Methods in Enzymology, 12A, 620–634.

McDonnell T J, Troncoso P, Brisbay S M et al. (1992) Expression of the protooncogene bcl-2 in the prostate and its association with the emergence of androgen independent prostate cancer. Can Res 52, 6940–6944.

McLellan D L and R W Norman (1995) Hereditary aspects of prostate cancer, Can. Med. Assoc. J., 153, 895–900.

Mellon K, Thomson S, Charlton R G et al. (1992) p53, c-erB-2 and the epidermal growth factor receptor in the benign and malignant prostate, J Urol, 147, 496–499.

Michalovitz D, Halevy O and M Oren (1990) Conditional inhibition of transcription and of cell proliferation by temperature sensitive mutant of p53, Cell 62, 671–680.

Rinaldy A, Dodson M L, Darling T L, and Lloyd R S (1988) Gene cloning using cDNA libraries in a differential competition hybridization strategy: application to cloning XP-A related genes, DNA 7, 563–570.

Rinaldy A, Bellew T. Egli E, and Lloyd R S (1990) Increased UV resistance in xeroderma pigmentosum group A cells after transformation with a human genomic DNA clone, Proc Natl Acad Sci USA, 87, 6818–6822.

Sacks L (1996) Proc.Natl.Acad.Sci USA 93, 4742–4749.

Sachs L and J Lotem (1995) in Apoptosis and the Immune Response, ed. Gregory CD (Wiley, New York), pp. 371–403.

Sandberg A A (1992) Chromosome abnormalities and related events in prostate cancer, Human Pathology, 23, 368–380.

Sherr C (1993) Mammalian G1 cyclins. Cell 73, 1059–1065.

Shields P G and C C Harris (1991) Molecular epidemiology and the genetics of environmental cancer, J. of Am. Med. Assoc., 266, 681–687.

Silverberg E (1987) Statistical and epidemiologic data on urologic cancer, Cancer, 6, 692–717.

Steinberg G D, Carter B S, Beaty T H, Childs B and P C Walsh (1990) Family history and the risk of prostate cancer, Prostate, 17, 337–341.

Steiner M S and Barrack E R (1992) Transforming growth for-□1 overproduction in prostate cancer. Effects on growth in vivo and in vitro, Molec. Endocrin., 6, 15–25.

Steiner M S, Satterwhite D J and H L Moses (1995) Molecular insights into altered cell cycle regulation and genitourinary malignancy, Urol. Oncol., 1, 3–17.

Templeton L, K Alderink and A Rinaldy (1996) Down-regulation of wild-type p53 and up-regulation of PCNA by pXPA2 gene are associated with the partial correction of NER in XP-A transfectant, Proc. of the Am. Assoc. for Cancer Res., 37, 499.

Vogelstein B, Fearon E R, Hamilton S R, Kern S E, Preisinger A C, Leppert M, Nakamura Y, White C, Smits A M M and J L Bos (1988) Genetic alterations during colorectal-tumor development, New Engl. J. Med., 319, 525–532.

Wadhwa R, Pereira-Smith O M, Reddel R R, Sugimoto Y, Mitsui Y and C Kaul (1995) Correlation between complementation group for immortality and the cellular distribution of mortalin, Exp. Cell Res., 216, 101–106

Weinstein I B (1987) Growth factors, oncogenes, and multistage carcinogenesis, J. of Cell Biochem., 33, 213–224.

Weil M, M D Jacobson, H S R Coles, T J Davies, R L Gardner, K D Raff and M C Raff (1996) Constitutive expression of the machinery for programmed cell death, The Journal of Cell Biology, 133, 1052–1059.

Yonish-Rouach E, Renitzky D, Lotem J, Sachs L, Kimchi A and M Oren (1991) Wild-type p53 induces apoptosis of myeloid leukemic cells that is inhibited by interlekin-6, Nature (London), 352, 345–347.

Yuspa S H and M C Poirier (1988) Chemical carcinogenesis; from animal models to molecular models in one decade, Adv. Cancer Res., 50, 25–70.

What is claimed is:

1. A human p-Hyde polypeptide, wherein the amino acid sequence is set forth in SEQ ID Nos: 2 or 4.

2. The polypeptide of claim 1, wherein said polypeptide is encoded by a nucleic acid sequence as set forth in SEQ ID Nos: 1 or 3.

3. A fusion protein or chimeric comprising the polypeptide of claim 1.

4. A composition comprising the polypeptide of claim 1.

* * * * *

SEQUENCE LISTING

<160> NUMBER OF SEQ ID NOS: 11

<210> SEQ ID NO 1
<211> LENGTH: 1886
<212> TYPE: DNA
<213> ORGANISM: Human

<400> SEQUENCE: 1

```
ggggagctgc cgcggtcgct ccgagcggcg ggccgcagag ccaccaaaat gccagaagag        60
atggacaagc cactgatcag cctccacctg gtggacagcg atagtagcct tgccaaggtc       120
cccgatgagg cccccaaagt gagcatcctg ggtagcgggg actttgcccg ctccctggcc       180
acacgcctgg tgggctctgg cttcaaagtg gtggtgggga gccgcaaccc caaacgcaca       240
gccaggctgt ttccctcagc ggcccaagtg actttccaag aggaggcagt gagctccccg       300
gaggtcatct ttgtggctgt gttccgggag cactactctt cactgtgcag tctcagtgac       360
cagctggcgg gcaagatcct ggtggatgtg agcaacccta cagagcaaga gcaccttcag       420
catcgtgagt ccaatgctga gtacctggcc tccctcttcc ccacttgcac agtggtcaag       480
gccttcaatg tcatctctgc ctggaccctg caggctggcc caagggatgg taacgggcag       540
gtgcccatct gcggtgacca gccagaagcc aagcgtgctg tctcggagat ggcgctcgcc       600
atgggcttca tgcccgtgga catgggatcc ctggcgtcag cctgggaggt ggaggccatg       660
cccctgcgcc tcctcccggc ctggaagtg cccaccctgc tggcctggg gctcttcgtc         720 tgcttctatg cctacaactt cgtccgggac gttctgcagc cctatgtgca ggaaagccag       780
aacaagttct tcaagctgcc cgtgtccgtg gtcaacacca cactgccgtg cgtggcctac       840
gtgctgctgt cactcgtgta cttgcccggc gtgctggcgg ctgccctgca gctgcggcgc       900
ggcaccaagt accagcgctt ccccgactgg ctggaccact ggctacagca ccgcaagcag       960
atcgggctgc tcagcttctt ctgcgccgcc ctgcacgccc tctacagctt ctgcttgccg      1020
ctgcgccgcg cccaccgcta cgacctggtc aacctggcag tcaagcaggt cttggccaac      1080
aagagccacc tctgggtgga ggaggtctgg cggatggaga tctacctctc cctgggagtg      1140
ctggccctcg gcacgttgtc cctgctgccc gtgacctcac tgccgtccat tgcaaactcg      1200
ctcaactgga gggagttcag cttcgttcag tcctcactgg gctttgtggc cctcgtgctg      1260
agcacactgc acacgctcac ctacggctgg acccgcgcct tcgaggagag ccgctacaag      1320
ttctacctgc ctcccacctt cacgctcacg ctgctggtgc cctgcgtcgt catcctggcc      1380
```

-continued

```
aaagccctgt tctcctgcc ctgcatcagc cgcagactcg ccaggatccg gagaggctgg    1440
gagagggaga gcaccatcaa gttcacgctg cccacagacc acgccctggc cgagaagacg    1500
agccacgtat gaggtgcctg ccctgggctc tggaccccgg gcacgcgagg acggtgccc    1560 tgagcccgtt aggttttctt ttcttggtgg tgcaaagtgg tataactgtg tgcaaatagg    1620
aggtttgagg tccaaattcc tgggactcaa atgtatgcag tactattcag aatgatatac    1680
acacatatgt gtatatgtat ttacatatat tccacatata taacaggatt tgcaattata    1740
catagctagc taaaaagttg ggtctctgag atttcaactt gtagatttaa aaacaagtgc    1800
cgtacgttaa gagaagagca gatcatgcta ttgtgacatt tgcagagata tacacacact    1860
ttttgtacag aaaaaaaaaa aaaaaa                                        1886
```

<210> SEQ ID NO 2
<211> LENGTH: 487
<212> TYPE: PRT
<213> ORGANISM: Human

<400> SEQUENCE: 2

```
Met Pro Glu Glu Met Asp Lys Pro Leu Ile Ser Leu His Leu Val Asp
1               5                   10                  15

Ser Asp Ser Ser Leu Ala Lys Val Pro Asp Glu Ala Pro Lys Val Ser
            20                  25                  30

Ile Leu Gly Ser Gly Asp Phe Ala Arg Ser Leu Ala Thr Arg Leu Val
        35                  40                  45

Gly Ser Gly Phe Lys Val Val Gly Ser Arg Asn Pro Lys Arg Thr
    50                  55                  60

Ala Arg Leu Phe Pro Ser Ala Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ser Asp Gln Leu Ala Gly Lys Ile Leu Val
            100                 105                 110

Asp Val Ser Asn Pro Thr Glu Gln Glu His Leu Gln His Arg Glu Ser
        115                 120                 125

Asn Ala Glu Tyr Leu Ala Ser Leu Phe Pro Thr Cys Thr Val Val Lys
    130                 135                 140

Ala Phe Asn Val Ile Ser Ala Trp Thr Leu Gln Ala Gly Pro Arg Asp
145                 150                 155                 160

Gly Asn Gly Gln Val Pro Ile Cys Gly Asp Gln Pro Glu Ala Lys Arg
                165                 170                 175

Ala Val Ser Glu Met Ala Leu Ala Met Gly Phe Met Pro Val Asp Met
            180                 185                 190

Gly Ser Leu Ala Ser Ala Trp Glu Val Glu Ala Met Pro Leu Arg Leu
        195                 200                 205

Leu Pro Ala Trp Lys Val Pro Thr Leu Leu Ala Leu Gly Leu Phe Val
    210                 215                 220

Cys Phe Tyr Ala Tyr Asn Phe Val Arg Asp Val Leu Gln Pro Tyr Val
225                 230                 235                 240

Gln Glu Ser Gln Asn Lys Phe Phe Lys Leu Pro Val Ser Val Asn
                245                 250                 255

Thr Thr Leu Pro Cys Val Ala Tyr Val Leu Leu Ser Leu Val Tyr Leu
            260                 265                 270

Pro Gly Val Leu Ala Ala Leu Gln Leu Arg Arg Gly Thr Lys Tyr
        275                 280                 285
```

```
Gln Arg Phe Pro Asp Trp Leu Asp His Trp Leu Gln His Arg Lys Gln
    290                 295                 300
Ile Gly Leu Leu Ser Phe Phe Cys Ala Ala Leu His Ala Leu Tyr Ser
305                 310                 315                 320
Phe Cys Leu Pro Leu Arg Arg Ala His Arg Tyr Asp Leu Val Asn Leu
                325                 330                 335
Ala Val Lys Gln Val Leu Ala Asn Lys Ser His Leu Trp Val Glu Glu
            340                 345                 350
Val Trp Arg Met Glu Ile Tyr Leu Ser Leu Gly Val Leu Ala Leu Gly
        355                 360                 365
Thr Leu Ser Leu Leu Ala Val Thr Ser Leu Pro Ser Ile Ala Asn Ser
    370                 375                 380
Leu Asn Trp Arg Glu Phe Ser Phe Val Gln Ser Ser Leu Gly Phe Val
385                 390                 395                 400
Ala Leu Val Leu Ser Thr Leu His Thr Leu Thr Tyr Gly Trp Thr Arg
                405                 410                 415
Ala Phe Glu Glu Ser Arg Tyr Lys Phe Tyr Leu Pro Pro Thr Phe Thr
            420                 425                 430
Leu Thr Leu Leu Val Pro Cys Val Val Ile Leu Ala Lys Ala Leu Phe
        435                 440                 445
Leu Leu Pro Cys Ile Ser Arg Arg Leu Ala Arg Ile Arg Arg Gly Trp
    450                 455                 460
Glu Arg Glu Ser Thr Ile Lys Phe Thr Leu Pro Thr Asp His Ala Leu
465                 470                 475                 480
Ala Glu Lys Thr Ser His Val
                485

<210> SEQ ID NO 3
<211> LENGTH: 2118
<212> TYPE: DNA
<213> ORGANISM: Human

<400> SEQUENCE: 3
ggggagctgc cgcggtcgct ccgagcggcg ggccgcagag ccaccaaaat gccagaagag     60
atggacaagc cactgatcag cctccacctg gtggacagcg atagtagcct tgccaaggtc    120
cccgatgagg cccccaaagt gagcatcctg ggtagcgggg actttgcccg ctccctggcc    180
acacgcctgg tgggctctgg cttcaaagtg gtggtgggga gccgcaaccc caaacgcaca    240
gccaggctgt ttccctcagc ggcccaagtg actttccaag aggaggcagt gagctcccg     300 gaggtcatct ttgtggctgt gttccgggag cactactctt cactgtgcag tctcagtgac    360
cagctggcgg gcaagatcct ggtggatgtg agcaacccta cagagcaaga gcaccttcag    420
catcgtgagt ccaatgctga gtacctggcc tccctcttcc ccacttgcac agtggtcaag    480
gccttcaatg tcatctctgc ctggaccctg caggctggcc aagggatgg taacgggcag    540 gtgcccatct gcggtgacca gccagaagcc aagcgtgctg tctcggagat ggcgctcgcc    600
atgggcttca tgcccgtgga catgggatcc ctggcgtcag cctgggaggt ggaggccatg    660
cccctgcgcc tcctcccggc ctggaaggtg cccaccctgc tggccctggg gctcttcgtc    720
tgcttctatg cctacaactt cgtccgggac gttctgcagc cctatgtgca ggaaagccag    780
aacaagttct tcaagctgcc cgtgtccgtg gtcaacacca cactgccgtg cgtggcctac    840
gtgctgctgt cactcgtgta cttgcccggc gtgctggcgg ctgccctgca gctgcggcgc    900
ggcaccaagt accagcgctt ccccgactgg ctggaccact ggctacagca ccgcaagcag    960
```

-continued

```
atcgggctgc tcagcttctt ctgcgccgcc ctgcacgccc tctacagctt ctgcttgccg    1020
ctgcgccgcg cccaccgcta cgacctggtc aacctggcag tcaagcaggt cttggccaac    1080
aagagccacc tctgggtgga ggaggtctgg cggatggaga tctacctctc cctgggagtg    1140
ctggccctcg gcacgttgtc cctgctggcc gtgacctcac tgccgtccat tgcaaactcg    1200
ctcaactgga gggagttcag cttcgttcag tgtgtggcaa cttccagtgc aggaaacaca    1260
ggcagtggaa cccgaagacc tgaatctcag tcccaagacc cccacttacc tgccccgcat    1320
catcagacaa gtttcctagg ccctcggagc ttctgctgct cacttgtgcc tgtgtccacc    1380
ccatatggtc atcaagagga tttgagctgg acacgttaaa tgcaggatgc gtgcagccaa    1440
cagtggcatg ctggcttttg agtcctcact gggctttgtg gccctcgtgc tgagcacact    1500
gcacacgctc acctacggct ggacccgcgc cttcgaggag agccgctaca agttctacct    1560
gcctcccacc ttcacgctca cgctgctggt gccctgcgtc gtcatcctgg ccaaagccct    1620
gtttctcctg ccctgcatca gccgcagact cgccaggatc cggagaggct gggagaggga    1680
gagcaccatc aagttcacgc tgcccacaga ccacgccctg ccgagaaga cgagccacgt    1740 atgaggtgcc tgccctgggc tctggacccc gggcacacga gggacggtgc cctgagcccg    1800
ttaggttttc ttttcttggt ggtgcaaagt ggtataactg tgtgcaaata ggaggtttga    1860
ggtccaaatt cctgggactc aaatgtatgc agtactattc agaatgatat acacacatat    1920
gtgtatatgt atttacatat attccacata tataacagga tttgcaatta tacatagcta    1980
gctaaaaagt tgggtctctg agatttcaac ttgtagattt aaaaacaagt gccgtacgtt    2040
aagagaagag cagatcatgc tattgtgaca tttgcagaga tatacacaca cttttttgtac   2100 agaaaaaaaa aaaaaaaa                                                  2118
```

<210> SEQ ID NO 4
<211> LENGTH: 456
<212> TYPE: PRT
<213> ORGANISM: Human

<400> SEQUENCE: 4

```
Met Pro Glu Glu Met Asp Lys Pro Leu Ile Ser Leu His Leu Val Asp
 1               5                  10                  15

Ser Asp Ser Ser Leu Ala Lys Val Pro Asp Glu Ala Pro Lys Val Ser
            20                  25                  30

Ile Leu Gly Ser Gly Asp Phe Ala Arg Ser Leu Ala Thr Arg Leu Val
        35                  40                  45

Gly Ser Gly Phe Lys Val Val Val Gly Ser Arg Asn Pro Lys Arg Thr
    50                  55                  60

Ala Arg Leu Phe Pro Ser Ala Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ser Asp Gln Leu Ala Gly Lys Ile Leu Val
            100                 105                 110

Asp Val Ser Asn Pro Thr Glu Gln Glu His Leu Gln His Arg Glu Ser
        115                 120                 125

Asn Ala Glu Tyr Leu Ala Ser Leu Phe Pro Thr Cys Thr Val Val Lys
    130                 135                 140

Ala Phe Asn Val Ile Ser Ala Trp Thr Leu Gln Ala Gly Pro Arg Asp
145                 150                 155                 160
```

```
Gly Asn Gly Gln Val Pro Ile Cys Gly Asp Gln Pro Glu Ala Lys Arg
                165                 170                 175
Ala Val Ser Glu Met Ala Leu Ala Met Gly Phe Met Pro Val Asp Met
            180                 185                 190
Gly Ser Leu Ala Ser Ala Trp Glu Val Glu Ala Met Pro Leu Arg Leu
        195                 200                 205
Leu Pro Ala Trp Lys Val Pro Thr Leu Leu Ala Leu Gly Leu Phe Val
    210                 215                 220
Cys Phe Tyr Ala Tyr Asn Phe Val Arg Asp Val Leu Gln Pro Tyr Val
225                 230                 235                 240
Gln Glu Ser Gln Asn Lys Phe Lys Leu Pro Val Ser Val Val Asn
                245                 250                 255
Thr Thr Leu Pro Cys Val Ala Tyr Val Leu Leu Ser Leu Val Tyr Leu
            260                 265                 270
Pro Gly Val Leu Ala Ala Leu Gln Leu Arg Arg Gly Thr Lys Tyr
        275                 280                 285
Gln Arg Phe Pro Asp Trp Leu Asp His Trp Leu Gln His Arg Lys Gln
    290                 295                 300
Ile Gly Leu Leu Ser Phe Phe Cys Ala Ala Leu His Ala Leu Tyr Ser
305                 310                 315                 320
Phe Cys Leu Pro Leu Arg Arg Ala His Arg Tyr Asp Leu Val Asn Leu
                325                 330                 335
Ala Val Lys Gln Val Leu Ala Asn Lys Ser His Leu Trp Val Glu Glu
            340                 345                 350
Val Trp Arg Met Glu Ile Tyr Leu Ser Leu Gly Val Leu Ala Leu Gly
        355                 360                 365
Thr Leu Ser Leu Leu Ala Val Thr Ser Leu Pro Ser Ile Ala Asn Ser
    370                 375                 380
Leu Asn Trp Arg Glu Phe Ser Phe Val Gln Cys Val Ala Thr Ser Ser
385                 390                 395                 400
Ala Gly Asn Thr Gly Ser Gly Thr Arg Arg Pro Glu Ser Gln Ser Gln
                405                 410                 415
Asp Pro His Leu Pro Ala Pro His Gln Thr Ser Phe Leu Gly Pro
            420                 425                 430
Arg Ser Phe Cys Cys Ser Leu Val Pro Val Ser Thr Pro Tyr Gly His
        435                 440                 445
Gln Glu Asp Leu Ser Trp Thr Arg
    450                 455

<210> SEQ ID NO 5
<211> LENGTH: 2714
<212> TYPE: DNA
<213> ORGANISM: Rat

<400> SEQUENCE: 5
gaattcggca cgaggctgcc gaggcactgt gatgtccggg gagatggaca aaccgctcat    60
cagtcgccgc ttggtggaca gtgatggcag tctggctgag gtccccaagg aggctcccaa   120
agtgggcatc ctgggcagcg ggattttgc ccggtccctg gccacacgcc tggtgggctc   180
tggcttcttt gtggtggtgg aagccgtaa ccccaaacgc actgccggcc tcttcccctc   240
cttagcccaa gtgactttcc aggaggaggc cgtgagctct ccagaggtca tctttgtggc   300
cgtgttccgg gagcactact cctcactgtg cagtcttgct gaccagttgg ctggcaagat   360
cctagtggat gtaagcaacc ccacggagaa ggagcgtctt cagcaccgcc agtcgaacgc   420
```

```
cgagtacctg gcctccctct tccctgcctg cactgtggtc aaggccttca acgtcatctc    480
tgcatgggcc ctacaggctg gcccaaggga tgggaacagg caggtgctca tctgcggtga    540
ccagctggaa gccaagcaca ccgtctcaga gatggcgcgc gccatgggtt tcaccccact    600
ggacatggga tccctggcct cagcgaggga ggtagaggcc ataccctgc gcctccttcc     660
atcctggaag gtgcccaccc tcctggccct ggggctaagc acacaaagct atgcctacaa    720
cttcatccgg gacgttctac agccgtacat ccggaaagat gagaacaagt tctacaagat    780
gccctgtct gtggtcaaca ccacgatacc ctgtgtggct acgtgctgc tgtccctggt      840
ttacctgcct ggtgtgctgg cagctgccct tcagctgagg aggggaccac agtaccagcg    900
cttcccagac tggctggacc attggctgca gcaccgcaag cagatcgggc tactcagctt    960
ttttttcgcc atgctgcacg ctctctacag cttctgcctg ccgctgcgcc gctcccaccg   1020
ctatgatctg gtcaacctgg ctgtgaagca ggtcctggcc aacaagagcc gcctctgggt   1080
tgaggaagaa gtctggcgga tggagatata cctgtccctg ggtgtgctgg ctctgggcat   1140
gctgtcactg ctggcggtta cctcgatccc ttccattgca aactcactca actggaagga   1200
gttcagcttt gtgcagtcca cgctgggctt cgtggccctg atgctgagca caatgcacac   1260
cctcacctac ggctggaccc gtgcttttga ggaaaaccac tacaagttct acctgccacc   1320
cacattcacg ctcacgctgc tcctgccctg tgtcatcatc ctggccaagg gcctcttcct   1380
cctgccctgc ctcagccaca gactcaccaa gatccgcagg ggctgggaga gggatggtgc   1440
cgtcaagttc atgctgcccg ctggccacac acaggggag aaaacaagcc acgtgtgagg    1500
ccctggaaat ggagacaggc acagcttgtg ggggccctgg gctgggttcg ggtctctttt   1560
ctgggatggt atatgcgtgg gtggccgagg tctgaatttc tgggatgcag gtgtatgccg   1620
agatactcag aatggcgtac cacacatgcg ataagtactc acatatattt catatataat   1680
aggatttact attattctta gttaaaaaaa aatagtgggt ccttatattt caacttatgc   1740
agggtcccta tatttcaact tgagcatttc agagcaaatg ccacacatta aacagcagat   1800
cccaccccttg tggtagctgc agagacagac agaaacttct ggttatgaga gagactgtat  1860
tttgttggat tctacccttta atccccgttc tctacgttcc cctgttagcc acatcttaac   1920
gttggtgcag agctgggaca agagctggct ctggtgcagc ctcccccatc ccagggctag   1980
gaaacaagcc tctgatgaac agagggacca ggtctggacc ctcctgctcc cgcttccctg   2040
ggctcgagtg gggaggctca gcgggatccc ccgcaatctg tgcaggagtt ttcacaggtc   2100
tgtcctttct tccgggagcg gtctgaagcg gccccatctg atcctagctg agccgagatt   2160
gttccccact ccctgaaagt ccagagtcac cgtggagcct gcaaattgct ccttctgcga   2220
aggtgtgaag tcaccgtctc accagagcca ttaacgaacc tgatcttcag aagaagcata   2280
attgtttccc ctccattaag ttggtggtga ccctctttaa accactgtgc cttctcgcct   2340
ttcccatcac taatttgggc atctccatgg agtggactct tgtcgggca gttcagggga    2400
gagggaagca ttagagattg cggagaataa ccatcgaagc ctcccttgga tgttcccagg   2460
cgtgccttca ttaaattggt ccctaatgag aatgacaggg gaccctgtt gcctgtatgc     2520
agagaaccag ccttctgagc acccaggaaa cacagtggcc ccacgccctt caggggggtc   2580
ccacgtcccc tttcccatgc ttttgcctcc ctccctcccg gttacaatca accataaaag   2640
tctgcaaata ttgttttttg aattcttaaa gagaccacat cctttgttat taccaaaaaa   2700
aaaaaaaaaa aaac                                                     2714
```

```
<210> SEQ ID NO 6
<211> LENGTH: 488
<212> TYPE: PRT
<213> ORGANISM: Rat

<400> SEQUENCE: 6
```

| | | | | | | | | | | | | | | | |
|---|---|---|---|---|---|---|---|---|---|---|---|---|---|---|---|
|Met|Ser|Gly|Glu|Met|Asp|Lys|Pro|Leu|Ile|Ser|Arg|Arg|Leu|Val|Asp|
|1| | | |5| | | | |10| | | | |15| |
|Ser|Asp|Gly|Ser|Leu|Ala|Glu|Val|Pro|Lys|Glu|Ala|Pro|Lys|Val|Gly|
| | | |20| | | | |25| | | | |30| | |
|Ile|Leu|Gly|Ser|Gly|Asp|Phe|Ala|Arg|Ser|Leu|Ala|Thr|Arg|Leu|Val|
| | | |35| | | | |40| | | | |45| | |
|Gly|Ser|Gly|Phe|Phe|Val|Val|Val|Gly|Ser|Arg|Asn|Pro|Lys|Arg|Thr|
| | |50| | | | |55| | | | |60| | | |
|Ala|Gly|Leu|Phe|Pro|Ser|Leu|Ala|Gln|Val|Thr|Phe|Gln|Glu|Glu|Ala|
|65| | | | |70| | | | |75| | | | |80|
|Val|Ser|Ser|Pro|Glu|Val|Ile|Phe|Val|Ala|Val|Phe|Arg|Glu|His|Tyr|
| | | | |85| | | | |90| | | | |95| |
|Ser|Ser|Leu|Cys|Ser|Leu|Ala|Asp|Gln|Leu|Ala|Gly|Lys|Ile|Leu|Val|
| | | |100| | | | |105| | | | |110| | |
|Asp|Val|Ser|Asn|Pro|Thr|Glu|Lys|Glu|Arg|Leu|Gln|His|Arg|Gln|Ser|
| | | |115| | | | |120| | | | |125| | |
|Asn|Ala|Glu|Tyr|Leu|Ala|Ser|Leu|Phe|Pro|Ala|Cys|Thr|Val|Val|Lys|
| | |130| | | | |135| | | | |140| | | |
|Ala|Phe|Asn|Val|Ile|Ser|Ala|Trp|Ala|Leu|Gln|Ala|Gly|Pro|Arg|Asp|
|145| | | | |150| | | | |155| | | | |160|
|Gly|Asn|Arg|Gln|Val|Leu|Ile|Cys|Gly|Asp|Gln|Leu|Glu|Ala|Lys|His|
| | | | |165| | | | |170| | | | |175| |
|Thr|Val|Ser|Glu|Met|Ala|Arg|Ala|Met|Gly|Phe|Thr|Pro|Leu|Asp|Met|
| | | |180| | | | |185| | | | |190| | |
|Gly|Ser|Leu|Ala|Ser|Ala|Arg|Glu|Val|Glu|Ala|Ile|Pro|Leu|Arg|Leu|
| | | |195| | | | |200| | | | |205| | |
|Leu|Pro|Ser|Trp|Lys|Val|Pro|Thr|Leu|Leu|Ala|Leu|Gly|Leu|Ser|Thr|
| | |210| | | | |215| | | | |220| | | |
|Gln|Ser|Tyr|Ala|Tyr|Asn|Phe|Ile|Arg|Asp|Val|Leu|Gln|Pro|Tyr|Ile|
|225| | | | |230| | | | |235| | | | |240|
|Arg|Lys|Asp|Glu|Asn|Lys|Phe|Tyr|Lys|Met|Pro|Leu|Ser|Val|Val|Asn|
| | | | |245| | | | |250| | | | |255| |
|Thr|Thr|Ile|Pro|Cys|Val|Ala|Tyr|Val|Leu|Leu|Ser|Leu|Val|Tyr|Leu|
| | | |260| | | | |265| | | | |270| | |
|Pro|Gly|Val|Leu|Ala|Ala|Ala|Leu|Gln|Leu|Arg|Arg|Gly|Thr|Lys|Tyr|
| | |275| | | | |280| | | | |285| | | |
|Gln|Arg|Phe|Pro|Asp|Trp|Leu|Asp|His|Trp|Leu|Gln|His|Arg|Lys|Gln|
|290| | | | |295| | | | |300| | | | | |
|Ile|Gly|Leu|Leu|Ser|Phe|Phe|Ala|Met|Leu|His|Ala|Leu|Tyr|Ser|
|305| | | | |310| | | | |315| | | | |320|
|Phe|Cys|Leu|Pro|Leu|Arg|Arg|Ser|His|Arg|Tyr|Asp|Leu|Val|Asn|Leu|
| | | |325| | | | |330| | | | |335| | |
|Ala|Val|Lys|Gln|Val|Leu|Ala|Asn|Lys|Ser|Arg|Leu|Trp|Val|Glu|Glu|
| | |340| | | | |345| | | | |350| | | |
|Glu|Val|Trp|Arg|Met|Glu|Ile|Tyr|Leu|Ser|Leu|Gly|Val|Leu|Ala|Leu|
| | |355| | | | |360| | | | |365| | | |
|Gly|Met|Leu|Ser|Leu|Leu|Ala|Val|Thr|Ser|Ile|Pro|Ser|Ile|Ala|Asn|
| | |370| | | | |375| | | | |380| | | |

-continued

```
Ser Leu Asn Trp Lys Glu Phe Ser Phe Val Gln Ser Thr Leu Gly Phe
385                 390                 395                 400

Val Ala Leu Met Leu Ser Thr Met His Thr Leu Thr Tyr Gly Trp Thr
                405                 410                 415

Arg Ala Phe Glu Glu Asn His Tyr Lys Phe Tyr Leu Pro Pro Thr Phe
            420                 425                 430

Thr Leu Thr Leu Leu Pro Cys Val Ile Ile Leu Ala Lys Gly Leu
        435                 440                 445

Phe Leu Leu Pro Cys Leu Ser His Arg Leu Thr Lys Ile Arg Arg Gly
    450                 455                 460

Trp Glu Arg Asp Gly Ala Val Lys Phe Met Leu Pro Ala Gly His Thr
465                 470                 475                 480

Gln Gly Glu Lys Thr Ser His Val
                485

<210> SEQ ID NO 7
<211> LENGTH: 33
<212> TYPE: DNA
<213> ORGANISM: Human

<400> SEQUENCE: 7
tccctggcca cacgcctggt gggctctggc ttc                                  33

<210> SEQ ID NO 8
<211> LENGTH: 54
<212> TYPE: PRT
<213> ORGANISM: Rat

<400> SEQUENCE: 8

Ala Ala Pro Cys Val Ala Tyr Val Leu Leu Ser Leu Val Tyr Leu Pro
1               5                   10                  15

Gly Val Leu Ala Ala Ala Leu Gln Leu Arg Arg Gly Thr Lys Tyr Gln
            20                  25                  30

Arg Phe Pro Asp Trp Leu Asp His Trp Leu Gln His Arg Lys Gln Ile
        35                  40                  45

Gly Leu Leu Ser Phe Phe
    50

<210> SEQ ID NO 9
<211> LENGTH: 17
<212> TYPE: PRT
<213> ORGANISM: Rat

<400> SEQUENCE: 9

Asn Phe Ile Arg Asp Val Leu Gln Pro Tyr Ile Arg Lys Asp Glu Asn
1               5                   10                  15

Lys

<210> SEQ ID NO 10
<211> LENGTH: 3884
<212> TYPE: DNA
<213> ORGANISM: Rat

<400> SEQUENCE: 10
gcggccgcca tcatcaataa tataccttat tttggattga agccaatatg ataatgaggg     60
ggtggagttt gtgacgtggc gcggggcgtg gaacggggc gggtgacgta gtagtgtggc    120
ggaagtgtga tgttgcaagt gtggcggaac acatgtaagc gacggatgtg caaaagtga    180 cgttttggt gtgcgccggt gtacacagga agtgacaatt tcgcgcggt tttaggcgga    240
```

-continued

```
tgttgtagta aatttgggcg taaccgagta agatttggcc attttcgcgg gaaaactgaa    300
taagaggaag tgaaatctga ataattttgt gttactcata gcgcgtaata tttgtctagg    360
gccgcgggga ctttgaccgt ttacgtggag actcgcccag ggcgcgcccc gatgtacggg    420
ccagatatac gcgtatctga ggggactagg gtgtgtttag gcgaaaagcg gggcttcggt    480
tgtacgcggt taggagtccc ctcaggatat agtagtttcg cttttgcata gggaggggga    540
aatgtagtct tatgcaatac tcttgtagtc ttgcaacatg gtaacgatga gttagcaaca    600
tgccttacaa ggagagaaaa agcaccgtgc atgccgattg gtggaagtaa ggtggtacga    660
tcgtgcctta ttaggaaggc aacagacggg tctgacatgg attggacgaa ccactgaatt    720
ccgcattgca gagatattgt atttaagtgc ctagctcgat acaataaacg ccatttgacc    780
attcaccaca ttggtgtgca cctccggccc tggccactct cttccgcatc gctgtctgcg    840
ggggccagct gttgggctcg cggttgagga caaactcttc gcggtctttc cagtactctt    900
ggatcggaaa cccgtcggcc tccgaacggt actccgccgc cgagggacct gagcgagtcc    960
gcatcgaccg gatcggaaaa cctctcgaga aggcgtgta accagtcaca gtcgctctag   1020
aactagtgga tcccccgggc tgcaggaatt cgataattcg gcacgaggct gccgaggcac   1080
tgtgatgtcc ggggagatgg acaaaccgct catcagtcgc cgcttggtgg acagtgatgg   1140
cagtctggct gaggtcccca aggaggctcc caaagtgggc atcctgggca gcgggatttt   1200
tgcccggtcc ctggccacac gcctggtggg ctctggcttc tttgtggtgg tgggaagccg   1260
taaccccaaa cgcactgccg gcctcttccc ctccttagcc caagtgactt ccaggagga   1320 ggccgtgagc tctccagagg tcatctttgt ggccgtgttc cgggagcact actcctcact   1380
gtgcagtctt gctgaccagt tggctggcaa gatcctagtg gatgtaagca cccccacgga   1440
gaaggagcgt cttcagcacc gccagtcgaa cgccgagtac ctggcctccc tcttccctgc   1500
ctgcactgtg gtcaaggcct tcaacgtcat ctctgcatgg gccctacagg ctggcccaag   1560
ggatgggaac aggcaggtgc tcatctgcgg tgaccagctg gaagccaagc acaccgtctc   1620
agagatggcg cgcgccatgg gtttcacccc actggacatg ggatccctgg cctcagcgag   1680
ggaggtagag gccataccc tgcgcctcct tccatcctgg aaggtgccca ccctcctggc   1740
cctgggctaa gcacacaaa gctatgccta caacttcatc cgggacgttc tacagccgta   1800
catccggaaa gatgagaaca agttctacaa gatgcccctg tctgtggtca acaccacgat   1860
accctgtgtg gcttacgtgc tgctgtccct ggtttacctg cctggtgtgc tggcagctgc   1920
ccttcagctg aggaggggga ccaagtacca gcgcttccca gactggctgg accattggct   1980
gcagcaccgc aagcagatcg ggctactcag cttttttttc gccatgctgc acgctctcta   2040
cagcttctgc ctgccgctgc gccgctccca ccgctatgat ctggtcaacc tggctgtgaa   2100
gcaggtcctg gccaacaaga gccgcctctg ggttgaggaa gaagtctggc ggatggagat   2160
atacctgtcc ctgggtgtgc tggctctggg catgctgtca ctgctggcgg ttacctcgat   2220
cccttccatt gcaaactcac tcaactgaa ggagttcagc tttgtgcagt ccacgctggg   2280
cttcgtggcc ctgatgctga gcacaatgca caccctcacc tacggctgga cccgtgcttt   2340
tgaggaaaac cactacaagt tctacctgcc acccacattc acgctcacgc tgctcctgcc   2400
ctgtgtcatc atcctggcca agggcctctt cctcctgccc tgcctcagcc acagactcac   2460
caagatccgc aggggctggg agagggatgg tgccgtcaag ttcatgctgc ccgctggcca   2520
cacacagggg gagaaaacaa gccacgtgtg aggccctgga aatggagaca ggcacagctt   2580
```

```
gtgggggccc tgggctgggt tcgggtctct tttctgggat ggtatatgcg tgggtggccg      2640
aggtctgaat ttctgggatg caggtgtatg ccgagatact cagaatggcg taccacacat      2700
gcgataagta ctcacatata tttcatatat aataggattt actattattc ttagttaaaa      2760
aaaaatagtg ggtccttata tttcaactta tgcagggtcc ctatatttca acttgagcat      2820
ttcagagcaa atgccacaca ttaaacagca gatcccaccc ttgtggtagc tgcagagaca      2880
gacagaaact tctggttatg agagagactg tattttgttg gattctacct ttaatccccg      2940
ttctctacgt tcccctgtta gccacatctt aacgttggtg cagagctggg acaagagctg      3000
gctctggtgc agcctccccc atcccagggc taggaaacaa gcctctgatg aacagaggga      3060
ccaggtctgg accctcctgc tcccgcttcc ctgggctcga gtggggaggc tcagcgggat      3120
cccccgcaat ctgtgcagga gttttcacag gtctgtcctt tcttccggga gcggtctgaa      3180
gcggccccat ctgatcctag ctgagccgag attgttcccc actccctgaa agtccagagt      3240
caccgtggag cctgcaaatt gctccttctg cgaaggtgtg aagtcaccgt ctcaccagag      3300
ccattaacga acctgatctt cagaagaagc ataattgttt ccctccatt aagttggtgg       3360 tgaccctctt taaaccactg tgccttctcg cctttcccat cactaatttg ggcatctcca      3420
tggagtggac tcttgtcggg gcagttcagg ggggagggaa gcattagaga ttgcggagaa      3480
taaccatcga agcctccctt ggatgttccc aggcgtgcct tcattaaatt ggtccctaat      3540
gagaatgaca ggggacccct gttgcctgta tgcagagaac cagccttctg agcacccagg      3600
aaacacagtg gccccacgcc cttcagggg gtcccacgtc ccctttccca tgcttttgcc       3660
tccctccctc ccggttacaa tcaaccataa aagtctgcaa atattgtttt ttgaattatc      3720
aagcttatcg ataccgtcga aacttgttta ttgcagctta taatggttac aaataaagca      3780
atagcatcac aaatttcaca aataaagcat tttttcact gcattctagt tgtggtttgt       3840
ccaaactcat caatgtatct tatcatgtct ggatccgacc tcgg                       3884
```

<210> SEQ ID NO 11
<211> LENGTH: 32166
<212> TYPE: DNA
<213> ORGANISM: Rat

<400> SEQUENCE: 11

```
atctggaagg tgctgaggta cgatgagacc cgcaccaggt gcagaccctg cgagtgtggc       60
ggtaaacata ttaggaacca gcctgtgatg ctggatgtga ccgaggagct gaggcccgat      120
cacttggtgc tggcctgcac ccgcgctgag tttggctcta gcgatgaaga tacagattga      180
ggtactgaaa tgtgtgggcg tggcttaagg gtgggaaaga atatataagg tgggggtctt      240
atgtagtttt gtatctgttt tgcagcagcc gccgccgcca tgagcaccaa ctcgtttgat      300
ggaagcattg tgagctcata tttgacaacg cgcatgcccc catgggccgg ggtgcgtcag      360
aatgtgatgg gctccagcat tgatggtcgc cccgtcctgc ccgcaaactc tactaccttg      420
acctacgaga ccgtgtctgg aacgccgttg gagactgcag cctccgccgc cgcttcagcc      480
gctgcagcca ccgcccgcgg gattgtgact gactttgctt tcctgagccc gcttgcaagc      540
agtgcagctt cccgttcatc cgcccgcgat gacaagttga cggctctttt ggcacaattg      600
gattctttga cccgggaact taatgtcgtt tctcagcagc tgttggatct cgccagcag      660 gtttctgccc tgaaggcttc ctcccctccc aatgcggttt aaaacataaa taaaaaacca      720
gactctgttt ggatttggat caagcaagtg tcttgctgtc tttatttagg ggttttgcgc      780
gcgcggtagg cccgggacca gcggtctcgg tcgttgaggg tcctgtgtat ttttttccagg     840
```

-continued

```
acgtggtaaa ggtgactctg gatgttcaga tacatgggca taagcccgtc tctggggtgg      900
aggtagcacc actgcagagc ttcatgctgc ggggtggtgt tgtagatgat ccagtcgtag      960
caggagcgct gggcgtggtg cctaaaaatg tctttcagta gcaagctgat tgccaggggc     1020
aggcccttgg tgtaagtgtt tacaaagcgg ttaagctggg atgggtgcat acgtggggat     1080
atgagatgca tcttggactg tatttttagg ttggctatgt tcccagccat atccctccgg     1140
ggattcatgt tgtgcagaac caccagcaca gtgtatccgg tgcacttggg aaatttgtca     1200
tgtagcttag aaggaaatgc gtggaagaac ttggagacgc ccttgtgacc tccaagattt     1260
tccatgcatt cgtccataat gatggcaatg ggcccacggg cggcggcctg ggcgaagata     1320
tttctgggat cactaacgtc atagttgtgt tccaggatga gatcgtcata ggccattttt     1380
acaaagcgcg ggcggagggt gccagactgc ggtataatgg ttccatccgg cccaggggcg     1440
tagttaccct cacagatttg catttcccac gctttgagtt cagatggggg gatcatgtct     1500
acctgcgggg cgatgaagaa aacggtttcc ggggtagggg agatcagctg ggaagaaagc     1560
aggttcctga gcagctgcga cttaccgcag ccggtgggcc cgtaaatcac acctattacc     1620
gggtgcaact ggtagttaag agagctgcag ctgccgtcat ccctgagcag gggggccact     1680
tcgttaagca tgtccctgac tcgcatgttt ccctgacca aatccgccag aaggcgctcg     1740
ccgcccagcg atagcagttc ttgcaaggaa gcaaagtttt tcaacggttt gagaccgtcc     1800
gccgtaggca tgcttttgag cgtttgacca agcagttcca ggcggtccca cagctcggtc     1860
acctgctcta cggcatctcg atccagcata tctcctcgtt tcgcgggttg gggcggcttt     1920
cgctgtacgg cagtagtcgg tgctcgtcca gacgggccag ggtcatgtct ttccacgggc     1980
gcagggtcct cgtcagcgta gtctgggtca cggtgaaggg gtgcgctccg ggctgcgcgc     2040
tggccagggt gcgcttgagg ctggtcctgc tggtgctgaa gcgctgccgg tcttcgccct     2100
gcgcgtcggc caggtagcat ttgaccatgg tgtcatagtc cagcccctcc gcggcgtggc     2160
ccttggcgcg cagcttgccc ttggaggagg cgccgcacga ggggcagtgc agacttttga     2220
gggcgtagag cttgggcgcg agaaataccg attccgggga gtaggcatcc gcgccgcagg     2280
ccccgcagac ggtctcgcat tccacgagcc aggtgagctc tggccgttcg gggtcaaaaa     2340
ccaggttttcc cccatgcttt ttgatgcgtt tcttacctct ggtttccatg agccggtgtc     2400
cacgctcggt gacgaaaagg ctgtccgtgt ccccgtatac agacttgaga ggcctgtcct     2460
cgagcggtgt tccgcggtcc tcctcgtata gaaactcgga ccactctgag acaaaggctc     2520
gcgtccaggc cagcacgaag gaggctaagt gggagggta gcggtcgttg tccactaggg     2580
ggtccactcg ctccagggtg tgaagacaca tgtcgccctc ttcggcatca aggaaggtga     2640
ttggttgta ggtgtaggcc acgtgaccgg gtgttcctga agggggcta taaagggggg     2700
tggggcgcg ttcgtcctca ctctcttccg catcgctgtc tgcagggcc agctgttggg     2760
gtgagtactc cctctgaaaa gcgggcatga cttctgcgct aagattgtca gtttccaaaa     2820
acgaggagga tttgatattc acctggcccg cggtgatgcc tttgagggtg gccgcatcca     2880
tctggtcaga aaagacaatc tttttgttgt caagcttggt ggcaaacgac ccgtagaggg     2940
cgttggacag caacttggcg atggagcgca gggtttggtt tttgtcgcga tcggcgcgct     3000
ccttggccgc gatgtttagc tgcacgtatt cgcgcgcaac gcaccgccat tcgggaaaga     3060
cggtggtgcg ctcgtcgggc accaggtgca cgcgccaacc gcggttgtgc agggtgacaa     3120
ggtcaacgct ggtggctacc tctccgcgta ggcgctcgtt ggtccagcag aggcggccgc     3180
```

```
ccttgcgcga gcagaatggc ggtaggggt  ctagctgcgt ctcgtccggg gggtctgcgt    3240
ccacggtaaa gaccccgggc agcaggcgcg cgtcgaagta gtctatcttg catccttgca    3300
agtctagcgc ctgctgccat gcgcgggcg  caagcgcgcg ctcgtatggg ttgagtgggg    3360
gaccccatgg catgggtgg  gtgagcgcgg aggcgtacat gccgcaaatg tcgtaaacgt    3420
agagggctc  tctgagtatt ccaagatatg tagggtagca tcttccaccg cggatgctgg    3480
cgcgcacgta atcgtatagt tcgtgcgagg gagcgaggag gtcgggaccg aggttgctac    3540
gggcgggctg ctctgctcgg aagactatct gcctgaagat ggcatgtgag ttggatgata    3600
tggttggacg ctggaagacg ttgaagctgg cgtctgtgag acctaccgcg tcacgcacga    3660
aggaggcgta ggagtcgcgc agcttgttga ccagctcggc ggtgacctgc acgtctaggg    3720
cgcagtagtc cagggtttcc ttgatgatgt catacttatc ctgtcccttt ttttttccaca   3780
gctcgcggtt gaggacaaac tcttcgcggt cttttccagta ctcttggatc ggaaacccgt   3840
cggcctccga acgtaagag  cctagcatgt agaactggtt gacggcctgg taggcgcagc    3900
atccctttc  tacgggtagc gcgtatgcct gcgcggcctt ccggagcgag gtgtgggtga    3960
gcgcaaaggt gtccctgacc atgactttga ggtactggta tttgaagtca gtgtcgtcgc    4020
atccgccctg ctcccagagc aaaaagtccg tgcgcttttt ggaacgcgga tttggcaggg    4080
cgaaggtgac atcgttgaag agtatctttc ccgcgcgagg cataaagttg cgtgtgatgc    4140
ggaagggtcc cggcacctcg gaacggttgt taattacctg ggcggcgagc acgatctcgt    4200
caaagccgtt gatgttgtgg cccacaatgt aaagttccaa gaagcgcggg atgcccttga    4260
tggaaggcaa ttttttaagt tcctcgtagg tgagctcttc aggggagctg agcccgtgct    4320
ctgaaagggc ccagtctgca agatgagggt tggaagcgac gaatgagctc acaggtcac    4380
ggccattag  catttgcagg tggtcgcgaa aggtcctaaa ctggcgacct atggccattt   4440
tttctggggt gatgcagtag aaggtaagcg ggtcttgttc ccagcggtcc catccaaggt   4500
tcgcggctag gtctcgcgcg gcagtcacta gaggctcatc tccgccgaac ttcatgacca   4560
gcatgaaggg cacgagctgc ttcccaaagg ccccccatcca agtataggtc tctacatcgt   4620
aggtgacaaa gagacgctcg gtgcgaggat gcgagccgat cgggaagaac tggatctccc   4680
gccaccaatt ggaggagtgg ctattgatgt ggtgaaagta gaagtccctg cgacgggccg   4740
aacactcgtg ctggcttttg taaaaacgtg cgcagtactg gcagcggtgc acgggctgta   4800
catcctgcac gaggttgacc tgacgaccgc gcacaaggaa gcagagtggg aatttgagcc   4860
cctcgcctgg cgggttttggc tggtggtctt ctacttcggc tgcttgtcct tgaccgtctg   4920
gctgctcgag gggagttacg gtggatcgga ccaccacgcc gcgcgagccc aaagtccaga   4980
tgtccgcgcg cggcggtcgg agcttgatga caacatcgcg cagatgggag ctgtccatgg   5040
tctggagctc ccgcggcgtc aggtcaggcg ggagctcctg caggtttacc tcgcatagac   5100
gggtcagggc gcgggctaga tccaggtgat acctaatttc caggggctgg ttggtggcgg   5160
cgtcgatggc ttgcaagagg ccgcatcccc gcggcgcgac tacggtaccg cgcggcgggc   5220
ggtgggccgg ggggtgtcc  ttggatgatg catctaaaag cggtgacgcg ggcgagcccc   5280
cggaggtagg gggggctccg gacccgccgg gagaggggc  aggggcacgt cggcgccgcg   5340
cgcgggcagg agctggtgct gcgcgcgtag gttgctggcg aacgcgacga cgcggcggtt   5400
gatctcctga atctggcgcc tctgcgtgaa gacgacgggc ccggtgagct tgagcctgaa   5460
agagagttcg acagaatcaa tttcggtgtc gttgacggcg gcctggcgca aaatctcctg   5520
cacgtctcct gagttgtctt gataggcgat ctcggccatg aactgctcga tctcttcctc   5580
```

-continued

```
ctggagatct ccgcgtccgg ctcgctccac ggtggcggcg aggtcgttgg aaatgcgggc      5640
catgagctgc gagaaggcgt tgaggcctcc ctcgttccag acgcggctgt agaccacgcc      5700
cccttcggca tcgcgggcgc gcatgaccac ctgcgcgaga ttgagctcca cgtgccgggc      5760
gaagacggcg tagtttcgca ggcgctgaaa gaggtagttg agggtggtgg cggtgtgttc      5820
tgccacgaag aagtacataa cccagcgtcg caacgtggat tcgttgatat cccccaaggc      5880
ctcaaggcgc tccatggcct cgtagaagtc cacggcgaag ttgaaaaact gggagttgcg      5940
cgccgacacg gttaactcct cctccagaag acggatgagc tcggcgacag tgtcgcgcac      6000
ctcgcgctca aaggctacag gggcctcttc ttcttcttca atctcctctt ccataagggc      6060
ctccccttct tcttcttctg gcggcggtgg gggaggggga cacggcggc gacgacggcg       6120 caccgggagg cggtcgacaa agcgctcgat catctccccg cggcgacggc gcatggtctc      6180
ggtgacggcg cggccgttct cgcggggggcg cagttggaag acgccgcccg tcatgtcccg     6240
gttatgggtt ggcggggggc tgccatgcgg cagggatacg gcgctaacga tgcatctcaa     6300
caattgttgt gtaggtactc cgccgccgag ggacctgagc gagtccgcat cgaccggatc      6360
ggaaaacctc tcgagaaagg cgtctaacca gtcacagtcg caaggtaggc tgagcaccgt      6420
ggcgggcggc agcgggcggc ggtcgggggtt gtttctggcg gaggtgctgc tgatgatgta     6480
attaaagtag gcggtcttga gacggcggat ggtcgacaga agcaccatgt ccttgggtcc      6540
ggcctgctga atgcgcaggc ggtcggccat gccccaggct tcgttttgac atcggcgcag     6600
gtctttgtag tagtcttgca tgagcctttc taccggcact tcttcttctc cttcctcttg     6660
tcctgcatct cttgcatcta tcgctgcggc ggcggcggag tttggccgta ggtggcgccc     6720
tcttcctccc atgcgtgtga ccccgaagcc cctcatcggc tgaagcaggg ctaggtcggc     6780
gacaacgcgc tcggctaata tggcctgctg cacctgcgtg agggtagact ggaagtcatc      6840
catgtccaca aagcggtggt atgcgcccgt gttgatggtg taagtgcagt tggccataac     6900
ggaccagtta acggtctggt gacccggctg cgagagctcg gtgtacctga cgcgagta      6960 agccctcgag tcaaatacgt agtcgttgca agtccgcacc aggtactggt atcccaccaa     7020
aaagtgcggc ggcggctggc ggtagagggg ccagcgtagg gtggccgggg ctccggggggc    7080 gagatcttcc aacataaggc gatgatatcc gtagatgtac ctggacatcc aggtgatgcc      7140
ggcggcggtg gtggaggcgc gcggaaagtc gcggacgcgg ttccagatgt tgcgcagcgg     7200
caaaaagtgc tccatggtcg ggacgctctg gccggtcagg cgcgcgcaat cgttgacgct      7260
ctaccgtgca aaaggagagc ctgtaagcgg gcactcttcc gtggtctggt ggataaattc      7320
gcaagggtat catggcggac gaccgggggtt cgagccccgt atccgccgt ccgccgtgat      7380 ccatgcggtt accgccgcg tgtcgaaccc aggtgtgcga cgtcagacaa cggggggagtg     7440 ctcctttttgg cttccttcca ggcgcggcgg ctgctgcgct agctttttg gccactggcc      7500 gcgcgcagcg taagcggtta ggctggaaag cgaaagcatt aagtggctcg ctccctgtag     7560
ccggagggtt attttccaag ggttgagtcg cgggacccccc ggttcgagtc tcggaccggc    7620
cggactgcgg cgaacggggg tttgcctccc cgtcatgcaa gaccccgctt gcaaattcct      7680
ccggaaacag ggacgagccc ctttttttgct tttcccagat gcatccgtgc ctgcggcaga    7740
tgcgcccccc tcctcagcag cggcaagagc aagagcagcg gcagacatgc agggcaccct     7800
cccctcctcc taccgcgtca ggagggggcga catccgcggt tgacgcggca gcagatggtg    7860
attacgaacc cccgcggcgc cgggcccggc actacctgga cttggaggag ggcgagggcc     7920
```

```
tggcgcggct aggagcgccc tctcctgagc ggtacccaag ggtgcagctg aagcgtgata    7980
cgcgtgaggc gtacgtgccg cggcagaacc tgtttcgcga ccgcgaggga gaggagcccg    8040
aggagatgcg ggatcgaaag ttccacgcag ggcgcgagct gcggcatggc ctgaatcgcg    8100
agcggttgct gcgcgaggag gactttgagc ccgacgcgcg aaccgggatt agtcccgcgc    8160
gcgcacacgt ggcggccgcc gacctggtaa ccgcatacga gcagacggtg aaccaggaga    8220
ttaactttca aaaagctttt aacaaccacg tgcgtacgct tgtggcgcgc gaggaggtgg    8280
ctataggact gatgcatctg tgggactttg taagcgcgct ggagcaaaac ccaaatagca    8340
agccgctcat ggcgcagctg ttccttatag tgcagcacag cagggacaac gaggcattca    8400
gggatgcgct gctaaacata gtagagcccg agggccgctg gctgctcgat ttgataaaca    8460
tcctgcagag catagtggtg caggagcgca gcttgagcct ggctgacaag gtggccgcca    8520
tcaactattc catgcttagc ctgggcaagt tttacgcccg caagatatac catacccctt    8580
acgttcccat agacaaggag gtaaagatcg aggggttcta catgcgcatg gcgctgaagg    8640
tgcttacctt gagcgacgac ctgggcgttt atcgcaacga gcgcatccac aaggccgtga    8700
gcgtgagccg gcggcgcgag ctcagcgacc gcgagctgat gcacagcctg caaagggccc    8760
tggctggcac gggcagcggc gatagagagg ccgagtccta ctttgacgcg ggcgctgacc    8820
tgcgctgggc cccaagccga cgcgcccctgg aggcagctgg ggccggacct gggctggcgg    8880
tggcacccgc gcgcgctggc aacgtcggcg gcgtggagga atatgacgag gacgatgagt    8940
acgagccaga ggacggcgag tactaagcgg tgatgtttct gatcagatga tgcaagacgc    9000
aacggacccg gcggtgcggg cggcgctgca gagccagccg tccggcctta actccacgga    9060
cgactggcgc caggtcatgg accgcatcat gtcgctgact gcgcgcaatc ctgacgcgtt    9120
ccggcagcag ccgcaggcca accggctctc cgcaattctg gaagcggtgg tcccggcgcg    9180
cgcaaacccc acgcacgaga aggtgctggc gatcgtaaac gcgctggccg aaaacagggc    9240
catccggccc gacgaggccg gcctggtcta cgacgcgctg cttcagcgcg tggctcgtta    9300
caacagcggc aacgtgcaga ccaacctgga ccggctggtg ggggatgtgc gcgaggccgt    9360
ggcgcagcgt gagcgcgcgc agcagcaggg caacctgggc tccatggttg cactaaacgc    9420
cttcctgagt acacagcccg ccaacgtgcc gcggggacag gaggactaca ccaactttgt    9480
gagcgcactg cggctaatgg tgactgagac accgcaaagt gaggtgtacc agtctgggcc    9540
agactatttt ttccagacca gtagacaagg cctgcagacc gtaaacctga gccaggcttt    9600
caaaaacttg caggggctgt gggggggtgcg ggctcccaca ggcgaccgcg cgaccgtgtc    9660
tagcttgctg acgcccaact cgcgcctgtt gctgctgcta atagcgccct tcacggacag    9720
tggcagcgtg tcccgggaca catacctagg tcacttgctg acactgtacc gcgaggccat    9780
aggtcaggcg catgtggacg agcatacttt ccaggagatt acaagtgtca gccgcgcgct    9840
ggggcaggag gacacgggca gcctggaggc aaccctaaac tacctgctga ccaaccggcg    9900
gcagaagatc ccctcgttgc acagtttaaa cagcgaggag gagcgcattt tgcgctacgt    9960
gcagcagagc gtgagcctta acctgatgcg cgacggggta acgcccagcg tggcgctgga    10020
catgaccgcg cgcaacatgg aaccgggcat gtatgcctca aaccggccgt ttatcaaccg    10080
cctaatggac tacttgcatc gcgcggccgc cgtgaacccc gagtatttca ccaatgccat    10140
cttgaacccg cactggctac cgcccctggg tttctacacc ggggattcg aggtgcccga    10200
gggtaacgat ggattcctct gggacgcat agacgacagt gttttccc cgcaaccgca    10260
gaccctgcta gagttgcaac agcgcgagca ggcagaggcg gcgctgcgaa aggaaagctt    10320
```

```
ccgcaggcca agcagcttgt ccgatctagg cgctgcggcc ccgcggtcag atgctagtag    10380
cccatttcca agcttgatag ggtctcttac cagcactcgc accacccgcc cgcgcctgct    10440
gggcgaggag gagtacctaa acaactcgct gctgcagccg cagcgcgaaa aaaacctgcc    10500
tccggcattt cccaacaacg ggatagagag cctagtggac aagatgagta gatggaagac    10560
gtacgcgcag gagcacaggg acgtgccagg cccgcgcccg cccacccgtc gtcaaaggca    10620
cgaccgtcag cggggtctgg tgtgggagga cgatgactcg gcagacgaca gcagcgtcct    10680
ggatttggga gggagtggca acccgtttgc gcaccttcgc cccaggctgg ggagaatgtt    10740
ttaaaaaaaa aaaagcatga tgcaaaataa aaaactcacc aaggccatgg caccgagcgt    10800
tggttttctt gtattcccct tagtatgcgc gcgcgggcga tgtatgagga aggtcctcct    10860
ccctcctacg agagtgtggt gagcgcggcg ccagtggcgg cggcgctggg ttctcccttc    10920
gatgctcccc tggacccgcc gtttgtgcct ccgcggtacc tgcggcctac cggggggaga    10980
aacagcatcc gttactctga gttggcaccc ctattcgaca ccacccgtgt gtacctggtg    11040
gacaacaagt caacggatgt ggcatcccta aactaccaga acgaccacag caactttctg    11100
accacggtca ttcaaaacaa tgactacagc ccggggagg caagcacaca gaccatcaat    11160
cttgacgacc ggtcgcactg gggcggcgac ctgaaaacca tcctgcatac caacatgcca    11220
aatgtgaacg agttcatgtt taccaataag tttaaggcgc gggtgatggt gtcgcgcttg    11280
cctactaagg acaatcaggt ggagctgaaa tacgagtggg tggagttcac gctgcccgag    11340
ggcaactact ccgagaccat gaccatagac cttatgaaca acgcgatcgt ggagcactac    11400
ttgaaagtgg gcagacagaa cggggttctg gaaagcgaca tcgggtaaa gtttgacacc    11460 cgcaacttca gactggggtt tgaccccgtc actggtcttg tcatgcctgg ggtatataca    11520
aacgaagcct tccatccaga catcattttg ctgccaggat gcggggtgga cttcacccac    11580
agccgcctga gcaacttgtt gggcatccgc aagcggcaac ccttccagga gggctttagg    11640
atcacctacg atgatctgga gggtggtaac attcccgcac tgttggatgt ggacgcctac    11700
caggcgagct tgaaagatga caccgaacag ggcggggtg cgcaggcgg cagcaacagc    11760 agtggcagcg gcgcggaaga gaactccaac gcggcagccg cggcaatgca gccggtggag    11820
gacatgaacg atcatgccat tcgcggcgac acctttgcca cacgggctga ggagaagcgc    11880
gctgaggccg aagcagcggc cgaagctgcc gcccccgctg cgcaacccga ggtcgagaag    11940
cctcagaaga aaccggtgat caaacccctg acagaggaca gcaagaaacg cagttacaac    12000
ctaataagca atgacagcac cttcacccag taccgcagct ggtaccttgc atacaactac    12060
ggcgaccctc agaccggaat ccgctcatgg accctgcttt gcactcctga cgtaacctgc    12120
ggctcggagc aggtctactg gtcgttgcca gacatgatgc aagacccgt gaccttccgc    12180 tccacgcgcc agatcagcaa ctttcggtg gtgggcgccg agctgttgcc cgtgcactcc    12240
aagagcttct acaacgacca ggccgtctac tcccaactca tccgccagtt tacctctctg    12300
acccacgtgt tcaatcgctt tcccgagaac cagattttgg cgcgcccgcc agcccccacc    12360
atcaccaccg tcagtgaaaa cgttcctgct ctcacagatc acgggacgct accgctgcgc    12420
aacagcatcg gaggagtcca gcgagtgacc attactgacg ccagacgccg cacctgcccc    12480
tacgtttaca aggccctggg catagtctcg ccgcgcgtcc tatcgagccg cactttttga    12540
gcaagcatgt ccatccttat atcgcccagc aataacacag gctggggcct gcgcttccca    12600
agcaagatgt ttggcggggc caagaagcgc tccgaccaac acccagtgcg cgtgcgcggg    12660
```

```
cactaccgcg cgccctgggg cgcgcacaaa cgcggccgca ctgggcgcac caccgtcgat   12720
gacgccatcg acgcggtggt ggaggaggcg cgcaactaca cgcccacgcc gccaccagtg   12780
tccacagtgg acgcggccat tcagaccgtg gtgcgcggag cccggcgcta tgctaaaatg   12840
aagagacggc ggaggcgcgt agcacgtcgc caccgccgcc gacccggcac tgccgcccaa   12900
cgcgcggcgg cggccctgct taaccgcgca cgtcgcaccg gccgacgggc ggccatgcgg   12960
gccgctcgaa ggctggccgc gggtattgtc actgtgcccc ccaggtccag cgacgagcg    13020 gccgccgcag cagccgcggc cattagtgct atgactcagg gtcgcagggg caacgtgtat   13080
tgggtgcgcg actcggttag cggcctgcgc gtgcccgtgc gcaccgcccc ccgcgcaac    13140 tagattgcaa gaaaaaacta cttagactcg tactgttgta tgtatccagc ggcggcggcg   13200
cgcaacgaag ctatgtccaa gcgcaaaatc aagaagaga tgctccaggt catcgcgccg    13260
gagatctatg gccccccgaa gaaggaagag caggattaca agccccgaaa gctaaagcgg   13320
gtcaaaaaga aaagaaaga tgatgatgat gaacttgacg acgaggtgga actgctgcac    13380
gctaccgcgc ccaggcgacg ggtacagtgg aaaggtcgac gcgtaaaacg tgttttgcga   13440
cccggcacca ccgtagtctt tacgcccggt gagcgctcca cccgcaccta caagcgcgtg   13500
tatgatgagg tgtacggcga cgaggacctg cttgagcagg ccaacgagcg cctcggggag   13560
tttgcctacg gaaagcggca taaggacatg ctggcgttgc cgctggacga gggcaaccca   13620
acacctagcc taaagcccgt aacactgcag caggtgctgc ccgcgcttgc accgtccgaa   13680
gaaaagcgcg gcctaaagcg cgagtctggt gacttggcac ccaccgtgca gctgatggta   13740
cccaagcgcc agcgactgga agatgtcttg gaaaaaatga ccgtggaacc tgggctggag   13800
cccgaggtcc gcgtgcggcc aatcaagcag gtggcgccgg gactgggcgt gcagaccgtg   13860
gacgttcaga tacccactac cagtagcacc agtattgcca ccgccacaga gggcatggag   13920
acacaaacgt ccccggttgc ctcagcggtg gcggatgccg cggtgcaggc ggtcgctgcg   13980
gccgcgtcca agacctctac ggaggtgcaa acggacccgt ggatgtttcg cgtttcagcc   14040 cccggcgcc cgcgcggttc gaggaagtac ggcgccgcca gcgcgctact gcccgaatat   14100
gccctacatc cttccattgc gcctaccccc ggctatcgtg gctacaccta ccgccccaga   14160
agacgagcaa ctacccgacg ccgaaccacc actggaaccc gccgccgccg tcgccgtcgc   14220
cagcccgtgc tggcccgat ttccgtgcgc agggtggctc gcgaaggagg caggaccctg    14280
gtgctgccaa cagcgcgcta ccaccccagc atcgtttaaa agccggtctt tgtggttctt   14340
gcagatatgg ccctcacctg ccgcctccgt ttccggtgc cgggattccg aggaagaatg    14400
caccgtagga ggggcatggc cggccacggc ctgacgggcg gcatgcgtcg tgcgcaccac   14460
cggcggcggc gcgcgtcgca ccgtcgcatg cgcggcggta tcctgcccct ccttattcca   14520
ctgatcgccg cggcgattgg cgccgtgccc ggaattgcat ccgtggcctt gcaggcgcag   14580
agacactgat taaaaacaag ttgcatgtgg aaaaatcaaa ataaaagtc tggactctca    14640 cgctcgcttg gtcctgtaac tattttgtag aatggaagac atcaactttg cgtctctggc   14700
cccgcgacac ggctcgcgcc cgttcatggg aaactgcaa gatatcggca ccagcaatat    14760
gagcggtggc gccttcagct ggggctcgct gtggagcggc attaaaaatt tcggttccac   14820
cgttaagaac tatggcagca aggcctggaa cagcagcaca ggccagatgc tgagggataa   14880
gttgaaagag caaaatttcc aacaaaaggt ggtagatggc ctggcctctg gcattagcgg   14940
ggtggtggac ctgccaaacc aggcagtgca aaataagatt aacagtaagc ttgatccccg   15000
ccctcccgta gaggagcctc caccggccgt ggagacagtg tctccagagg ggcgtggcga   15060
```

-continued

```
aaagcgtccg cgccccgaca gggaagaaac tctggtgacg caaatagacg agcctccctc   15120
gtacgaggag gcactaaagc aaggcctgcc caccacccgt cccatcgcgc ccatggctac   15180
cggagtgctg ggccagcaca cacccgtaac gctggacctg cctcccccg ccgacaccca   15240 gcagaaacct gtgctgccag gcccgaccgc cgttgttgta acccgtccta gccgcgcgtc   15300
cctgcgccgc gccgccagcg gtccgcgatc gttgcggccc gtagccagtg caactggca   15360 aagcacactg aacagcatcg tgggtctggg ggtgcaatcc ctgaagcgcc gacgatgctt   15420
ctgaatagct aacgtgtcgt atgtgtgtca tgtatgcgtc catgtcgccg ccagaggagc   15480
tgctgagccg ccgcgcgccc gctttccaag atggctaccc cttcgatgat gccgcagtgg   15540
tcttacatgc acatctcggg ccaggacgcc tcggagtacc tgagcccgg gctggtgcag   15600 tttgcccgcg ccaccgagac gtacttcagc ctgaataaca agtttagaaa ccccacggtg   15660
gcgcctacgc acgacgtgac cacagaccgg tcccagcgtt tgacgctgcg gttcatccct   15720
gtggaccgtg aggatactgc gtactcgtac aaggcgcggt tcaccctagc tgtgggtgat   15780
aaccgtgtgc tggacatggc ttccacgtac tttgacatcc gcggcgtgct ggacaggggc   15840
cctactttta agccctactc tggcactgcc tacaacgccc tggctcccaa gggtgcccca   15900
aatccttgcg aatgggatga agctgctact gctcttgaaa taaacctaga agaagaggac   15960
gatgacaacg aagacgaagt agacgagcaa gctgagcagc aaaaaactca cgtatttggg   16020
caggcgcctt attctggtat aaatattaca aaggagggta ttcaaatagg tgtcgaaggt   16080
caaacaccta aatatgccga taaaacattt caacctgaac tcaaatagg agaatctcag   16140 tggtacgaaa ctgaaattaa tcatgcagct gggagagtcc ttaaaaagac taccccaatg   16200
aaaccatgtt acggttcata tgcaaaaccc acaaatgaaa atggagggca aggcattctt   16260
gtaaagcaac aaaatggaaa gctagaaagt caagtggaaa tgcaattttt ctcaactact   16320
gaggcgaccg caggcaatgg tgataacttg actcctaaag tggtattgta cagtgaagat   16380
gtagatatag aaaccccaga cactcatatt tcttacatgc ccactattaa ggaaggtaac   16440
tcacgagaac taatgggcca acaatctatg cccaacaggc ctaattacat tgcttttagg   16500 gacaattta ttggtctaat gtattacaac agcacgggta atatgggtgt tctggcgggc   16560
caagcatcgc agttgaatgc tgttgtagat ttgcaagaca gaaacacaga gctttcatac   16620
cagcttttgc ttgattccat tggtgataga accaggtact tttctatgtg gaatcaggct   16680
gttgacagct atgatccaga tgttagaatt attgaaaatc atggaactga agatgaactt   16740
ccaaattact gctttccact gggaggtgtg attaatacag agactcttac caaggtaaaa   16800
cctaaaacag gtcaggaaaa tggatgggaa aaagatgcta cagaattttc agataaaaat   16860
gaaataagag ttggaaataa ttttgccatg gaaatcaatc taaatgccaa cctgtggaga   16920
aatttcctgt actccaacat agcgctgtat ttgcccgaca agctaaagta cagtccttcc   16980
aacgtaaaaa tttctgataa cccaaacacc tacgactaca tgaacaagcg agtggtggct   17040
cccgggttag tggactgcta cattaacctt ggagcacgct ggtccttga ctatatggac   17100 aacgtcaacc catttaacca ccaccgcaat gctggcctgc gctaccgctc aatgttgctg   17160
ggcaatggtc gctatgtgcc cttccacatc caggtgcctc agaagttctt tgccattaaa   17220
aacctccttc tcctgccggg ctcatacacc tacgagtgga acttcaggaa ggatgttaac   17280
atggttctgc agagctccct aggaaatgac ctaaggggttg acggagccag cattaagttt   17340
gatagcattt gcctttacgc caccttcttc cccatggccc acaacaccgc ctccacgctt   17400
```

```
gaggccatgc ttagaaacga caccaacgac cagtccttta acgactatct ctccgccgcc    17460
aacatgctct accctatacc cgccaacgct accaacgtgc ccatatccat ccctcccgc     17520
aactgggcgg ctttccgcgg ctgggccttc acgcgcctta agactaagga aaccccatca    17580
ctgggctcgg gctacgaccc ttattacacc tactctggct ctataccta cctagatgga    17640
accttttacc tcaaccacac ctttaagaag gtggccatta cctttgactc ttctgtcagc    17700
tggcctggca atgaccgcct gcttaccccc aacgagtttg aaattaagcg ctcagttgac    17760
ggggagggtt acaacgttgc ccagtgtaac atgaccaaag actggttcct ggtacaaatg    17820
ctagctaact acaacattgg ctaccagggc ttctatatcc cagagagcta caaggaccgc    17880
atgtactcct tctttagaaa cttccagccc atgagccgtc aggtggtgga tgatactaaa    17940
tacaaggact accaacaggt gggcatccta caccaacaca acaactctgg atttgttggc    18000
taccttgccc ccaccatgcg cgaaggacag gcctaccctg ctaacttccc ctatccgctt    18060
ataggcaaga ccgcagttga cagcattacc cagaaaaagt ttctttgcga tcgcacccct    18120
tggcgcatcc cattctccag taactttatg tccatgggcg cactcacaga cctgggccaa    18180
aaccttctct acgccaactc cgcccacgcg ctagacatga cttttgaggt ggatcccatg    18240
gacgagccca cccttcttta tgttttgttt gaagtctttg acgtggtccg tgtgcaccgg    18300
ccgcaccgcg gcgtcatcga aaccgtgtac ctgcgcacgc ccttctcggc cggcaacgcc    18360
acaacataaa gaagcaagca acatcaacaa cagctgccgc catgggctcc agtgagcagg    18420
aactgaaagc cattgtcaaa gatcttggtt gtgggccata ttttttgggc acctatgaca    18480
agcgctttcc aggctttgtt tctccacaca agctcgcctg cgccatagtc aatacggccg    18540
gtcgcgagac tgggggcgta cactggatgg cctttgcctg gaacccgcac tcaaaaacat    18600
gctacctctt tgagcccttt ggcttttctg accagcgact caagcaggtt taccagtttg    18660
agtacgagtc actcctgcgc cgtagcgcca ttgcttcttc ccccgaccgc tgtataacgc    18720
tggaaaagtc cacccaaagc gtacaggggc ccaactcggc cgcctgtgga ctattctgct    18780
gcatgtttct ccacgccttt gccaactggc cccaaactcc catggatcac aaccccacca    18840
tgaaccttat taccggggta cccaactcca tgctcaacag tccccaggta cagcccaccc    18900
tgcgtcgcaa ccaggaacag ctctacagct tcctggagcg ccactcgccc tacttccgca    18960
gccacagtgc gcagattagg agcgccactt ctttttgtca cttgaaaaac atgtaaaaat    19020
aatgtactag agacactttc aataaaggca aatgctttta tttgtacact ctcgggtgat    19080
tatttacccc caccccttgcc gtctgcgccg tttaaaaatc aaagggggttc tgccgcgcat    19140
cgctatgcgc cactggcagg gacacgttgc gatactggtg tttagtgctc cacttaaact    19200
caggcacaac catccgcggc agctcggtga agttttcact ccacaggctg cgcaccatca    19260
ccaacgcgtt tagcaggtcg ggcgccgata tcttgaagtc gcagttgggg cctccgccct    19320
gcgcgcgcga gttgcgatac acagggttgc agcactggaa cactatcagc gccggtggt    19380
gcacgctggc cagcacgctc ttgtcggaga tcagatccgc gtccaggtcc tccgcgttgc    19440
tcagggcgaa cggagtcaac tttggtagct gccttcccaa aaagggcgcg tgcccaggct    19500
ttgagttgca ctcgcaccgt agtggcatca aaaggtgacc gtgcccggtc tgggcgttag    19560
gatacagcgc ctgcataaaa gccttgatct gcttaaaagc cacctgagcc tttgcgcctt    19620
cagagaagaa catgccgcaa gacttgccgg aaaactgatt ggccggacag gccgcgtcgt    19680
gcacgcagca ccttgcgtcg gtgttggaga tctgcaccac atttcggccc caccggttct    19740
tcacgatctt ggccttgcta gactgctcct tcagcgcgcg ctgcccgttt tcgctcgtca    19800
```

```
catccatttc aatcacgtgc tccttattta tcataatgct tccgtgtaga cacttaagct  19860
cgccttcgat ctcagcgcag cggtgcagcc acaacgcgca gcccgtgggc tcgtgatgct  19920
tgtaggtcac ctctgcaaac gactgcaggt acgcctgcag gaatcgcccc atcatcgtca  19980
caaaggtctt gttgctggtg aaggtcagct gcaacccgcg gtgctcctcg ttcagccagg  20040
tcttgcatac ggccgccaga gcttccactt ggtcaggcag tagtttgaag ttcgccttta  20100
gatcgttatc cacgtggtac ttgtccatca gcgcgcgcgc agcctccatg cccttctccc  20160
acgcagacac gatcggcaca ctcagcgggt tcatcaccgt aatttcactt tccgcttcgc  20220
tgggctcttc ctcttcctct tgcgtccgca taccacgcgc cactgggtcg tcttcattca  20280
gccgccgcac tgtgcgctta cctcctttgc catgcttgat tagcaccggt gggttgctga  20340
aacccaccat ttgtagcgcc acatcttctc tttcttcctc gctgtccacg attacctctg  20400
gtgatggcgg gcgctcgggc ttgggagaag ggcgcttctt tttcttcttg ggcgcaatgg  20460
ccaaatccgc cgccgaggtc gatggccgcg ggctgggtgt gcgcggcacc agcgcgtctt  20520
gtgatgagtc ttcctcgtcc tcggactcga tacgccgcct catccgcttt tttgggggcg  20580
cccggggagg cggcggcgac ggggacgggg acgacacgtc ctccatggtt ggggacgtc  20640
gcgccgcacc gcgtccgcgc tcggggggtgg tttcgcgctg ctcctcttcc cgactggcca  20700
tttccttctc ctataggcag aaaaagatca tggagtcagt cgagaagaag gacagcctaa  20760
ccgcccctc tgagttcgcc accaccgcct ccaccgatgc cgccaacgcg cctaccacct  20820
tccccgtcga ggcaccccg cttgaggagg aggaagtgat tatcgagcag gacccaggtt  20880
ttgtaagcga agacgacgag gaccgctcag taccaacaga ggataaaaag caagaccagg  20940
acaacgcaga ggcaaacgag gaacaagtcg ggcggggga cgaaaggcat ggcgactacc  21000
tagatgtggg agacgacgtg ctgttgaagc atctgcagcg ccagtgcgcc attatctgcg  21060
acgcgttgca agagcgcagc gatgtgcccc tcgccatagc ggatgtcagc cttgcctacg  21120
aacgccacct attctcaccg cgcgtacccc ccaaacgcca agaaaacggc acatgcgagc  21180
ccaacccgcg cctcaacttc tacccgtat ttgccgtgcc agaggtgctt gccacctatc  21240
acatcttttt ccaaaactgc aagatacccc tatcctgccg tgccaaccgc agccgagcgg  21300
acaagcagct ggccttgcgg cagggcgctg tcatacctga tatcgcctcg ctcaacgaag  21360
tgccaaaaat ctttgagggt cttggacgcg acgagaagcg cgcggcaaac gctctgcaac  21420
aggaaaacag cgaaaatgaa agtcactctg gagtgttggt ggaactcgag ggtgacaacg  21480
cgcgcctagc cgtactaaaa cgcagcatcg aggtcaccca ctttgcctac ccggcactta  21540
acctaccccc caaggtcatg agcacagtca tgagtgagct gatcgtgcgc cgtgcgcagc  21600
ccctggagag ggatgcaaat ttgcaagaac aaacagagga gggcctaccc gcagttggcg  21660
acgagcagct agcgcgctgg cttcaaacgc gcgagcctgc cgacttggag gagcgacgca  21720
aactaatgat ggccgcagtg ctcgttaccg tggagcttga gtgcatgcag cggttctttg  21780
ctgacccgga gatgcagcgc aagctagagg aaacattgca ctaccctttt cgacagggct  21840
acgtacgcca ggcctgcaag atctccaacg tggagctctg caacctggtc tcctaccttg  21900
gaatttttgca cgaaaccgc cttgggcaaa acgtgcttca ttccacgctc aagggcgagg  21960
cgcgccgcga ctacgtccgc gactgcgttt acttatttct atgctacacc tggcagacgg  22020
ccatgggcgt ttggcagcag tgcttggagg agtgcaacct caaggagctg cagaaactgc  22080
taaagcaaaa cttgaaggac ctatggacgg ccttcaacga gcgctccgtg gccgcgcacc  22140
```

-continued

```
tggcggacat cattttcccc gaacgcctgc ttaaaaccct gcaacagggt ctgccagact      22200
tcaccagtca aagcatgttg cagaacttta ggaactttat cctagagcgc tcaggaatct      22260
tgcccgccac ctgctgtgca cttcctagcg actttgtgcc cattaagtac cgcgaatgcc      22320
ctccgccgct ttggggccac tgctaccttc tgcagctagc caactacctt gcctaccact      22380
ctgacataat ggaagacgtg agcggtgacg gtctactgga gtgtcactgt cgctgcaacc      22440
tatgcacccc gcaccgctcc ctggtttgca attcgcagct gcttaacgaa agtcaaatta      22500
tcggtaccct tgagctgcag ggtccctcgc ctgacgaaaa gtccgcggct ccggggttga      22560
aactcactcc ggggctgtgg acgtcggctt accttcgcaa atttgtacct gaggactacc      22620
acgcccacga gattaggttc tacgaagacc aatcccgccc gccaaatgcg gagcttaccg      22680
cctgcgtcat tacccaggge cacattcttg gccaattgca agccatcaac aaagcccgcc      22740
aagagtttct gctacgaaag ggacgggggg tttacttgga cccccagtcc ggcgaggagc      22800
tcaacccaat ccccccgccg ccgcagccct atcagcagca gccgcgggcc cttgcttccc      22860
aggatggcac ccaaaaagaa gctgcagctg ccgccgccac ccacggacga ggaggaatac      22920
tgggacagtc aggcagagga ggttttggac gaggaggagg aggacatgat ggaagactgg      22980
gagagcctag acgaggaagc ttccgaggtc aaagaggtgt cagacgaaac accgtcaccc      23040
tcggtcgcat tccctcgcc ggcgcccag aaatcggcaa ccggttccag catggctaca      23100
acctccgctc ctcaggcgcc gccggcactg cccgttcgcc gacccaaccg tagatgggac      23160
accactggaa ccagggccgg taagtccaag cagccgccgc cgttagccca agagcaacaa      23220
cagcgccaag gctaccgctc atggcgcggg cacaagaacg ccatagttgc ttgcttgcaa      23280
gactgtgggg gcaacatctc cttcgcccgc cgctttcttc tctaccatca cggcgtggcc      23340
ttcccccgta acatcctgca ttactaccgt catctctaca gcccatactg caccggcggc      23400
agcggcagcg gcagcaacag cagcggccac acagaagcaa aggcgaccgg atagcaagac      23460
tctgacaaag cccaagaaat ccacagcggc ggcagcagca ggaggaggag cgctgcgtct      23520
ggcgcccaac gaacccgtat cgaccgcga gcttagaaac aggatttttc ccactctgta      23580
tgctatattt caacagagca ggggccaaga acaagagctg aaaataaaaa acaggtctct      23640
gcgatccctc acccgcagct gcctgtatca caaaagcgaa gatcagcttc ggcgcacgct      23700
ggaagacgcg gaggctctct tcagtaaata ctgcgcgctg actcttaagg actagtttcg      23760
cgcccttttct caaatttaag cgcgaaaact acgtcatctc cagcggccac acccggcgcc      23820
agcacctgtc gtcagcgcca ttatgagcaa ggaaattccc acgccctaca tgtggagtta      23880
ccagccacaa atgggacttg cggctggagc tgcccaagac tactcaaccc gaataaacta      23940
catgagcgcg ggaccccaca tgatatcccg ggtcaacgga atccgcgccc accgaaaccg      24000
aattctcttg gaacaggcgg ctattaccac cacacctcgt aataaccta atccccgtag       24060
ttggcccgct gccctggtgt accaggaaag tcccgctccc accactgtgg tacttccag       24120
agacgcccag gccgaagttc agatgactaa ctcaggggcg cagcttgcgg cggctttcg       24180
tcacagggtg cggtcgcccg ggcagggtat aactcacctg acaatcagag ggcgaggtat      24240
tcagctcaac gacgagtcgg tgagctcctc gcttggtctc cgtccggacg ggacatttca      24300
gatcggcggc gccggccgtc cttcattcac gcctcgtcag gcaatcctaa ctctgcagac      24360
ctcgtcctct gagccgcgct ctggaggcat tggaactctg caatttattg aggagtttgt      24420
gccatcggtc tactttaacc ccttctcggg acctccccgc cactatccgg atcaatttat      24480
tcctaacttt gacgcggtaa aggactcggc ggacggctac gactgaatgt taagtggaga      24540
```

-continued

```
ggcagagcaa ctgcgcctga aacacctggt ccactgtcgc cgccacaagt gctttgcccg    24600
cgactccggt gagttttgct actttgaatt gcccgaggat catatcgagg gcccggcgca    24660
cggcgtccgg cttaccgccc agggagagct tgcccgtagc ctgattcggg agtttaccca    24720 gcgcccctg ctagttgagc gggacagggg accctgtgtt ctcactgtga tttgcaactg     24780
tcctaacctt ggattacatc aagatctttg ttgccatctc tgtgctgagt ataataaata    24840
cagaaattaa aatatactgg ggctcctatc gccatcctgt aaacgccacc gtcttcaccc    24900
gcccaagcaa accaaggcga accttacctg gtacttttaa catctctccc tctgtgattt    24960
acaacagttt caacccagac ggagtgagtc tacgagagaa cctctccgag ctcagctact    25020
ccatcagaaa aaacaccacc ctccttacct gccgggaacg tacgagtgcg tcaccggccg    25080
ctgcaccaca cctaccgcct gaccgtaaac cagactttt ccggacagac ctcaataact     25140
ctgtttacca gaacaggagg tgagcttaga aaacccttag ggtattaggc caaaggcgca    25200
gctactgtgg ggtttatgaa caattcaagc aactctacgg gctattctaa ttcaggtttc    25260
tctaatcggg gttggggtta ttctctgtct tgtgattctc tttattctta tactaacgct    25320
tctctgccta aggctcgccg cctgctgtgt gcacatttgc atttattgtc agcttttttaa   25380 acgctggggt cgccacccaa gatgattagg tacataatcc taggtttact caccccttgcg   25440 tcagcccacg gtaccaccca aaaggtggat tttaaggagc cagcctgtaa tgttacattc    25500
gcagctgaag ctaatgagtg caccactctt ataaaatgca ccacagaaca tgaaaagctg    25560
cttattcgcc acaaaaacaa aattggcaag tatgctgttt atgctatttg gcagccaggt    25620
gacactacag agtataatgt tacagttttc cagggtaaaa gtcataaaac ttttatgtat    25680
acttttccat tttatgaaat gtgcgacatt accatgtaca tgagcaaaca gtataagttg    25740
tggcccccac aaaattgtgt ggaaaacact ggcactttct gctgcactgc tatgctaatt    25800
acagtgctcg ctttggtctg taccctactc tatattaaat acaaaagcag acgcagcttt    25860
attgaggaaa agaaaatgcc ttaatttact aagttacaaa gctaatgtca ccactaactg    25920
ctttactcgc tgcttgcaaa acaaattcaa aaagttagca ttataattag aataggattt    25980 aaacccccg gtcatttcct gctcaatacc attccctga caattgact ctatgtggga      26040 tatgctccag cgctacaacc ttgaagtcag gcttcctgga tgtcagcatc tgactttggc    26100
cagcacctgt cccgcggatt tgttccagtc caactacagc gacccaccct aacagagatg    26160
accaacacaa ccaacgcggc cgccgctacc ggacttacat ctaccacaaa tacaccccaa    26220
gtttctgcct ttgtcaataa ctgggataac ttgggcatgt ggtggttctc catagcgctt    26280
atgtttgtat gccttattat tatgtggctc atctgctgcc taaagcgcaa acgcgcccga    26340
ccacccatct atagtcccat cattgtgcta cacccaaaca atgatggaat ccatagattg    26400
gacggactga aacacatgtt cttttctctt acagtatgat taaatgagac atgattcctc    26460 gagttttat attactgacc cttgttgcgc ttttttgtgc gtgctccaca ttggctgcgg     26520
tttctcacat cgaagtagac tgcattccag ccttcacagt ctatttgctt tacggatttg    26580
tcaccctcac gctcatctgc agcctcatca ctgtggtcat cgcctttatc cagtgcattg    26640
actgggtctg tgtgcgcttt gcatatctca gacaccatcc ccagtacagg gacaggacta    26700
tagctgagct tcttagaaat ggacggaatt attacagagc agcgcctgct agaaagacgc    26760
agggcagcgg ccgagcaaca gcgcatgaat caagagctcc aagacatggt taacttgcac    26820
cagtgcaaaa gggtatctt ttgtctggta aagcaggcca aagtcaccta cgacagtaat     26880
```

```
accaccggac accgccttag ctacaagttg ccaaccaagc gtcagaaatt ggtggtcatg   26940
gtgggagaaa agcccattac cataactcag cactcggtag aaaccgaagg ctgcattcac   27000
tcaccttgtc aaggacctga ggatctctgc acccttatta agaccctgtg cggtctcaaa   27060
gatcttattc cctttaacta ataaaaaaaa ataataaagc atcacttact taaaatcagt   27120
tagcaaattt ctgtccagtt tattcagcag cacctccttg ccctcctccc agctctggta   27180
ttgcagcttc ctcctggctg caaactttct ccacaatcta aatggaatgt cagtttcctc   27240
ctgttcctgt ccatccgcac ccactatctt catgttgttg cagatgaagc gcgcaagacc   27300
gtctgaagat accttcaacc ccgtgtatcc atatgacacg gaaaccggtc ctccaactgt   27360
gccttttctt actcctccct ttgtatcccc caatgggttt caagagagtc cccctggggt   27420
actctctttg cgcctatccg aacctctagt tacctccaat ggcatgcttg cgctcaaaat   27480
gggcaacggc ctctctctgg acgaggccgg caaccttacc tcccaaaatg taaccactgt   27540
gagcccacct ctcaaaaaaa ccaagtcaaa cataaacctg gaaatatctg caccccctcac  27600 agttacctca gaagccctaa ctgtggctgc cgccgcacct ctaatggtcg cgggcaacac   27660
actcaccatg caatcacagg ccccgctaac cgtgcacgac tccaaactta gcattgccac   27720
ccaaggaccc ctcacagtgt cagaaggaaa gctagccctg caaacatcag gccccctcac   27780
caccaccgat agcagtaccc ttactatcac tgcctcaccc cctctaacta ctgccactgg   27840
tagcttgggc attgacttga aagagcccat ttatacacaa aatggaaaac taggactaaa   27900
gtacggggct ccttttgcatg taacagacga cctaaaacact ttgaccgtag caactggtcc   27960
aggtgtgact attaataata cttccttgca aactaaagtt actggagcct gggttttga   28020 ttcacaaggc aatatgcaac ttaatgtagc aggaggacta aggattgatt ctcaaaacag   28080
acgccttata cttgatgtta gttatccgtt tgatgctcaa aaccaactaa atctaagact   28140
aggacagggc cctctttttta taaactcagc ccacaacttg gatattaact acaacaaagg   28200
cctttacttg tttacagctt caaacaattc caaaaagctt gaggttaacc taagcactgc   28260 caagggttg atgtttgacg ctacagccat agccattaat gcaggagatg ggcttgaatt   28320
tggttcacct aatgcaccaa acacaaatcc cctcaaaaca aaaattggcc atggcctaga   28380
atttgattca aacaaggcta tggttcctaa actaggaact ggcctagtt ttgacagcac   28440 aggtgccatt acagtaggaa acaaaaataa tgataagcta actttgtgga ccacaccagc   28500
tccatctcct aactgtagac taaatgcaga gaaagatgct aaaactcactt tggtcttaac   28560 aaaatgtggc agtcaaatac ttgctacagt ttcagttttg gctgttaaag gcagtttggc   28620
tccaatatct ggaacagttc aaagtgctca tcttattata agatttgacg aaaatggagt   28680
gctactaaac aattccttcc tggacccaga atattggaac tttagaaatg gagatcttac   28740
tgaaggcaca gcctatacaa acgctgttgg atttatgcct aacctatcag cttatccaaa   28800
atctcacggt aaaactgcca aaagtaacat tgtcagtcaa gtttacttaa acggagacaa   28860 aactaaaccct gtaacactaa ccattacact aaacggtaca caggaaacag gagacacaac   28920
tccaagtgca tactctatgt cattttcatg ggactggtct ggccacaact acattaatga   28980
aatatttgcc acatcctctt acactttttc atacattgcc caagaataaa gaatcgtttg   29040
tgttatgttt caacgtgttt atttttcaat tgcagaaaat ttcaagtcat ttttcattca   29100
gtagtatagc cccaccacca catagcttat acagatcacc gtaccttaat caaactcaca   29160 gaacccctagt attcaacctg ccacctccct cccaacacac agagtacaca gtcctttctc   29220
cccggctggc cttaaaaagc atcatatcat gggtaacaga catattctta ggtgttatat   29280
```

-continued

```
tccacacggt tcctgtcga gccaaacgct catcagtgat attaataaac tccccgggca    29340
gctcacttaa gttcatgtcg ctgtccagct gctgagccac aggctgctgt ccaacttgcg    29400
gttgcttaac gggcggcgaa ggagaagtcc acgcctacat gggggtagag tcataatcgt    29460
gcatcaggat agggcggtgg tgctgcagca gcgcgcgaat aaactgctgc cgccgccgct    29520
ccgtcctgca ggaatacaac atggcagtgg tctcctcagc gatgattcgc accgcccgca    29580
gcataaggcg ccttgtcctc cgggcacagc agcgcaccct gatctcactt aaatcagcac    29640
agtaactgca gcacagcacc acaatattgt tcaaaatccc acagtgcaag gcgctgtatc    29700
caaagctcat ggcggggacc acagaaccca cgtggccatc ataccacaag cgcaggtaga    29760
ttaagtggcg acccctcata aacacgctgg acataaacat tacctctttt ggcatgttgt    29820
aattcaccac ctcccggtac catataaacc tctgattaaa catggcgcca tccaccacca    29880
tcctaaacca gctggccaaa acctgcccgc cggctataca ctgcagggaa ccgggactgg    29940
aacaatgaca gtggagagcc caggactcgt aaccatggat catcatgctc gtcatgatat    30000
caatgttggc acaacacagg cacacgtgca tacacttcct caggattaca agctcctccc    30060
gcgttagaac catatcccag ggaacaaccc attcctgaat cagcgtaaat cccacactgc    30120
agggaagacc tcgcacgtaa ctcacgttgt gcattgtcaa agtgttacat tcggcagca    30180
gcggatgatc ctccagtatg gtagcgcggg tttctgtctc aaaggaggt agacgatccc    30240
tactgtacgg agtgcgccga gacaaccgag atcgtgttgg tcgtagtgtc atgccaaatg    30300
gaacgccgga cgtagtcata tttcctgaag caaaaccagg tgcgggcgtg acaaacagat    30360
ctgcgtctcc ggtctcgccg cttagatcgc tctgtgtagt agttgtagta tatccactct    30420
ctcaaagcat ccaggcgccc cctggcttcg ggttctatgt aaactccttc atgcgccgct    30480
gccctgataa catccaccac cgcagaataa gccacaccca gccaacctac acattcgttc    30540
tgcgagtcac acacgggagg agcgggaaga gctggaagaa ccatgttttt tttttattc    30600
caaaagatta tccaaaacct caaaatgaag atctattaag tgaacgcgct cccctccggt    30660
ggcgtggtca aactctacag ccaaagaaca gataatggca tttgtaagat gttgcacaat    30720
ggcttccaaa aggcaaacgg ccctcacgtc caagtggacg taaaggctaa acccttcagg    30780
gtgaatctcc tctataaaca ttccagcacc ttcaaccatg cccaaataat tctcatctcg    30840
ccaccttctc aatatatctc taagcaaatc ccgaatatta agtccggcca ttgtaaaaat    30900
ctgctccaga gcgccctcca ccttcagcct caagcagcga atcatgattg caaaaattca    30960
ggttcctcac agacctgtat aagattcaaa agcggaacat taacaaaaat accgcgatcc    31020
cgtaggtccc ttcgcagggc cagctgaaca taatcgtgca ggtctgcacg gaccagcgcg    31080
gccacttccc cgccaggaac cttgacaaaa gaacccacac tgattatgac acgcatactc    31140
ggagctatgc taaccagcgt agccccgatg taagctttgt tgcatgggcg gcgatataaa    31200
atgcaaggtg ctgctcaaaa aatcaggcaa agcctcgcgc aaaaagaaa gcacatcgta    31260
gtcatgctca tgcagataaa ggcaggtaag ctccggaacc accacagaaa aagacaccat    31320
ttttctctca aacatgtctg cgggtttctg cataaacaca aaataaaata acaaaaaaac    31380
atttaaacat tagaagcctg tcttacaaca ggaaaaacaa cccttataag cataagacgg    31440
actacggcca tgccggcgtg accgtaaaaa aactggtcac cgtgattaaa aagcaccacc    31500
gacagctcct cggtcatgtc cggagtcata atgtaagact cggtaaacac atcaggttga    31560
ttcatcggtc agtgctaaaa agcgaccgaa atagcccggg ggaatacata cccgcaggcg    31620
```

-continued

| | | | | | |
|---|---|---|---|---|---|
| tagagacaac | attacagccc | ccataggagg | tataacaaaa | ttaataggag | agaaaaacac | 31680 |
| ataaacacct | gaaaaaccct | cctgcctagg | caaaatagca | ccctcccgct | ccagaacaac | 31740 |
| atacagcgct | tcacagcggc | agcctaacag | tcagccttac | cagtaaaaaa | gaaaacctat | 31800 |
| taaaaaaaca | ccactcgaca | cggcaccagc | tcaatcagtc | acagtgtaaa | aaagggccaa | 31860 |
| gtgcagagcg | agtatatata | ggactaaaaa | atgacgtaac | ggttaaagtc | cacaaaaaac | 31920 |
| acccagaaaa | ccgcacgcga | acctacgccc | agaaacgaaa | gccaaaaaac | ccacaacttc | 31980 |
| ctcaaatcgt | cacttccgtt | ttcccacgtt | acgtaacttc | ccattttaag | aaaactacaa | 32040 |
| ttcccaacac | atacaagtta | ctccgcccta | aaacctacgt | cacccgcccc | gttcccacgc | 32100 |
| cccgcgccac | gtcacaaact | ccaccccctc | attatcatat | tggcttcaat | ccaaaataag | 32160 |
| gtatat | | | | | | 32166 |